(12) United States Patent
Carbone et al.

(10) Patent No.: US 10,702,623 B2
(45) Date of Patent: Jul. 7, 2020

(54) APPARATUS AND METHOD FOR TREATING IMPURITIES IN AIR AND MATERIALS

(71) Applicant: Bluezone IP Holdings, LLC, Woburn, MA (US)

(72) Inventors: Philip C. Carbone, North Reading, MA (US); Karen Benedek, Winchester, MA (US); Peter J. Loftus, Cambridge, MA (US); David Hensel, Boston, MA (US); Anna Cheimets, Somerville, MA (US); James Poon, Woburn, MA (US); Elizabeth Gillis, Winchester, MA (US); Warren James Ellis, Worcester, MA (US); Charles Marble, Brockton, MA (US)

(73) Assignee: BLUEZONE IP HOLDING LLC, Woburn, MA (US)

( * ) Notice: Subject to any disclaimer, the term of this patent is extended or adjusted under 35 U.S.C. 154(b) by 169 days.

(21) Appl. No.: 15/461,432

(22) Filed: Mar. 16, 2017

(65) Prior Publication Data
US 2017/0246333 A1    Aug. 31, 2017

Related U.S. Application Data

(63) Continuation-in-part of application No. 13/784,503, filed on Mar. 4, 2013, now abandoned, which is a
(Continued)

(51) Int. Cl.
*A61L 9/20* (2006.01)
*A61L 9/12* (2006.01)
(Continued)

(52) U.S. Cl.
CPC ............... *A61L 9/12* (2013.01); *A61L 2/202* (2013.01); *B60H 3/0085* (2013.01);
(Continued)

(58) Field of Classification Search
CPC ................................ A61L 9/20; A61L 9/015
See application file for complete search history.

(56) References Cited

U.S. PATENT DOCUMENTS

| 2,628,083 A | 2/1953 | Rense |
| 3,071,828 A | 1/1963 | Cornell |

(Continued)

FOREIGN PATENT DOCUMENTS

| DE | 3637702 A1 | 5/1988 |
| EP | 0269941 A1 | 6/1988 |

(Continued)

OTHER PUBLICATIONS

Co-pending U.S. Appl. No. 15/461,433, Benedek et al., "Air Treatment System," filed Mar. 16, 2017.
(Continued)

*Primary Examiner* — Donald R Spamer
(74) *Attorney, Agent, or Firm* — Pauley Erickson & Kottis

(57) ABSTRACT

An apparatus for treating air includes a housing with an air inlet and an air outlet, the housing enclosing an air treatment zone and an ozone removal zone, wherein the ozone removal zone is positioned downstream of the air treatment zone with respect to a flow direction of the air being treated, an ultraviolet (UV) light source in the air treatment zone configured to generate ozone from the air, wherein the UV light from the UV light source and the ozone generated by the UV light source treat the air in the air treatment zone, catalyst in the ozone removal zone that removes at least a portion of the ozone generated by the UV light source, and an air mover positioned near the air outlet configured to draw the air through the air inlet into the air treatment zone from outside the housing.

19 Claims, 47 Drawing Sheets

Related U.S. Application Data continuation-in-part of application No. 13/512,564, filed as application No. PCT/US2010/002741 on Oct. 14, 2010, now abandoned, and a continuation-in-part of application No. 12/587,948, filed on Oct. 14, 2009, now Pat. No. 8,388,900, which is a continuation-in-part of application No. 12/312,690, filed as application No. PCT/US2007/024347 on Nov. 21, 2007, now Pat. No. 8,114,358, which is a continuation-in-part of application No. 11/603,669, filed on Nov. 21, 2006, now abandoned.

(60) Provisional application No. 61/341,349, filed on Mar. 30, 2010.

(51) Int. Cl.
  *B60H 3/00* (2006.01)
  *A61L 2/20* (2006.01)
  *B60H 3/02* (2006.01)

(52) U.S. Cl.
  CPC ....... *A61L 2202/13* (2013.01); *A61L 2202/26* (2013.01); *A61L 2209/15* (2013.01); *A61L 2209/212* (2013.01); *B60H 3/02* (2013.01)

(56) References Cited

U.S. PATENT DOCUMENTS

| | | | |
|---|---|---|---|
| 4,210,429 A | 7/1980 | Golstein | |
| 4,302,677 A | 11/1981 | Albertsson et al. | |
| 4,343,765 A | 8/1982 | Elston et al. | |
| 4,904,289 A | 2/1990 | Miyakami et al. | |
| 4,990,311 A | 2/1991 | Hirai et al. | |
| 5,015,442 A | 5/1991 | Hirai | |
| 5,029,252 A | 7/1991 | Ameseder | |
| 5,152,077 A | 10/1992 | Liang | |
| 5,230,220 A | 7/1993 | Kang et al. | |
| 5,262,130 A | 11/1993 | Kissel et al. | |
| 5,326,539 A | 7/1994 | Taylor | |
| 5,369,892 A | 12/1994 | Dhaemers | |
| 5,505,904 A * | 4/1996 | Haidinger | A61L 9/20 250/435 |
| 5,523,057 A | 6/1996 | Mazzilli | |
| 5,601,786 A | 2/1997 | Monagan | |
| 5,788,930 A | 8/1998 | McMurray | |
| 5,853,457 A | 12/1998 | Eysmondt et al. | |
| 5,925,320 A | 7/1999 | Jones | |
| 6,093,237 A | 7/2000 | Keller et al. | |
| 6,134,806 A | 10/2000 | Dhaemers | |
| 6,391,272 B1 | 5/2002 | Schroeder | |
| 6,500,387 B1 | 12/2002 | Bigelow | |
| 6,613,277 B1 | 9/2003 | Monagan | |
| 6,845,569 B1 | 1/2005 | Kim | |
| 6,893,610 B1 | 5/2005 | Barnes | |
| 8,114,358 B2 | 2/2012 | Benedek et al. | |
| 8,388,900 B2 | 3/2013 | Benedek et al. | |
| 2002/0031460 A1 * | 3/2002 | Kulp | F24F 3/16 422/292 |
| 2002/0098109 A1 | 7/2002 | Nelson et al. | |
| 2002/0139124 A1 | 10/2002 | Palermo | |
| 2003/0206840 A1 * | 11/2003 | Taylor | A61L 9/015 422/186.04 |
| 2004/0003511 A1 | 1/2004 | Silver | |
| 2004/0120845 A1 | 6/2004 | Potember et al. | |
| 2004/0146437 A1 | 7/2004 | Arts et al. | |
| 2004/0161371 A1 | 8/2004 | Russell et al. | |
| 2005/0069465 A1 | 3/2005 | McEllen | |
| 2005/0089458 A1 | 4/2005 | Oke | |
| 2005/0129591 A1 * | 6/2005 | Wei | A61L 9/205 422/186 |
| 2005/0175498 A1 | 8/2005 | Nelson et al. | |
| 2005/0186108 A1 | 8/2005 | Fields | |
| 2006/0032199 A1 * | 2/2006 | Beam | B01D 46/0028 55/471 |
| 2006/0104858 A1 | 5/2006 | Potember et al. | |
| 2008/0118395 A1 | 5/2008 | Benedek | |
| 2010/0054989 A1 | 3/2010 | Benedek et al. | |
| 2010/0158749 A1 | 6/2010 | Benedek et al. | |
| 2012/0244036 A1 | 9/2012 | Benedek et al. | |
| 2013/0256560 A1 * | 10/2013 | Yerby | A61L 2/10 250/455.11 |
| 2013/0287626 A1 | 10/2013 | Benedek et al. | |
| 2014/0193296 A1 | 7/2014 | Jurak et al. | |

FOREIGN PATENT DOCUMENTS

| | | |
|---|---|---|
| JP | 2002263181 A | 9/2002 |
| JP | 2005226861 A | 8/2005 |
| WO | WO-9002572 A1 | 3/1990 |
| WO | WO-03080375 A1 | 10/2003 |
| WO | WO-2008103719 A1 | 8/2008 |
| WO | WO-2008127315 A2 | 10/2008 |
| WO | WO 2016/080903 A1 | 5/2016 |

OTHER PUBLICATIONS

PCT International Search Report from International Application No. PCT/IB2017/000433, Form PCT/ISA/210, dated Sep. 27, 2017, (3 pages).

PCT Written Opinion of the International Searching Authority from International Application No. PCT/IB2017/000433, Form PCT/ISA/237, dated Sep. 27, 2017, (9 pages).

\* cited by examiner

| Lamp Catalog Number | | Nominal Lamp Length | Lamp Watts | Approximate Lamp Current mA | Ultraviolet Output | | Ozone Output | Rated Effective Life (hrs) |
|---|---|---|---|---|---|---|---|---|
| Ozone Free | Ozone Producing | | | | Total Watts | Microwatts @ 1 meter | | |
| G18T6L/U | G18T6VH/U | 8-1/4" | 17 | 425 | 5.8 | 59 | 1.6 | 10,000 |
| G24T6L/U | G24T6VH/U | 11-1/4" | 25 | 425 | 8.5 | 82 | 2.3 | 10,000 |
| G30T6L/U | G30T6VH/U | 14-1/4" | 32 | 425 | 11.2 | 101 | 3.0 | 10,000 |
| G36T6L/U | G36T6VH/U | 17-1/4" | 39 | 425 | 13.8 | 120 | 3.7 | 10,000 |
| G48T6L/U | G48T6VH/U | 23-1/4" | 50 | 425 | 19.3 | 164 | 5.2 | 10,000 |

FIG.8

| Common Name | Ethylene Production | Ethylene Sensitivity |
|---|---|---|
| Apple | Very High (>100µl/kg-hr) | Highly Sensitive |
| Banana | Moderate (1-10µl/kg-hr) | Highly Sensitive |
| Broccoli | Very Low (<0.1µl/kg-hr) | Highly Sensitive |
| Citrus (oranges) | Very Low (<0.1µl/kg-hr) | Moderately Sensitive |
| Pears | High (10-100µl/kg-hr) | Highly Sensitive |
| Tomatoes (ripe) | Very Low (<0.1µl/kg-hr) | Highly Sensitive |
| Tomatoes (unripe) | High (10-100µl/kg-hr) | Low Sensitive |

FIG.9

| Known Ethylene Control Technology | Limitation for Transport and Storage Applications |
|---|---|
| Ventilation | Refrigerated shipping containers and storage facilities or devices are not designed for significant ventilation due to energy requirements to condition outside air, risk of contamination, risk of drying-out the fruit and vegetables, and difficulty ventilating individual cartons of fresh fruit and vegetables (FF&V) |
| Potassium Permanginate (KMnO$_4$) (absorption/catalytic oxidation of C$_2$H$_4$ to H$_2$O and CO$_2$) | One-time use, this produce poses an environmental and cost burden due to the need to dispose of the KMnO$_4$ as a hazardous waste |
| Bromated Carbon (absorbent) | Costly and waste products must be disposed |
| Catalytic Oxidizers (e.g. TiO$_2$ photocatalytic oxidation, C$_2$H$_4$ to H$_2$O and CO$_2$) | High pressure drop of catalytic reactor leads to excessive power requirement for air-flow through the reactor, it is difficult to draw the air out of individual FF&V shipping cartons to be cleaned, and long residence times required for significant ethylene reduction effectiveness results in an excessively large system. |

FIG.10

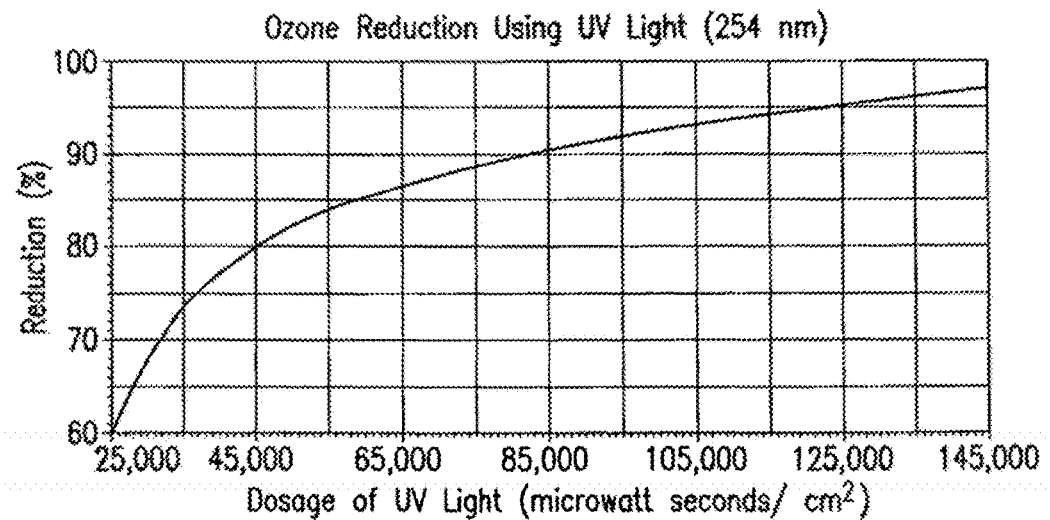

FIG.11

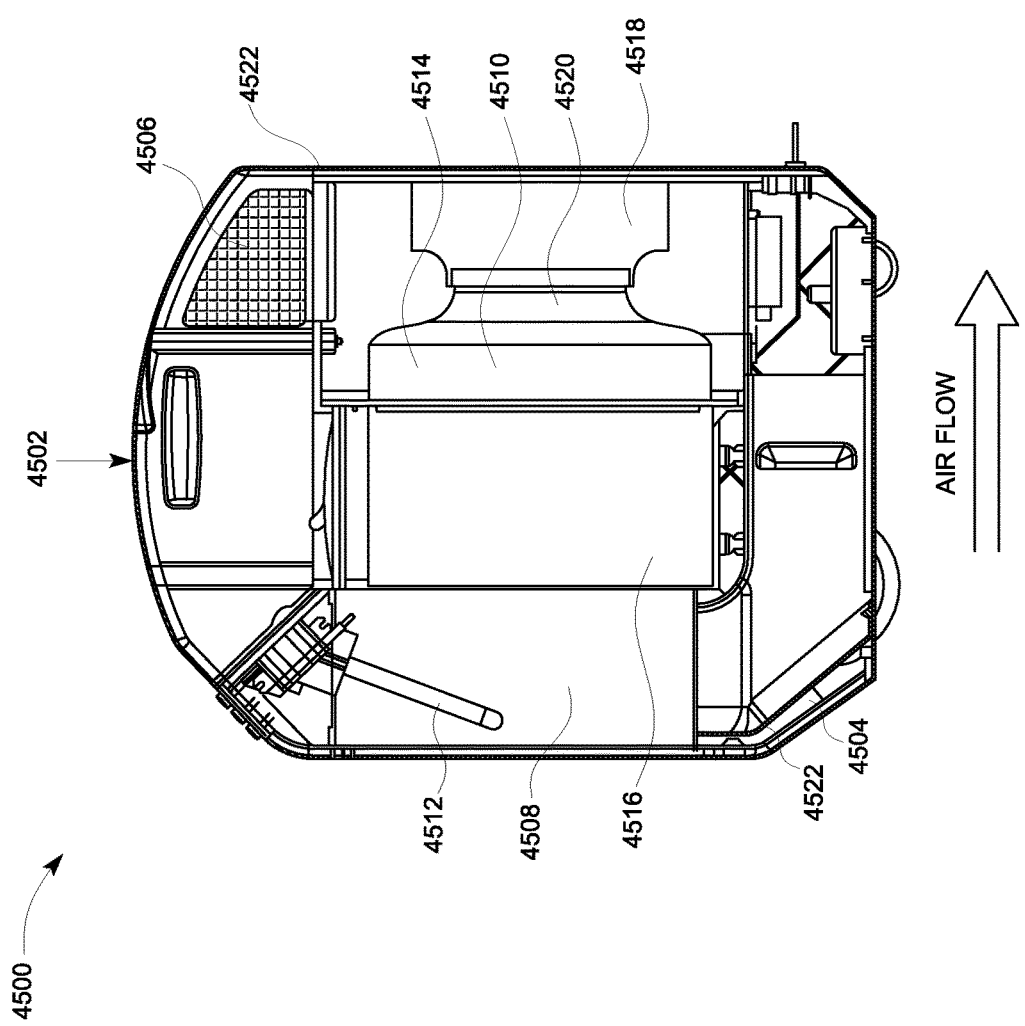

[CONTINUED]

APPARATUS AND METHOD FOR TREATING IMPURITIES IN AIR AND MATERIALS

RELATED APPLICATIONS

This application is a continuation-in-part of and claims priority to U.S. patent application Ser. No. 13/784,503 filed on Mar. 4, 2013, which is a continuation-in-part of U.S. patent application Ser. No. 13/512,564 filed on May 29, 2012, which is a National Stage Entry of PCT Application PCT/US2010/002741 filed on Oct. 14, 2010, which claims priority to U.S. Provisional Application 61/341,349 filed on Mar. 30, 2010 and is a continuation-in-part of U.S. patent application Ser. No. 12/587,948 filed on Oct. 14, 2009 and now U.S. Pat. No. 8,388,900, which is a continuation-in-part of U.S. patent application Ser. No. 12/312,690 filed May 21, 2009 and now U.S. Pat. No. 8,114,358, which is a National Stage Entry of PCT Application PCT/US2007/024347 filed on Nov. 21, 2007, which is a continuation-in-part of U.S. patent application Ser. No. 11/603,669 filed Nov. 21, 2006. The disclosure of these related patent applications are incorporated herein by reference in their entirety.

TECHNICAL FIELD

The subject matter described herein relates generally to cleaning air, and more specifically to materials, apparatuses, assemblies and methods for treating air such as by removing one or more impurities from the air.

In one aspect, the subject matter disclosed herein relates to methods and assemblies for treating an atmosphere that has been exposed to a material within an enclosed space so as to remove impurities from the atmosphere. Such impurity removal may involve one or more of a treatment to sanitize, decontaminate, deodorize, condition and/or dry the atmosphere, for example. Such methods and assemblies may employ UV light to generate ozone, the ozone in conjunction with UV light to destroy impurities in the air, and then uses a catalytic decomposer to destroy ozone so that damaging ozone does not contact the sensitive materials or surfaces being cleaned. In one aspect, the subject matter disclosed herein employs an integral ozone fuse to help ensure the treated atmosphere does not contain levels of ozone above desired limits. In another aspect, the system may be operated with a control sequence that may periodically reverse and/or alter the air flow direction in order to introduce ozone into the atmosphere directly to achieve a desired dosage of ozone on the materials in the enclosed space. In some embodiments of the subject matter disclosed herein, the control sequence may revert to the original flow direction and/or flow path in order to remove the ozone as well as other contaminants from the atmosphere.

BACKGROUND

A wide range of sports equipment is designed and used to protect the human body from injury. Equipment pieces are relatively large, bulky, oddly shaped, fitted with straps, and difficult to wash and dry. In soccer, a player wears shin guards and ankle guards to protect the lower leg. In hockey, a player wears knee pads, a chest protector, elbow pads, gloves, a helmet and hockey pants. In football, a player wears shoulder pads, leg and hip pads, a helmet, a neck roll, elbow pads and gloves. Bicyclists and roller blade skaters use helmets. Many sports require general or specialized footwear, such as cleats, sneakers, spikes, skates, roller blades and the like. Workers can wear similar equipment. Protective equipment can be worn with direct contact against a skin or a head surface. Whether the equipment directly contacts the human body or is separated by clothing or a piece of cloth, sweat soaks into materials, such as pads, elastic material, straps, foam, and other materials. If not properly dried or cleaned, the sweat-soaked equipment becomes a site for growth of bacteria, mold, mildew, fungus, and other microorganisms that can spread disease, cause odor and/or damage or discolor the equipment. The equipment and the bag, bin or other storage container can become malodorous. Odors from the equipment can emanate from or through the container and make unpleasant the corresponding room, such as a vehicle compartment. Merely blowing air across the equipment to dry the equipment can more broadly release odors from the evaporated sweat and moisture into the room, house or other compartment. It is desirable to have an apparatus and/or method for drying, deodorizing, and/or sanitizing equipment and/or its surrounding air or atmosphere, quickly and conveniently.

Known products in the marketplace have addressed this need. Dhaemers, U.S. Pat. No. 6,134,806 describes a portable sport equipment bag having an air distributor connected with a hose to a blower and an ozone generator operable to move pressurized air and ozone into the air distributor. The air distributor moves the air and ozone into the bag to dry the sports equipment contained within the bag, to destroy bacteria, molds and fungus in the bag. The ozone directly contacts the sports equipment, which can be a serious problem because ozone can destroy many equipment materials, such as when the ozone exists in air at concentrations that are high enough to kill undesirable microorganisms. When well mixed with contaminated air, ozone can more effectively and efficiently oxidize contaminants. Also, ozone is a lung irritant and can leak out of the equipment bag and dangerously be inhaled, such as when the user opens the sports equipment bag. These safety issues can be serious enough to warrant alternative approaches.

Dhaemers, U.S. Pat. No. 5,369,892 describes a dryer in the form of an armoire with an internal drying chamber for housing articles that are subjected to heated circulating air, to remove moisture from the articles. Ultraviolet lamps within the drying chamber destroy contaminants in the air and on the air conditioning coils, in the drying chamber. A similar configuration is taught by Liang, U.S. Pat. No. 5,152,077, which is limited because contaminated materials must be in a direct line of sight of a UV light source, in order to be sanitized. The clothes alone can restrict exposure between the material and the UV light. Air that circulates in the armoire cannot be deodorized.

There is a need for a convenient, efficient, cost effective and efficient method and apparatus for drying, deodorizing and/or sanitizing air and equipment, particularly without damaging the equipment.

Many other types of products can benefit from being dried, sanitized and deodorized, such as toys used at home or in commercial or institutional settings, including health care facilities, day care centers and/or schools. The materials used in toys and stuffed animals make it difficult to clean them quickly and conveniently. Many toys need to be individually wiped with disinfectant to clean their surfaces. Disinfectants and wipes can be used to clean toys. These cleaning procedures are time consuming and burdensome.

There is a need for a method and apparatus for drying, deodorizing, and/or sanitizing a variety of products, quickly, safely and/or effectively, with minimal physical or chemical impact to the products.

Ethylene gas ($C_2H_4$) accumulates during the transport and storage of fresh fruits and vegetables and thus causes a problem for commercial agriculture and consumers. Small amounts of ethylene, sometimes less than 1 ppm, can induce fruit ripening, and can produce undesirable flavors such as bitterness, colors, such as yellowing or browning, and textures, such as softening, and thus can increase susceptibility to disease. Certain fruits and vegetables naturally generate ethylene during a ripening cycle. Other fruits and vegetables are highly sensitive to the presence of ethylene, but may or may not actually produce ethylene. The table in FIG. 9 lists some fruits and vegetables and known ethylene production rates and sensitivities.

The amount of ethylene that produces undesirable amounts or characteristics varies with different fruits and vegetables, but ethylene concentrations in the range of 0.1-10 ppm can produce a significant effect. There is a need for a system that removes ethylene from the air within a fruit or vegetable storage container while not damaging the fruits or vegetables.

In addition, mold and fungus and other microbes on the surfaces of food products, such as fresh produce can lead to damage of or total loss of the infected fruits or vegetables. The mold and fungus can release spores as part of their life cycle that circulate through the air and subsequently infect other fruit or vegetable items that are in contact with the same atmosphere. There is a need for a system that can kill the microbes on the surface of the produce and/or in the air circulating around the produce.

Ozone is known to be able to kill mold and fungus and other microbes on surfaces and in the atmosphere when provided in sufficient dosage, such as in time and concentration. UV light is known to kill microbes at defined exposures, such as at frequency, power level and time.

Because there is significant industry value in maintaining fresh fruits and vegetables during transportation and storage, some technologies have been researched, developed and commercialized to control ethylene. These conventional methods and their limitations are shown in the table of FIG. 10.

Residential, commercial and industrial spaces can have atmospheres that are contaminated with odors, gases, volatile organic compounds, microbes and/or allergens that cause discomfort or health hazards to people occupying those spaces. Conventional air cleaning technologies filter the air with materials that trap or otherwise adsorb or absorb gases, odors, microbes and/or allergens. These trapped or otherwise held contaminants are always present in the filters and can be re-emitted into the atmosphere. One preferred air cleaning approach would be to convert the odors, gases and/or volatile organic compounds into harmless compounds that are not noticed by or cause harm to occupants in the room. It is also preferable for an air purifier to inactivate microbes and/or alter allergens in a way that renders them harmless rather than to capture the particles. That way, there is less need to replace filters that are filled with particulates and other contaminants that can be re-emitted into the atmosphere.

There is a need for an alternative approach to ethylene and microbial control that would be less expensive, consume less power, and require less space. There is a need for an alternative approach to air cleaning that would convert or inactivate rather than capture contaminants in the atmosphere. There is also a need for an alternative approach to air cleaning that incorporates a self-clean function to deodorize and sanitize the particulate filters that capture material.

SUMMARY

It is an object of the subject matter disclosed herein to provide an improved method and/or apparatus for treating an atmosphere exposed to a material within an enclosed space.

In one aspect there is provided an apparatus and method for oxidizing ethylene to carbon dioxide and water using UV-generated ozone in conjunction with UV light.

It is another object of an aspect of the subject matter disclosed herein to produce ozone to destroy ethylene and then to dissociate the excess ozone back to oxygen, to maintain acceptable levels of ozone within a shipping or storage container, for example that carries fresh fruits and vegetables. According to one embodiment, at least a portion of the ethylene can be destroyed in each pass through a cleaning unit or apparatus in accordance with the subject matter disclosed herein so that the atmosphere in the storage container is cleaned by repeated circulation through the cleaning apparatus. As long as the rate of destruction of ethylene is higher than the rate of generation of ethylene in the storage container, the cleaning apparatus will reduce the ethylene levels to a desired steady-state level. By designing the cleaning apparatus to partially clean the atmosphere, and relying on recirculation of the atmosphere to reduce the contaminants to desired levels, the balance between system performance, volume and cost can be better optimized.

It is another object of an aspect of the subject matter disclosed herein to provide cost effective assemblies and/or methods for better ensuring that ozone is not released into the ambient air in unsafe levels or amounts such as through an automatic shutdown of the assembly if the ozone level in the exhaust reaches a preselected threshold level or sums to a specified, integrated level over a particular period of time.

According to one embodiment, ethylene can be oxidized in an ethylene control unit while microbes may be treated on the surface of materials and/or in the atmosphere, such as at lower ozone concentration. This dual approach can maximize ethylene removal from the container air and address mold or fungus on the produce packages or the produce surfaces. This dual approach can also minimize negative effects of ozone concentrations in an air handling system or in the produce itself. UV-generated ozone can also be used to remove additional pathogens that can degrade produce quality, such as with certain fungus or mold spores. Such an apparatus and method can meet application requirements of a wide range of container sizes and refrigeration or other environmental control systems.

Such a method and system can generate, use, and destroy ozone, for example to remove ethylene and/or other impurities in the air or atmosphere within fresh fruit and vegetable containers. In one embodiment, ozone is both generated and destroyed by UV light rays. The ethylene removal apparatus and/or method can be accomplished with a wide variety of known configurations of storage containers, air flow patterns and/or refrigeration units.

According to such aspect of the subject matter disclosed herein, it is possible to dry, deodorize and sanitize materials and/or the air or atmosphere that surrounds the materials. The materials can be sports equipment stored in a sports bag or an equipment bin, toys stored in a toy box and/or fruits or vegetables stored in a refrigerator or produce storage container.

It is possible to clean, deodorize, and sanitize materials by circulating cleaned and conditioned air across the materials.

The contaminants that are transferred from the materials to the air are treated in an air cleaning unit. The cleaned air is circulated back across the materials, such as in a convective manner. Air flow and/or heat can be used to drive the contaminants from the materials into the air. The contaminants can be, for example, moisture, volatile matter, such as odors, bacteria, spores, dirt, or other gases, liquids and/or microorganisms.

The contaminants that are driven into an air stream can be drawn into a compact, low-cost, effective cleaning unit where the contaminants are destroyed. The cleaned air can be re-circulated back to the storage container.

Also provided are a method and device to generate, use, and ultimately at least partially destroy the generated ozone for decontamination, deodorization, and/or conditioning of the air and/or the materials. The air cleaning unit can be positioned inside a chamber of various suitable configurations or designs. Air that requires treatment is drawn from the chamber into the cleaning unit, passes across an ozone generator, such as a UV bulb that emits light rays in the UV wavelength that generates ozone. In one embodiment it has been found that the combination of ozone and UV light serve to rapidly destroy contaminates within the cleaning unit. The clean air is then drawn across a second UV bulb that emits in the UV wavelength that destroys ozone. Alternatively, the treated air can be drawn across a catalyst to dissociate ozone to molecule oxygen. Clean, ozone-free air is then reintroduced to the storage chamber.

One or more additional treatment devices may be placed in the chamber to heat, dry, cool or dilute the air stream that circulates through the air cleaning unit.

There is also provided a method for at least one of sanitizing, decontaminating, deodorizing, conditioning and drying an atmosphere exposed to a material within an enclosed space. In accordance with one embodiment, such method involves circulating the atmosphere through an atmosphere treating unit in a primary flow direction. Ozone is generated within the atmosphere treating unit. The generated ozone mixes with the atmosphere in the atmosphere treating unit. The mixture of atmosphere and ozone is exposed to UV light in the atmosphere treating unit to remove at least a portion of the contaminants in the atmosphere. The ozone is removed from the UV light-exposed mixture of atmosphere and ozone to form an ozone-depleted containing an amount of ozone below a preselected threshold amount. The ozone-depleted mixture can then be appropriately exhausted into the enclosed space. In some embodiments of the subject matter disclosed herein, a control system is employed to reverse the flow of the blower, thereby passing or flowing air containing ozone out of the air treating unit and into the enclosed space. This reversed air flow can be timed or controlled with a sensor in a way to provide a defined dosage of ozone into the enclosed space. Once the dose or dosage is delivered, the flow direction can be reversed again to the primary flow direction so that both the contaminants in the air and the ozone in the air can be removed.

The system of the subject matter disclosed herein, which includes the apparatus and/or the method, can produce ozone to destroy contaminants and then used to dissociate the excess ozone back to oxygen in order to maintain appropriate levels of ozone within the storage container. The system of the subject matter disclosed herein provides a number of significant benefits compared to existing technology.

Circulation of air and ozone in the presence of UV light through a well-designed unit can be more efficient at cleaning the air as compared to injecting gaseous ozone, at non-hazardous levels, into still or calm air or other ambient conditions. It appears that at low concentrations of ozone, random encounters with contaminants results in too slow of a process of contaminant removal. The reaction of ozone with ethylene or other organic gases is greatly enhanced in the presence of UV light. However, there can be significant benefits to combining both of these methods to maximize benefits obtained from the use of ozone.

The subject matter disclosed herein provides two opportunities to oxidize the odors and the microorganisms, one in an air cleaning unit, and the second, such as at a lower ozone concentration, in the ambient air of the storage container. This dual approach can better remove impurities from the air in the storage container and from surfaces of the materials. Ozone concentrations are relatively high in the air cleaning unit and the mixing rates between the ozone and the air is relatively high, and thus the oxidation rates of the impurities is relatively high. The air in the storage container can be quickly deodorized and sanitized. By establishing the desired control sequence of flow direction through the air treating unit, the concentration of ozone in the enclosed space can be precisely established. A very low concentration of ozone can be established in the storage container in order to sanitize surfaces of the materials. This dual approach can minimize negative effects of ozone concentrations in the air handling system or the surface of the sports or other equipment.

It is another object of the subject matter disclosed herein to clean the air in a space such as a room in a residential, commercial, or industrial building. The subject matter disclosed herein cleans the air by inactivating, altering and/or converting these contaminants into harmless gases and/or particles. The subject matter disclosed herein is an alternative to filtering or capturing contaminants in a way that requires frequent replacement of filters and allows for the re-emission of these unaltered contaminants back into the atmosphere.

It is another object of the subject matter disclosed herein to provide a self-cleaning function, e.g., by exposing a filter to ozone and UV to deodorize and sanitize as well as oxidize material captured on the filter and/or by exposing the catalyst to UV and ozone to clean/refresh the catalyst from adsorption of organic compounds.

The disclosed subject matter describes, among other things, an assembly and method for treating or otherwise improving an atmosphere contained within an enclosed space. The enclosed space can be a container such as a bag or other housing for equipment, food and/or suitable material, or a room, another similar space and/or environment within a residential building space, a commercial building space, an industrial building space and/or a space of any other similar building structure. Ozone is generated within the assembly from the air drawn from an atmosphere that is exposed to the material. The generated ozone is mixed with the atmosphere in the presence of UV light. The ozone reacts with contaminants in the presence of UV light and removes or inactivates those contaminants from the atmosphere. The UV light and ozone inactivate microbes and alter the proteins on allergens. At least a portion of the generated ozone is then removed from the mixed atmosphere. The assembly and method can be used to treat the air in a room, or to treat contaminated sports equipment and the like, as well as to treat food storage atmospheres, such as those exposed to fresh fruits and vegetables.

In accordance with the disclosed subject matter, apparatuses, systems, and methods are described for treating impurities in air and materials.

Disclosed subject matter includes, in one aspect, an apparatus for treating air, which includes a housing with an air inlet and an air outlet, the housing enclosing an air treatment zone and an ozone removal zone, wherein the ozone removal zone is positioned downstream of the air treatment zone with respect to a flow direction of the air being treated, an ultraviolet (UV) light source in the air treatment zone configured to generate ozone from the air, wherein the UV light from the UV light source and the ozone generated by the UV light source treat the air in the air treatment zone, catalyst in the ozone removal zone that removes at least a portion of the ozone generated by the UV light source, and an air mover positioned near the air outlet configured to draw the air through the air inlet into the air treatment zone from outside the housing, moving the air through the air treatment zone and the ozone removal zone, and then emitting the air through the air outlet out of the apparatus.

In some embodiments, in the apparatus for treating air, the ozone removal zone comprises a first catalyst section hosting the catalyst, a second catalyst section hosting the catalyst, and a spacer positioned between the first and second catalyst sections.

In some embodiments, the apparatus for treating air further includes a proximity sensor attached to the housing, wherein the proximity sensor detects the presence of a cover outside the housing.

In some embodiments, in the apparatus for treating air, the proximity sensor is a magnetic proximity sensor.

In some embodiments, in the apparatus for treating air, the UV light source is turned on only if the proximity sensor detects the presence of the cover.

In some embodiments, the apparatus for treating air further includes a power connector that connects to a power source inside a refrigerator.

In some embodiments, in the apparatus for treating air, an interior surface of the housing in the air treatment zone is at least partially coated with a reflector layer.

In some embodiments, in the apparatus for treating air, the interior surface of the housing in the air treatment zone is at least partially coated with aluminum.

Disclosed subject matter includes, in another aspect, a refrigerator containing the apparatus for treating air, wherein the power connector of the apparatus for treating air is connected to a power source inside the refrigerator.

In some embodiments, in the refrigerator, the apparatus for treating air is mounted inside the refrigerator near or next to an evaporator of the refrigerator.

Disclosed subject matter includes, in another aspect, an apparatus for treating air, which includes a housing with an air inlet and an air outlet, the housing enclosing an air treatment zone and an ozone removal zone, wherein the ozone removal zone is positioned downstream of the air treatment zone with respect to a flow direction of the air being treated, an ultraviolet (UV) light source in the air treatment zone configured to generate ozone from the air, wherein the UV light from the UV light source and the ozone generated by the UV light source treat the air in the air treatment zone, a light baffle configured to shield the UV light from emitting outside the housing, catalyst in the ozone removal zone that removes at least a portion of the ozone generated the UV light source, and an air mover positioned near the air outlet configured to draw the air through the air inlet into the air treatment zone from outside the housing, moving the air through the air treatment zone and the ozone removal zone, and then emitting the air through the air outlet out of the apparatus.

In some embodiments, the apparatus for treating air further includes a positioner configured to secure the apparatus inside a cabin of a vehicle.

In some embodiments, in the apparatus for treating air, the positioner is configured to secure the apparatus into a cup holder inside the cabin of the vehicle.

In some embodiments, in the apparatus for treating air, the positioner is configured to secure the apparatus into a seat of the vehicle.

In some embodiments, in the apparatus for treating air, an interior surface of the housing in the air treatment zone is at least partially coated with a reflector layer.

In some embodiments, in the apparatus for treating air, the interior surface of the housing in the air treatment zone is at least partially coated with aluminum.

In some embodiments, the apparatus for treating air further includes a ballast configured to convert power received from the vehicle to higher frequency and higher voltage suitable for the apparatus.

Disclosed subject matter includes, in yet another aspect, an apparatus for treating air, which includes a housing with an air inlet and an air outlet, the housing enclosing an air treatment zone and an ozone removal zone, wherein the ozone removal zone is positioned downstream of the air treatment zone with respect to a flow direction of the air being treated, an ozone generator in the air treatment zone configured to generate ozone from the air, wherein the generated ozone treats the air in the air treatment zone, an ozone remover in the ozone removal zone that removes at least a portion of the ozone generated by the ozone generator, and an air mover positioned near the air outlet configured to draw the air through the air inlet into the air treatment zone from outside the housing, moving the air through the air treatment zone and the ozone removal zone, and then emitting the air through the air outlet out of the apparatus.

In some embodiments, in the apparatus for treating air, the ozone generator includes an ultraviolet (UV) light source.

In some embodiments, in the apparatus for treating air, the ozone remover includes catalyst that decomposes ozone.

Disclosed subject matter includes, in yet another aspect, an apparatus for treating air, which includes a housing with an air inlet and an air outlet, the housing enclosing an air treatment zone and an ozone removal zone, wherein the ozone removal zone is positioned downstream of the air treatment zone with respect to a flow direction of the air being treated, an ozone generator in the air treatment zone configured to generate ozone from the air, wherein the ozone generated by the ozone generator treats the air in the air treatment zone, catalyst in the ozone removal zone that removes at least a portion of the ozone generated the ozone generator, a particle matter (PM) filter positioned between the air treatment zone and the ozone removal zone, wherein the ozone generated by the ozone generator treats the PM filter, and an air mover positioned near the air outlet configured to draw the air through the air inlet into the air treatment zone from outside the housing, moving the air through the air treatment zone, the PM filter, and the ozone removal zone, and then emitting the air through the air outlet out of the apparatus.

In some embodiments, in the apparatus for treating air, the ozone generator comprises an ultraviolet (UV) light source, the UV light from the UV light source treats the air in the air treatment zone and the PM filter.

In some embodiments, in the apparatus for treating air, the ozone generator comprises a corona discharge unit.

In some embodiments, in the apparatus for treating air, the PM filter comprises a High Efficiency Particulate Arresting (HEPA) filter.

In some embodiments, in the apparatus for treating air, an interior surface of the housing in the air treatment zone is at least partially coated with a reflector layer.

In some embodiments, in the apparatus for treating air, the interior surface of the housing in the air treatment zone is at least partially coated with aluminum.

In some embodiments, in the apparatus for treating air, the UV light source comprises a first UV lamp generating UV light in the wavelength of about 185 nm.

In some embodiments, in the apparatus for treating air, the UV light source further comprises a second UV lamp generating UV light in the wavelength of about 254 nm.

In some embodiments, the apparatus for treating air further includes a second UV lamp generating UV light in the wavelength of about 254 nm positioned between the PM filter and the ozone removal zone.

In some embodiments, in the apparatus for treating air, the PM filter allows the ozone generated by the ozone generator to penetrate the PM filter to treat both upstream and downstream sides of the PM filter.

In some embodiments, in the apparatus for treating air, the PM filter allows the ozone generated by the ozone generator to penetrate the PM filter to treat an inlet of the ozone removal zone.

In some embodiments, the apparatus for treating air 12 further includes comprising a pre-filter positioned upstream of the PM filter and downstream of the air treatment zone.

In some embodiments, in the apparatus for treating air, the pre-filter comprises a loose weave filter.

In some embodiments, in the apparatus for treating air, the pre-filter is positioned upstream of the air treatment zone.

In some embodiments, the apparatus for treating air further includes a pre-filter positioned upstream of the PM filter and downstream of the air treatment zone, wherein the pre-filter allows the UV light from the UV light source to penetrate the pre-filter to treat the PM filter.

In some embodiments, in the apparatus for treating air, the air mover comprises a volute and a fan, the volute being connected to and upstream of the fan.

In some embodiments, the apparatus for treating air further includes a user interface module configured to receive user input and present information to the user, and an electronic control module configured to set the apparatus to operate in one of a plurality of operation modes, wherein the plurality of operation modes include a regular operation mode, where the ozone generator is on and the air mover operates at a first speed.

In some embodiments, in the apparatus for treating air, the electronic control module is configured to set the apparatus to operate in one of a plurality of operation modes automatically based on at least one of output of at least one sensors and time.

In some embodiments, in the apparatus for treating air, the at least one sensors is placed near the air inlet, near the air outlet, or both.

In some embodiments, in the apparatus for treating air, the at least one sensors detect occupancy of an ambient environment where the apparatus is situated.

In some embodiments, in the apparatus for treating air, the at least one sensors detect contaminant content and level of an ambient environment where the apparatus is situated.

In some embodiments, in the apparatus for treating air, the electronic control module is configured to set the apparatus to operate in one of a plurality of operation modes based on the user input.

In some embodiments, in the apparatus for treating air, the plurality of operation modes further include a self-cleaning mode, where the ozone generator is on, the ozone generated by the ozone generator treats and cleans interior components of the apparatus, and the air mover operates in a second speed lower than the first speed.

In some embodiments, the apparatus for treating air further includes a user interface module configured to receive user input and present information to the user, and an electronic control module configured to set the apparatus to operate in one of a plurality of operation modes, wherein the plurality of operation modes include a regular operation mode, where the ozone generator is on and the air mover operates at a first speed.

In some embodiments, in the apparatus for treating air, the plurality of operation modes further include a self-cleaning mode, where the UV light source is on, the UV light from the UV light source and the ozone generated by the UV light source treat and clean interior components of the apparatus, and the air mover operates in a second speed lower than the first speed.

In some embodiments, in the apparatus for treating air, the UV light source comprises a first UV lamp generating UV light in the wavelength of about 185 nm and a second UV lamp generating UV light in the wavelength of about 254 nm, and the plurality of operation modes further include an ozone removal mode, where the first UV lamp is off and the second UV lamp is on.

In some embodiments, in the apparatus for treating air, the plurality of operation modes further include a particle removal only mode, where the ozone generator is off.

In some embodiments, the apparatus for treating air further includes a wireless communication module configured to communicate with a central management system.

In some embodiments, in the apparatus for treating air, the electronic control module sets the apparatus to operate in one of the plurality of operation modes based on instruction received from the central management system via the wireless communication module.

In some embodiments, in the apparatus for treating air, the instruction is at least partially based on information received from another apparatus for treating air.

In some embodiments, in the apparatus for treating air, at least a portion of the PM filter is made of an UV resistant material.

In some embodiments, in the apparatus for treating air, at least a portion of the PM filter is made of fiberglass.

In some embodiments, in the apparatus for treating air, at least a portion of the PM filter is covered by an UV resistant material.

In some embodiments, the apparatus for treating air further includes an UV light source generating UV light in the wavelength of about 254 nm in the air treatment zone.

Disclosed subject matter includes, in yet another aspect, a computer-readable medium storing instructions that, when executed, cause at least one programmable processor to: communicate with a first air treatment apparatus situated in a first ambient environment and a second air treatment apparatus situated in a second ambient environment, receive from the first air treatment apparatus at least one of information about the first ambient environment and information about a first operating condition of the first air treatment apparatus, select an operation mode for the second air treatment apparatus at least partially based on at least one of the information about the first ambient environment and the information about the first operating condition of the first air treatment apparatus, and transmit the selected operation mode to the second air treatment apparatus.

In some embodiments, in the computer-readable medium, the instructions, when executed, further cause the at least one programmable processor to: receive additional information from an external source, and select the operation mode for the second air treatment apparatus at least partially based on the additional information received.

In some embodiments, in the computer-readable medium, the external source is a remote server, and the additional information includes at least one of weather or air quality information.

Disclosed subject matter includes, in yet another aspect, a computer system for managing air treatment apparatuses in multiple environments, which includes at least one programmable processor, and a computer-readable medium storing instructions that, when executed, cause the at least one programmable processor to perform operations comprising: communicating with a first air treatment apparatus situated in a first ambient environment and a second air treatment apparatus situated in a second ambient environment, receiving from the first air treatment apparatus at least one of information about the first ambient environment and information about a first operating condition of the first air treatment apparatus, selecting an operation mode for the second air treatment apparatus based on at least one of the information about the first ambient environment and the information about the first operating condition of the first air treatment apparatus, and transmitting the selected operation mode to the second air treatment apparatus.

Disclosed subject matter includes, in yet another aspect, a computerized method for managing air treatment apparatuses in multiple environments, which includes communicating with a first air treatment apparatus situated in a first ambient environment and a second air treatment apparatus situated in a second ambient environment, receiving from the first air treatment apparatus at least one of information about the first ambient environment and information about a first operating condition of the first air treatment apparatus, selecting an operation mode for the second air treatment apparatus based on at least one of the information about the first ambient environment and the information about the first operating condition of the first air treatment apparatus, and transmitting the selected operation mode to the second air treatment apparatus.

Disclosed subject matter includes, in yet another aspect, a system for treating air in multiple environments, which includes a plurality of air treatment apparatuses, each of the plurality of the air treatment apparatuses comprising: an user interface module configured to receive user input and present information to the user, at least one sensors, an electronic control module configured to set the apparatus to operate in one of a plurality of operation modes based on at least one of output of the at least one sensors and time, and a wireless communication module configured to communicate with a network, wherein each of the plurality of the air treatment apparatuses being situated in a separate ambient environment, and a central computer system for managing the plurality of air treatment apparatuses, comprising: at least one programmable processor, and a computer-readable medium storing instructions that, when executed, cause the at least one programmable processor to perform operations comprising: communicating with first of the plurality of air treatment apparatuses situated in a first ambient environment and second of the plurality of air treatment apparatuses situated in a second ambient environment, receiving from the first of the plurality of air treatment apparatuses at least one of information about the first ambient environment and information about a first operating condition of the first of the plurality of air treatment apparatuses, selecting an operation mode for the second of the plurality of air treatment apparatuses based on at least one of the information about the first ambient environment and the information about the first operating condition of the first of the plurality of air treatment apparatuses and transmitting the selected operation mode to the second of the plurality of air treatment apparatuses, wherein the electronic control module of the second of the plurality of air treatment apparatuses is configured to set the second of the plurality of air treatment apparatuses to operate in the selected operation mode based on instruction received from the central computer system via the wireless communication module.

In some embodiments, in the system for treating air in multiple environments, the at least one sensors in each of the plurality of air treatment apparatuses detect occupancy of an ambient environment where the each of the plurality of air treatment apparatuses is situated.

In some embodiments, in the system for treating air in multiple environments, the at least one sensors in each of the plurality of air treatment apparatuses detect contaminant level of an ambient environment where the each of the plurality of air treatment apparatuses is situated.

In some embodiments, in the system for treating air in multiple environments, the instructions stored in the computer-readable medium in the central computer system, when executed, further cause the at least one programmable processor to perform operations comprising: receiving additional information from an external source, and selecting the operation mode for the second air treatment apparatus at least partially based on the additional information received.

In some embodiments, in the system for treating air in multiple environments, the external source is a remote server, the additional information includes at least one of weather or air quality information.

Articles of manufacture are also described that comprise computer executable instructions non-transitorily stored on computer readable media, which, when executed by a computer, causes the computer to perform operations herein. Similarly, computer systems are also described that may include a processor and a memory coupled to the processor. The memory may temporarily or permanently store one or more programs that cause the processor to perform one or more of the operations described herein.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 8 is table showing ozone-generating ultraviolet light performance parameters;

FIG. 9 is a table showing ethylene production and sensitivity of selected produce;

FIG. 10 is a table showing conventional ethylene control technologies and corresponding limitations;

FIG. 11 is a graph showing a reduction of ozone using ultraviolet light, according to one embodiment of the subject matter disclosed herein;

FIG. 45C illustrates a partial sectional view of the apparatus for treating air 4500;

Like reference symbols in the various drawings indicate like elements.

DETAILED DESCRIPTION

Throughout this specification and in the claims, the terms air cleaning unit and atmosphere treating unit are intended to relate to an apparatus for sanitizing, decontaminating, deodorizing, conditioning, drying and/or otherwise treating, cleaning, modifying and/or improving an atmosphere within a container.

Figure 1:
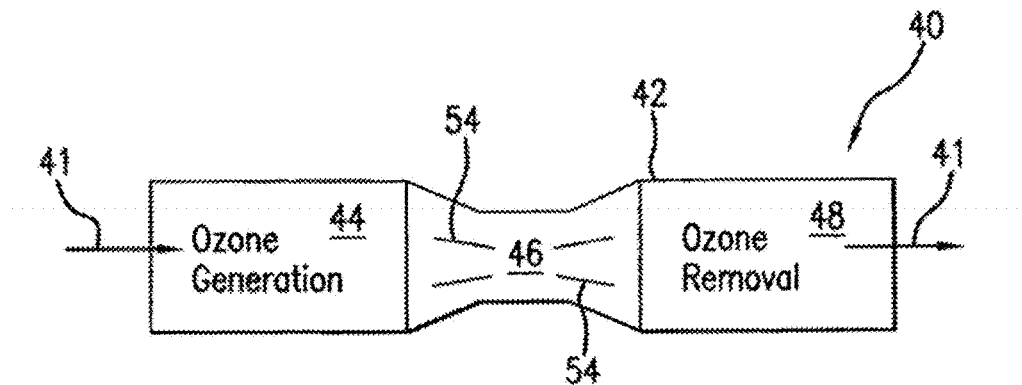
FIG. 1 is a diagrammatic view showing three elements of an air cleaner, including an ozone generation zone, a mixing zone and an ozone dissociation zone, according to one embodiment of the subject matter disclosed herein.
Figure 2:
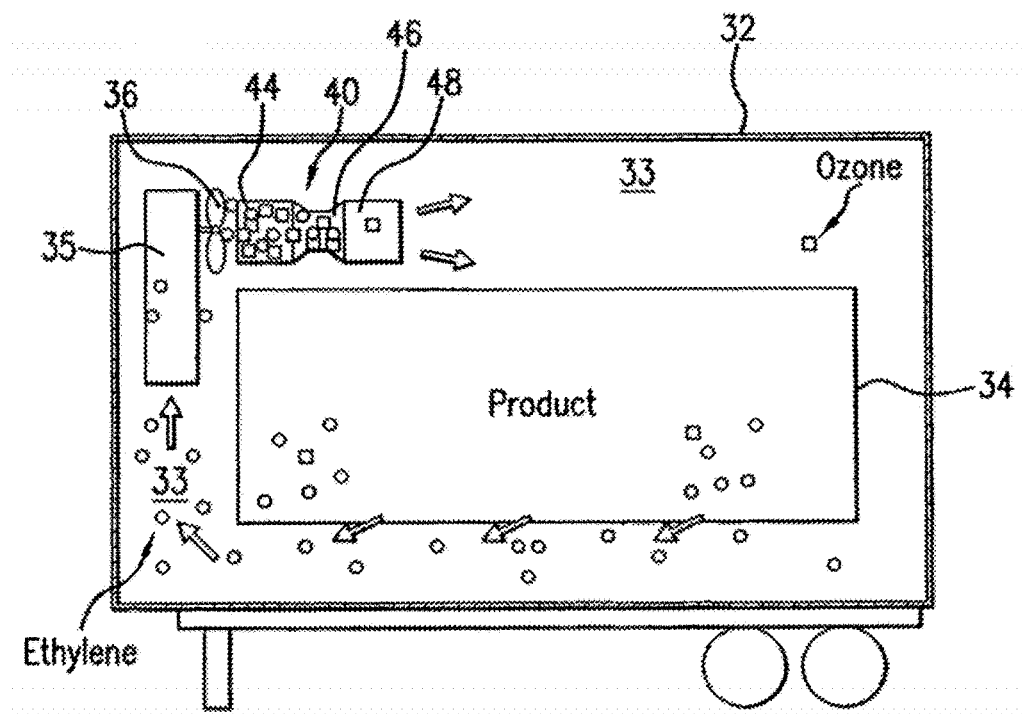
FIG. 2 is a diagrammatic showing of an inside of a container, such as a refrigerated truck trailer, a housing and an evaporator, an air cleaner, and a material or product, according to one embodiment of the subject matter disclosed herein.
Figure 3:
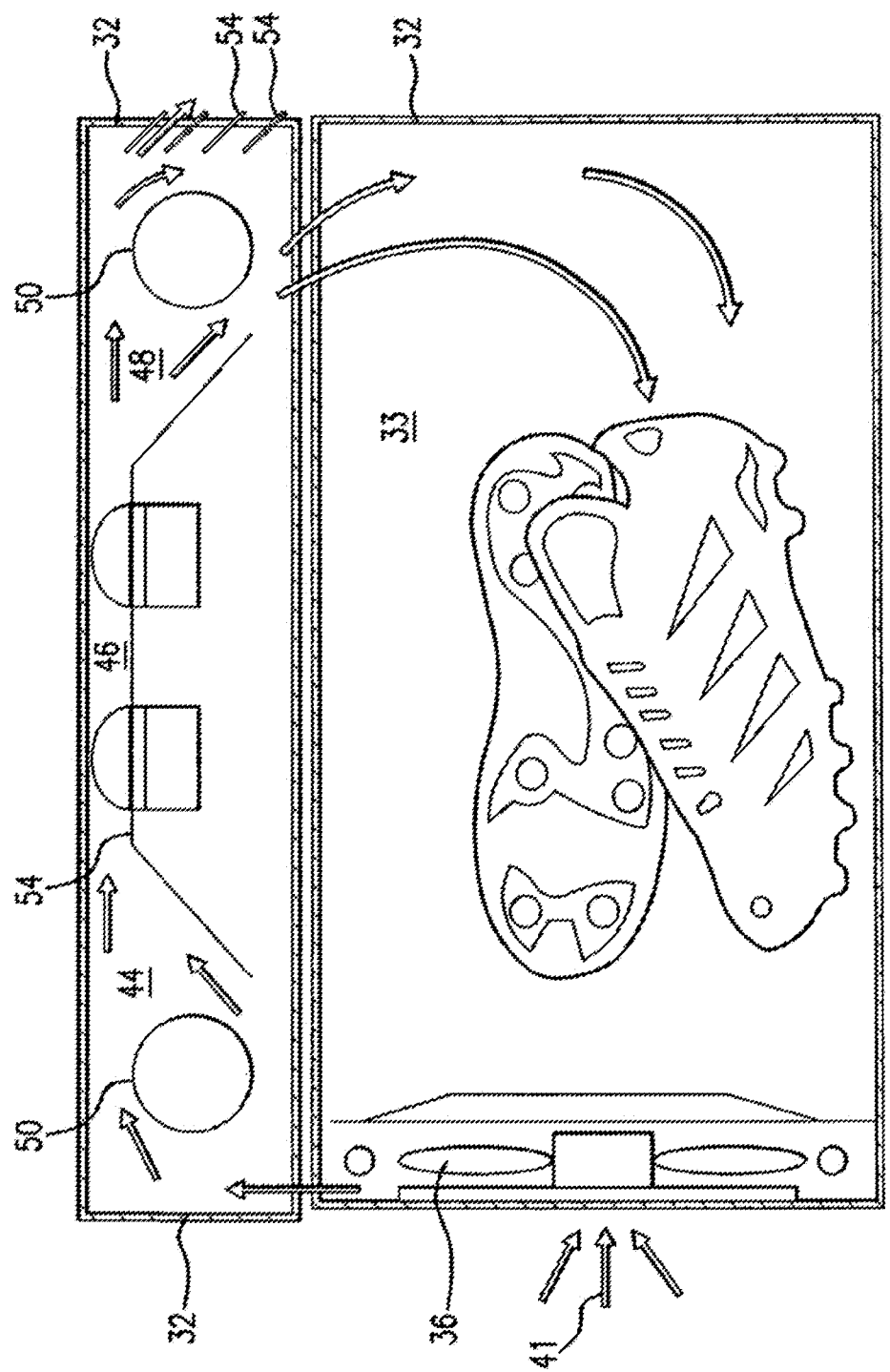
FIG. 3 is a diagrammatic side view of a cylindrical configuration of an air cleaner unit, according to one embodiment of the subject matter disclosed herein.
Figure 4:
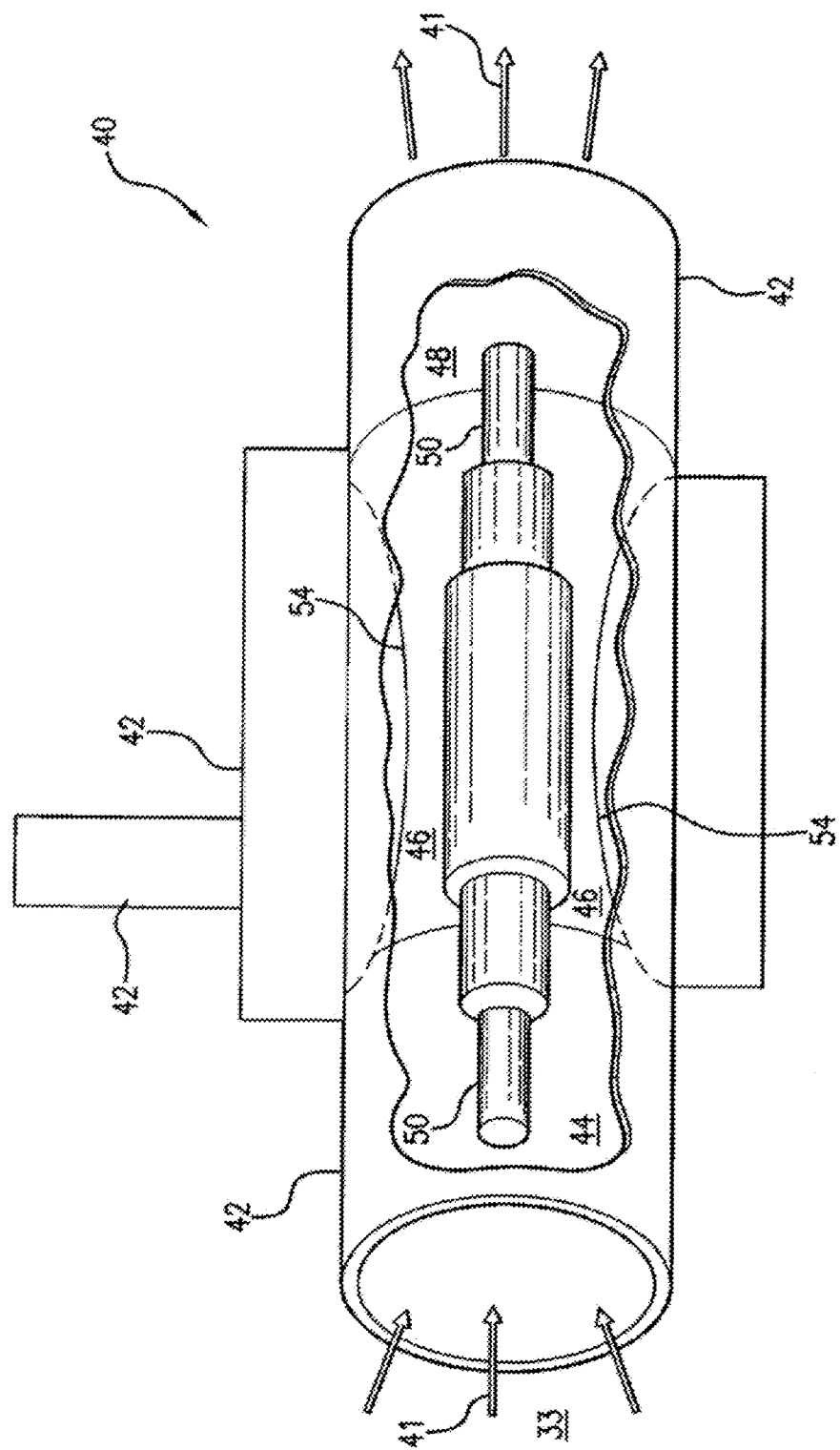
FIG. 4 is a diagrammatic partial sectional view of an air cleaner unit, according to one embodiment of the subject matter disclosed herein.
Figure 5:
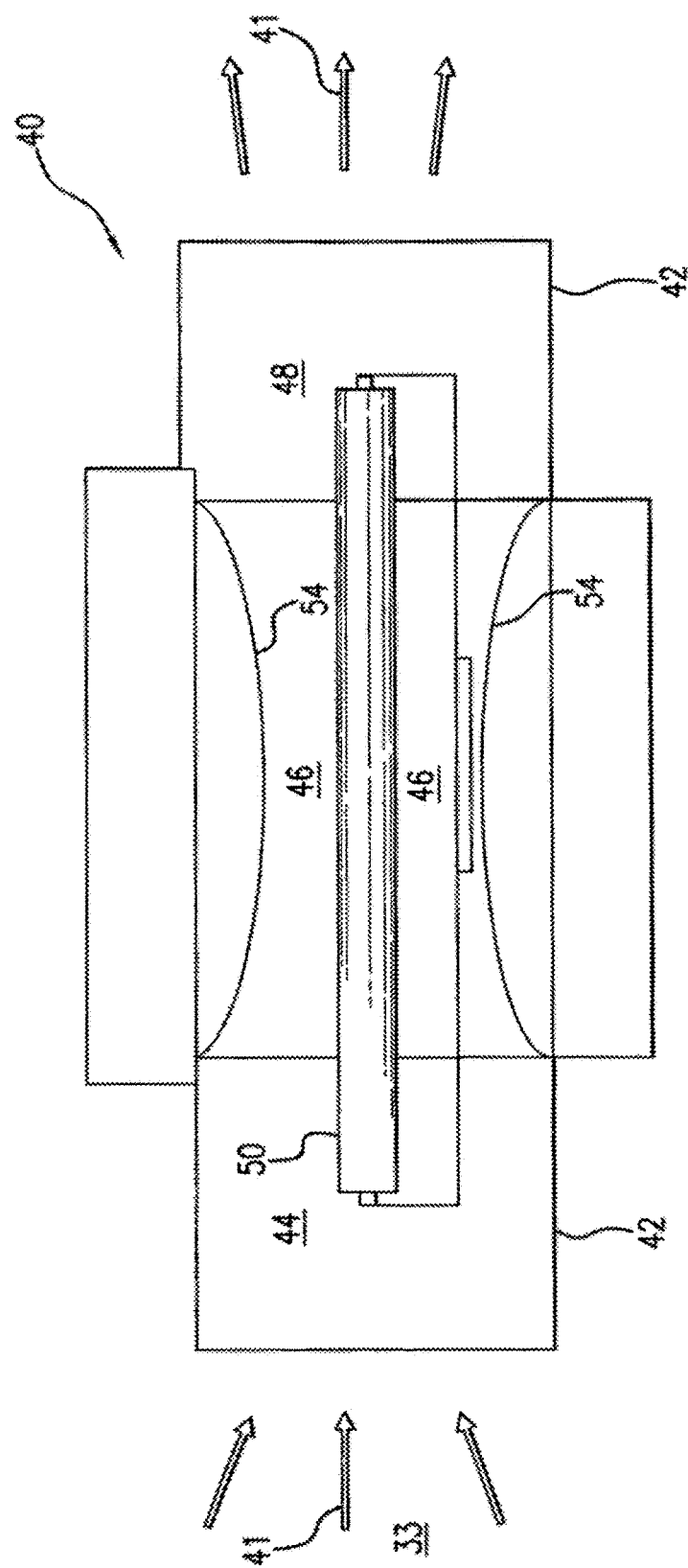
FIG. 5 is a diagrammatic partial sectional view of an air cleaner unit, according to another embodiment of the subject matter disclosed herein.
Figure 6:
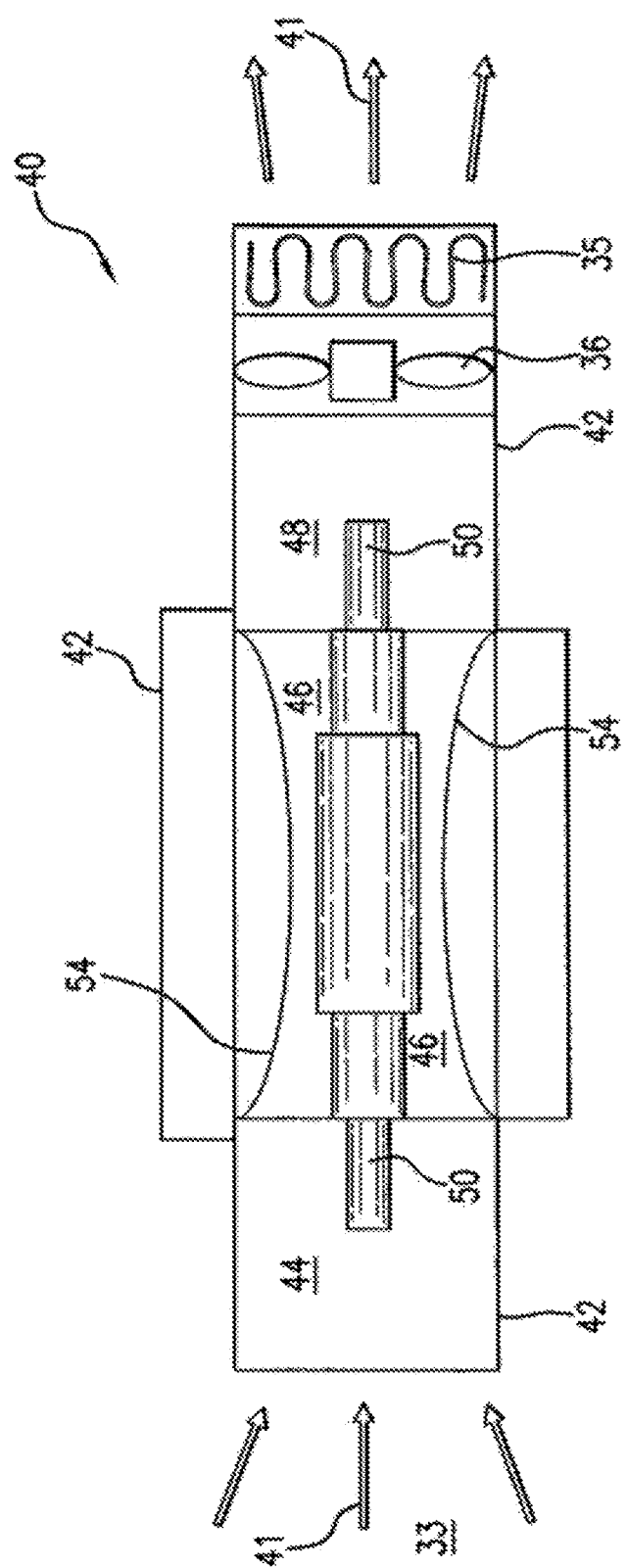
FIG. 6 is a diagrammatic partial sectional view of an air cleaner unit, according to one embodiment of the subject matter disclosed herein.
Figure 7:
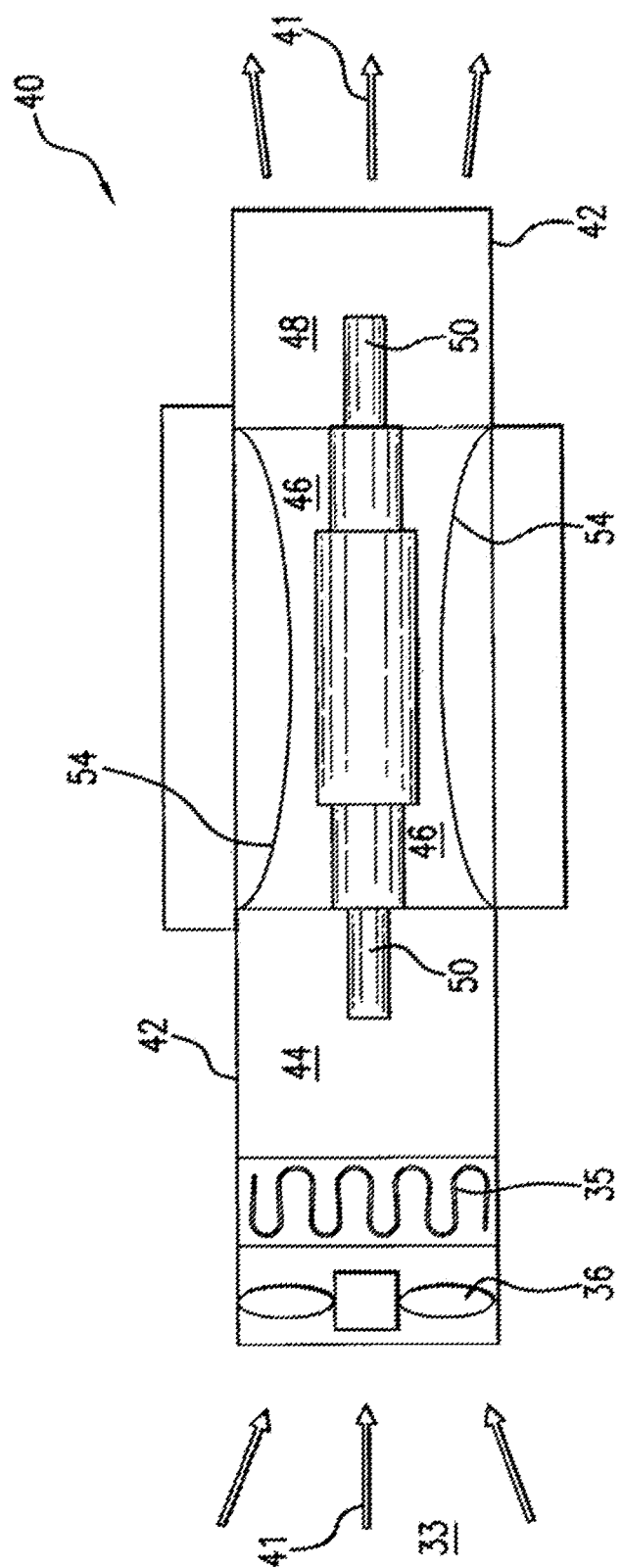
FIG. 7 is a diagrammatic partial section view of an air cleaner unit, according to one embodiment of the subject matter disclosed herein.

FIG. 1 shows air cleaning unit 40, according to one embodiment of the subject matter disclosed herein. FIG. 2 shows air cleaning unit 40 positioned or mounted within container 32, such as a truck trailer, according to one embodiment of the subject matter disclosed herein. FIG. 3 shows air cleaning unit 40 positioned or mounted within a different container 32, according to another embodiment of the subject matter disclosed herein. Container 32 can have any other suitable size, shape and/or environment housed within container 32. For example, in some embodiments of the subject matter disclosed herein, container 32 includes but is not limited to a room, another similar space and/or environment within a residential building space, a commercial building space, an industrial building space and/or a space of any other similar building structure, structural element and/or other structure that forms a space which can or cannot be sealed, ventilated, conditioned and/or otherwise used to contain, hold and/or form an environment, including but not limited to a closed environment and/or a conditioned environment. As used throughout this specification and/or in the claims, the terms "room", "building", "building space", "space" and/or "container" are intended to be interchangeable with each other and to similarly relate to the structure or the structural element that forms or otherwise defines atmosphere 33, for example, as atmosphere 33 is housed and/or otherwise contained by the structure or the structural element.

As shown in FIG. 1, air cleaning unit 40 has structure 42, such as a housing, that forms zone 44, zone 46 and zone 48. As air or another suitable atmosphere passes through air cleaning unit 40, such as shown by the arrows of flow direction 41, in FIG. 1, atmosphere 33 passes first through zone 44, then through zone 46, and then through zone 48.

In certain embodiments according to the subject matter disclosed herein, ozone is generated within atmosphere 33 passing through zone 44.

The generated ozone is mixed with atmosphere 33, through zone 46. As described in greater detail below, in embodiments wherein ethylene is an atmosphere contaminant that is desired to be removed, zone 46 can desirably serve for both ozone mixing and reaction with ethylene.

At least a portion of the generated ozone is removed from the mixed atmosphere, within zone 48. Thus, as the atmosphere discharges from zone 48, the atmosphere has been exposed to generated ozone, mixed with the generated ozone and then disassociated from at least a portion of the generated ozone.

FIGS. 4-7 and 31 each shows a different embodiment of air cleaning unit 40, according to the subject matter disclosed herein. As shown in FIGS. 4-7 and 31, UV source 50 comprises a light bulb with an ultraviolet output and/or a corona discharge device that generates ozone within zone 44. Any other suitable mechanical, electro-mechanical and/or other device can be used to generate ozone within zone 44.

FIGS. 1 and 2 show zone 48 downstream with respect to zone 46, and zone 46 downstream with respect to zone 44. In other embodiments according to the subject matter disclosed herein, zone 46 which is the mixing zone can be at least partially within or part of zone 44 where ozone is generated. In other embodiments according to the subject matter disclosed herein, zone 48 in which ozone is removed can be at least partially within or part of zone 46, in which mixing occurs. In other embodiments according to the subject matter disclosed herein, mixing, such as in zone 46, can occur entirely throughout zones 44 and/or 48.

FIG. 1 shows flow diverter 54 positioned within zone 46. In other embodiments according to the subject matter disclosed herein, flow diverter 54 can be mounted within or exposed to zone 44 and/or zone 48. Flow diverter 54 can be any suitable device that mixes fluid flowing through air cleaning unit 40, including but not limited to a flow nozzle, a baffle, a structure, a mechanical mixer and/or a nozzle, such as a nozzle forming a plurality of flow channels.

As shown in FIGS. 1 and 4-7, for example, mixing can occur by forming a nozzle that has a variable diameter along a flow direction of the atmosphere flowing through air cleaning unit 40. Any suitable venturri nozzle or other converging and/or diverging nozzle can be used to mix the fluid flow.

Figure 12:
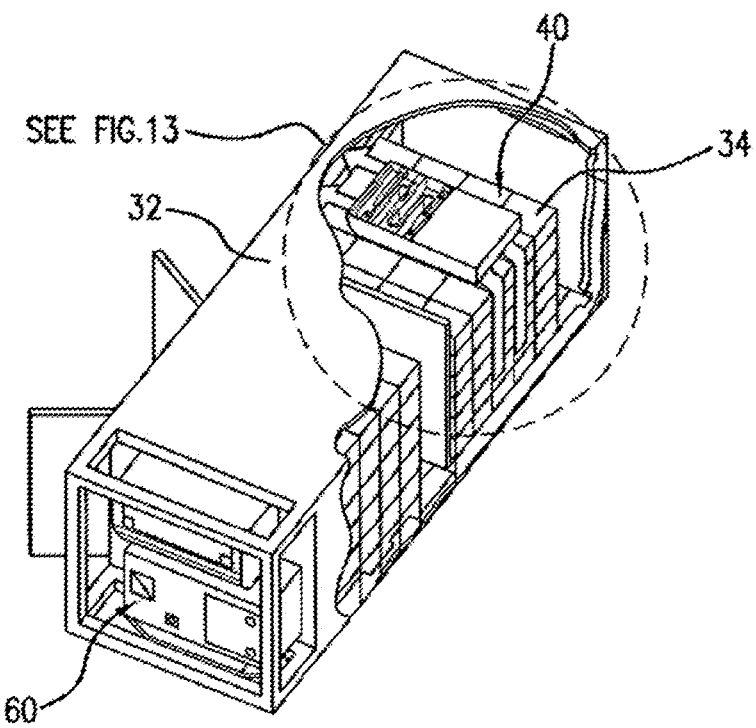
FIG. 12 is a partial cut-away perspective view of an air cleaning unit mounted within a container, according to one embodiment of the subject matter disclosed herein.
Figure 13:
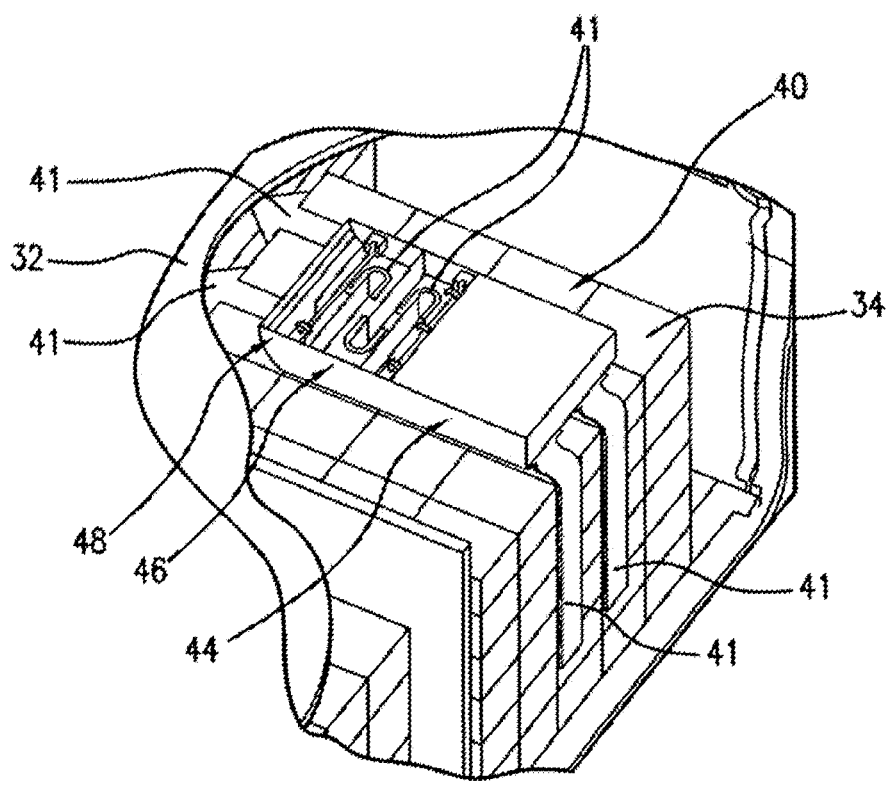
FIG. 13 is an enlarged perspective view showing a partial cut-away section of an air handling unit, according to the embodiment as shown in FIG. 12.

FIGS. 12 and 13 show another embodiment for mixing fluid flowing through air cleaning unit 40. The arrows in FIG. 13 show flow direction 41 along which fluid passes through zone 44, zone 46 and zone 48 of air cleaning unit 40. FIG. 13 shows one particular baffle arrangement. However, any other suitable baffle configuration and design can be used to mix the fluid flow.

Figure 14:
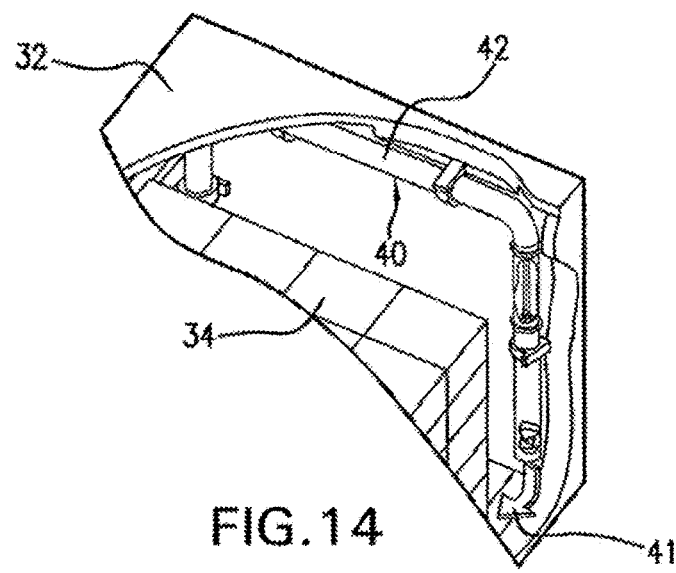
FIG. 14 is a partial cut-away perspective view of an air cleaning unit mounted within a container, according to another embodiment of the subject matter disclosed herein.
Figures 15, 16:
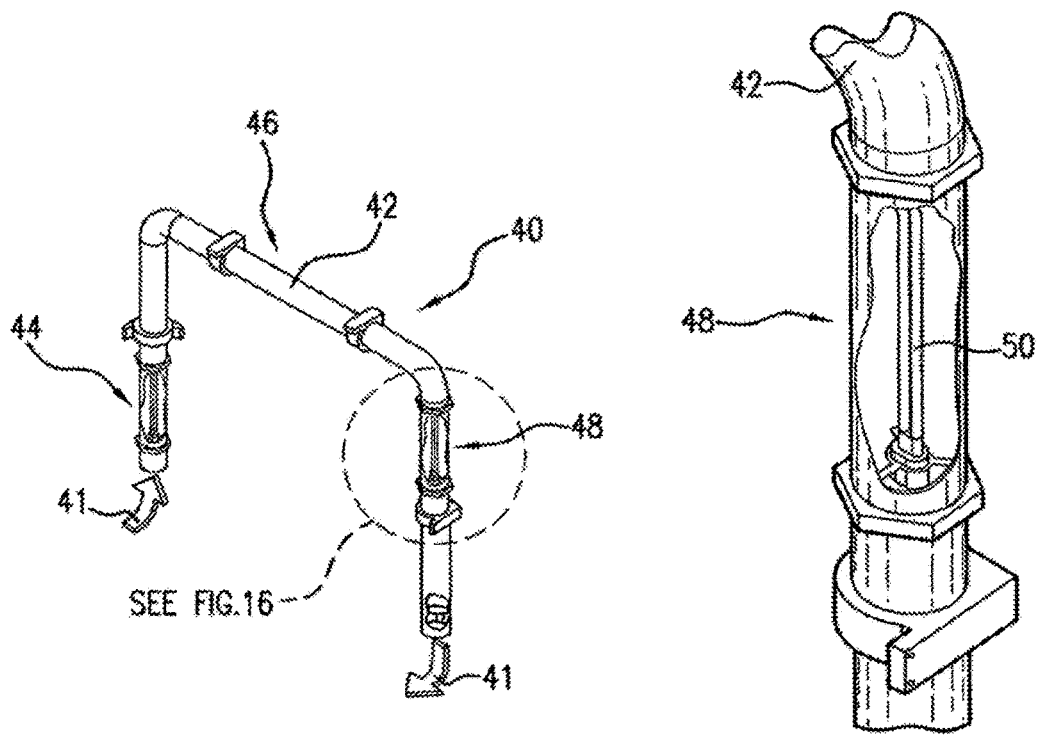
FIG. 15 is a partial cut-away perspective view of an air cleaning unit, according to the embodiment shown in FIG. 14.
FIG. 16 is an exploded partial cut-away perspective view of an ozone removal section, according to one embodiment of the subject matter disclosed herein.

FIGS. 12 and 13 show one embodiment of air cleaning unit 40 positioned within container 32 which stores or houses material 34. FIGS. 14-16 show another embodiment of air cleaning unit 40 according to the subject matter disclosed herein. FIG. 14 shows air cleaning unit 40 mounted within container 32.

FIG. 15 shows structure 42 formed by tubular structural members, for example. Any suitable blower or air moving unit, such as an axial fan and/or a centrifugal blower, can be used to draw fluid into an inlet and discharge fluid through an outlet, for example in flow direction 41 as shown in FIG. 15. Structure 42 as shown in FIGS. 15 and 16 may or may not include flow diverter 54, depending upon the particular intended use and requirements for operation.

FIG. 16 shows UV source 50, for example shown as a light bulb in FIG. 16, that can be used to remove ozone within zone 48. Zone 48 can be positioned as shown in FIG. 15 or in any other suitable position for accomplishing ozone removal or reduction.

Figure 31:
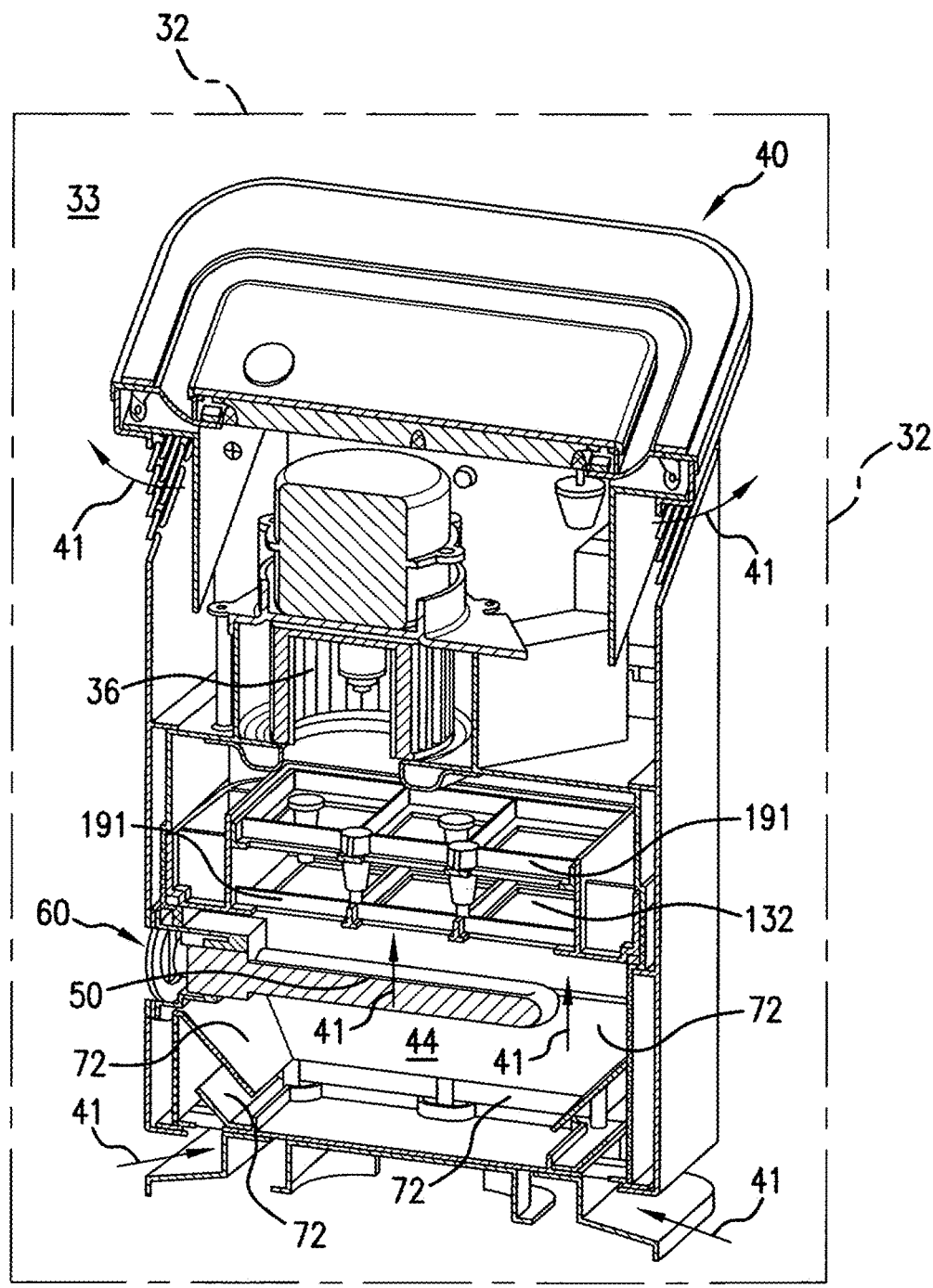
FIG. 31 is a diagrammatic showing a cross section of an air cleaner located inside of a container, such as a room, another similar space and/or environment within a residential building space, a commercial building space, an industrial building space and/or a space of any other similar building structure, structural element and/or other structure that forms a space, according to still another embodiment of the subject matter disclosed herein.
Figure 32:
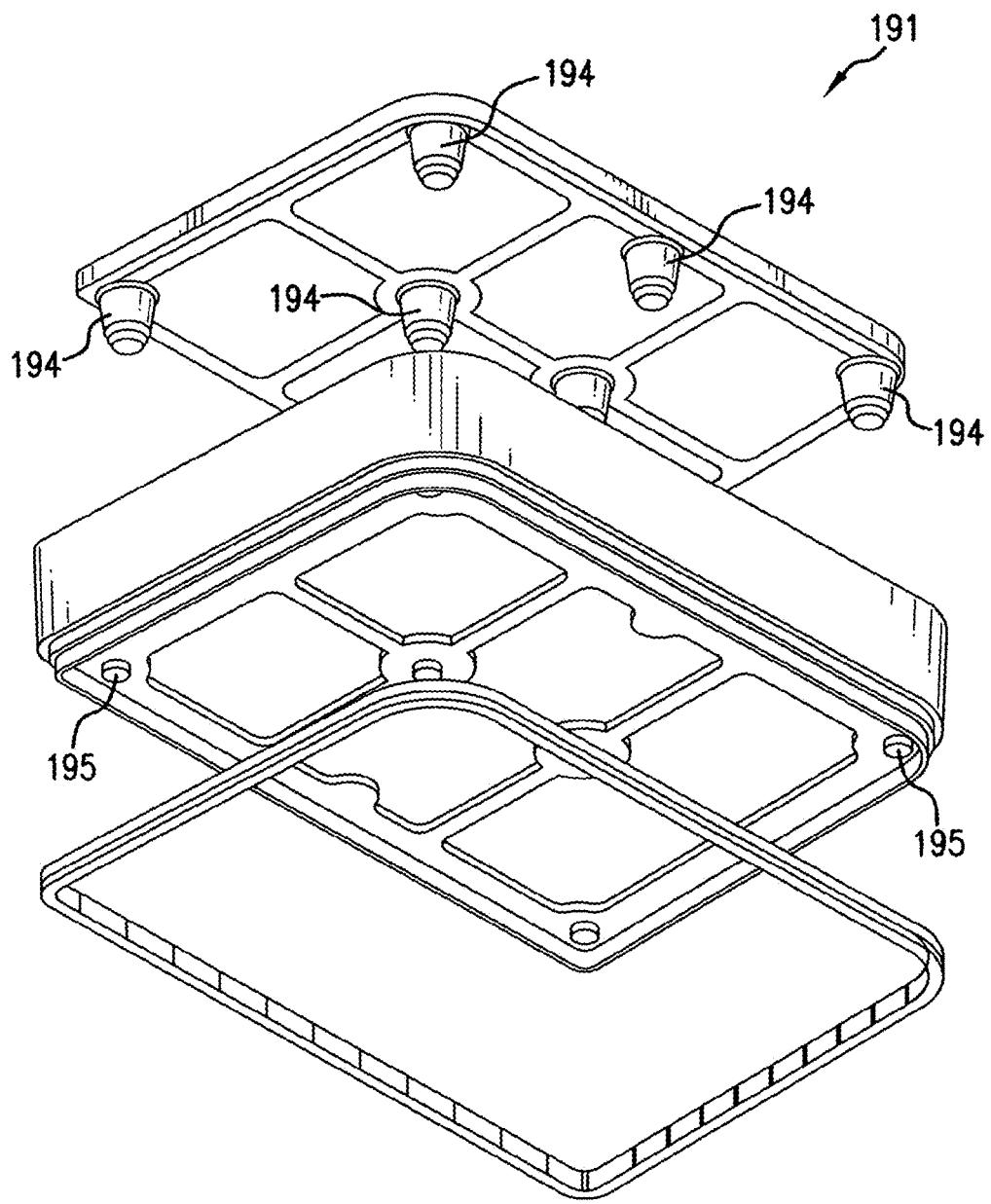
FIG. 32 is an exploded perspective view of a bed structure, according to one embodiment of the subject matter disclosed herein.
Figure 34:
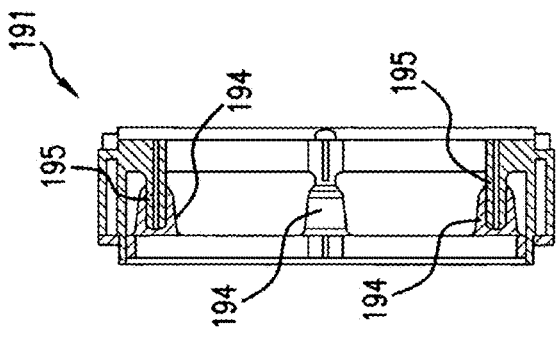
FIG. 34 is a side cross-sectional view of the bed structure, as shown in FIG. 32.
Figure 33:
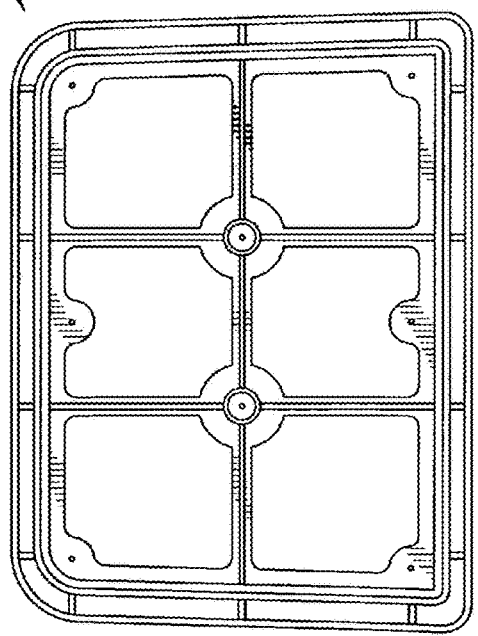
FIG. 33 is a bottom view of the bed structure, as shown in FIG. 32.
Figure 35:
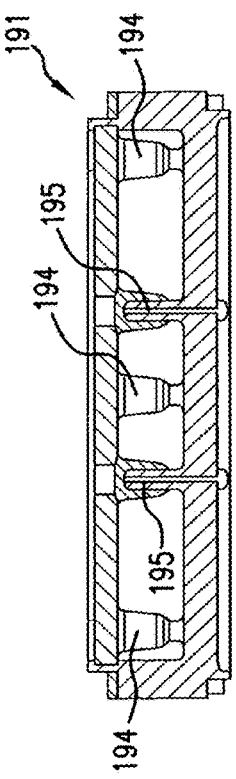
FIG. 35 is a front cross-sectional view of the bed structure, as shown in FIG. 32.
Figure 36:
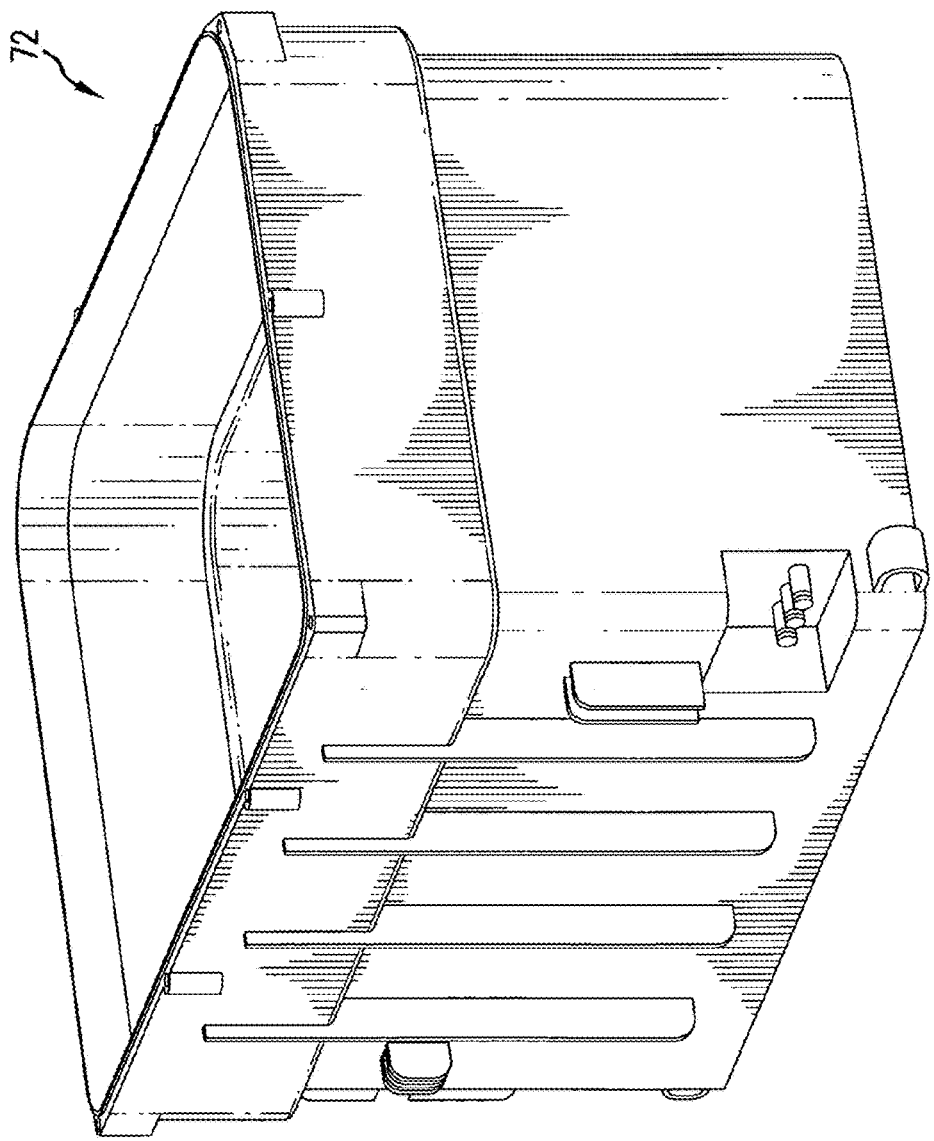
FIG. 36 is a perspective view of a baffle structure having an upper baffle and a lower baffle, according to one embodiment of the subject matter disclosed herein.
Figure 37:
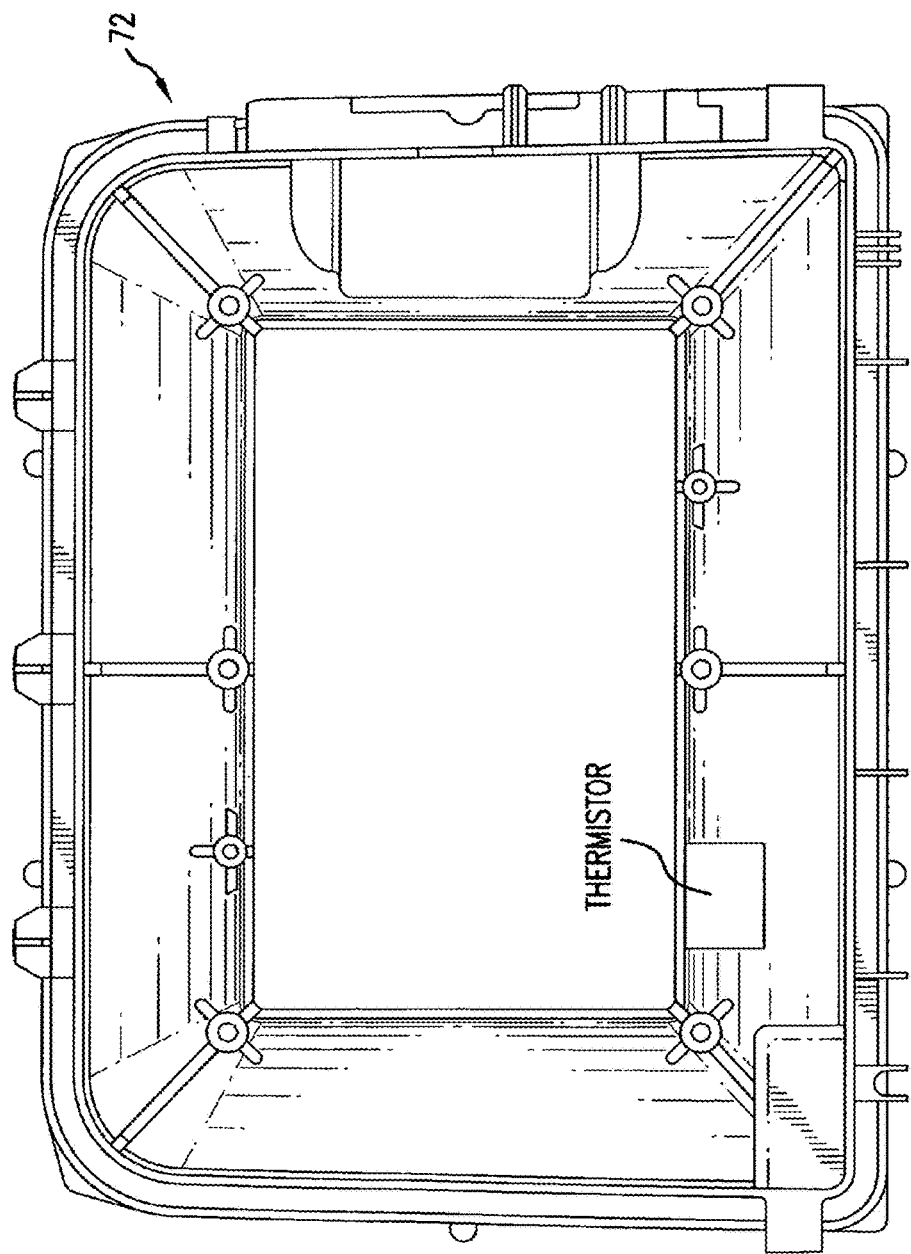
FIG. 37 is a top view of a baffle structure having an upper baffle and a lower baffle, with a thermistor flow sensor board mounted with respect to the baffle structure, according to one embodiment of the subject matter disclosed herein.
Figure 38:
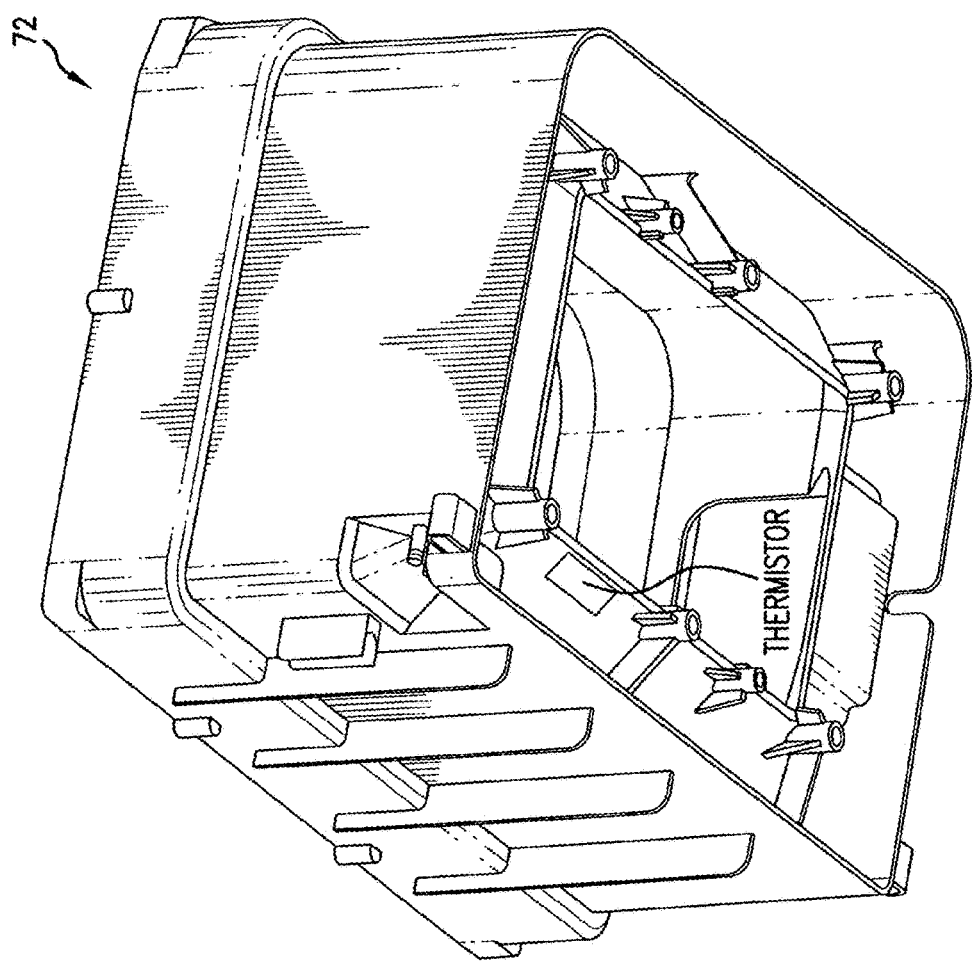
FIG. 38 is a perspective view of a baffle structure showing an upper baffle, with a thermistor flow sensor board mounted with respect to the baffle structure, according to one embodiment of the subject matter disclosed herein.
Figure 39:
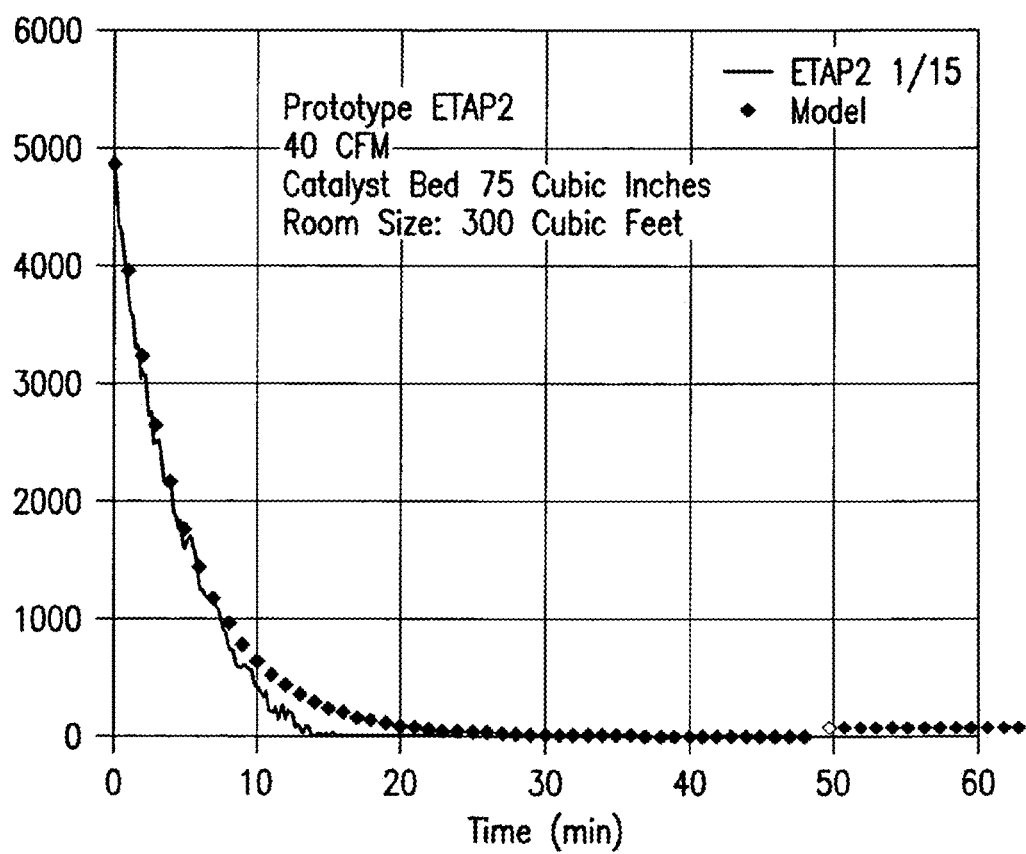
FIG. 39 is a graph showing removal of ethanol over time with the air purifier or the air cleaning unit operating in a closed room of 300 cubic feet in volume, where the solid line is a measured level of ethanol in the room, the dotted line is a model of ethanol removal based on the flow rate through the air purifier or the air cleaning unit, the volume of the room, and the conversion rate of the ethanol, according to one embodiment of the subject matter disclosed herein.
Figure 40:
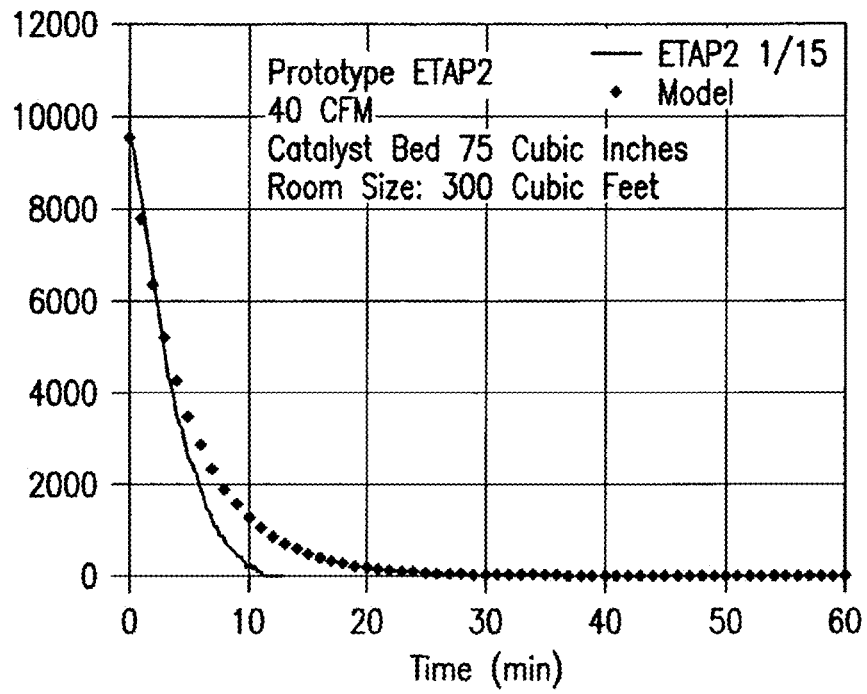
FIG. 40 is a graph showing removal of ammonia over time with the same air cleaner, the same air purifier and/or the same air cleaning unit in the room, according to one embodiment of the subject matter disclosed herein.
Figure 41:
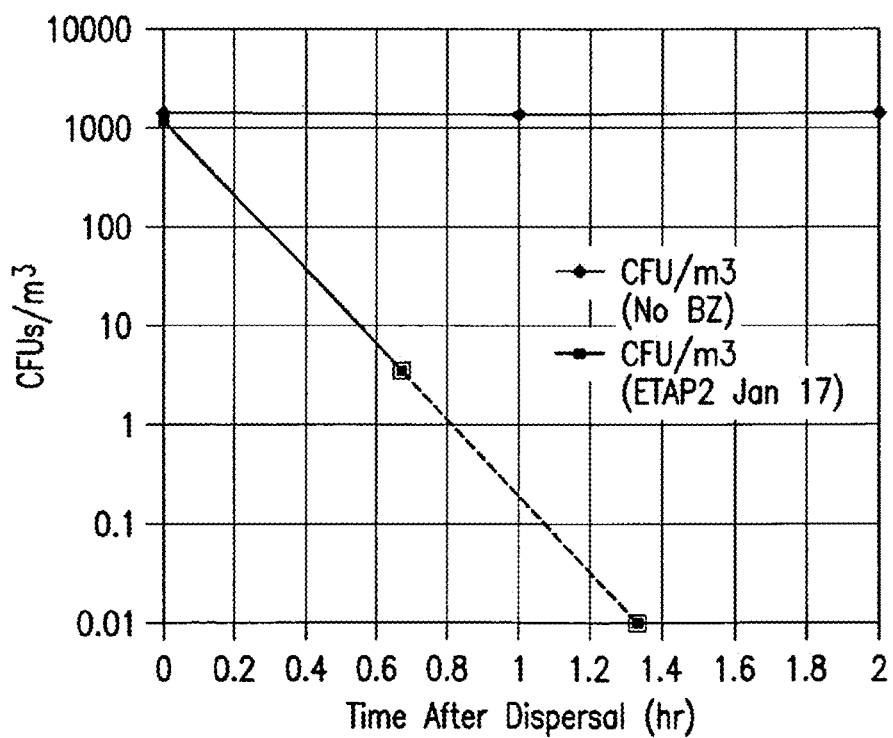
FIG. 41 is a graph showing an inactivation of mold spores over time with the air cleaner, the air purifier and/or the air cleaning unit in the room, according to one embodiment of the subject matter disclosed herein.

Air cleaning unit 40 can be constructed with structure 42 as described in this specification and/or with any other suitable structure that can house or form any zone or chamber used to accomplish ozone generation, mixing and/or ozone removal. FIG. 31 shows still another embodiment of air cleaning unit 40, according to the subject matter disclosed herein, that further comprises catalyst bed 132 which is further described below in this specification.

As shown in FIGS. 12-16, structure 42 can be or form an independent apparatus or system that can be positioned within container 32 and/or exposed to atmosphere 33. With an independent arrangement or a stand-alone arrangement of air cleaning unit 40, it is possible to operate air cleaning unit 40 independently of any existing air conditioner 35. For example, an independent system can accommodate flow rates passing through air cleaning unit 40 which are different than flow rates passing through air conditioner 35, such as an existing refrigeration unit mounted within a transport trailer or other container.

Any suitable conventional device for removing ozone can be mounted within or exposed to zone 48. In certain embodiments according to the subject matter disclosed herein, ozone can be removed or disassociated from zone 48 with a thermal decomposer, a combustible support, a catalytic decomposer (for example, a low temperature ozone destruction catalyst configured as a metal honeycomb monolith, a ceramic honeycomb monolith, or a corrugated metal oxide structure, CARULITE® 200, manganese dioxide/copper oxide catalyst, and/or activated carbon), a photo-disassociating device and/or an ultraviolet light source.

In certain embodiments according to the subject matter disclosed herein, the UV light is generated at a wavelength of about 185 nm to absorb oxygen and thus produce ozone, such as within zone 44. In certain embodiments according to the subject matter disclosed herein, the UV light is generated at a wavelength of about 254 nm to absorb the ozone and cause photolysis or photo-disassociation. FIG. 11 is a graph showing ozone reduction with ultraviolet light at about 254 nm.

Figure 17:
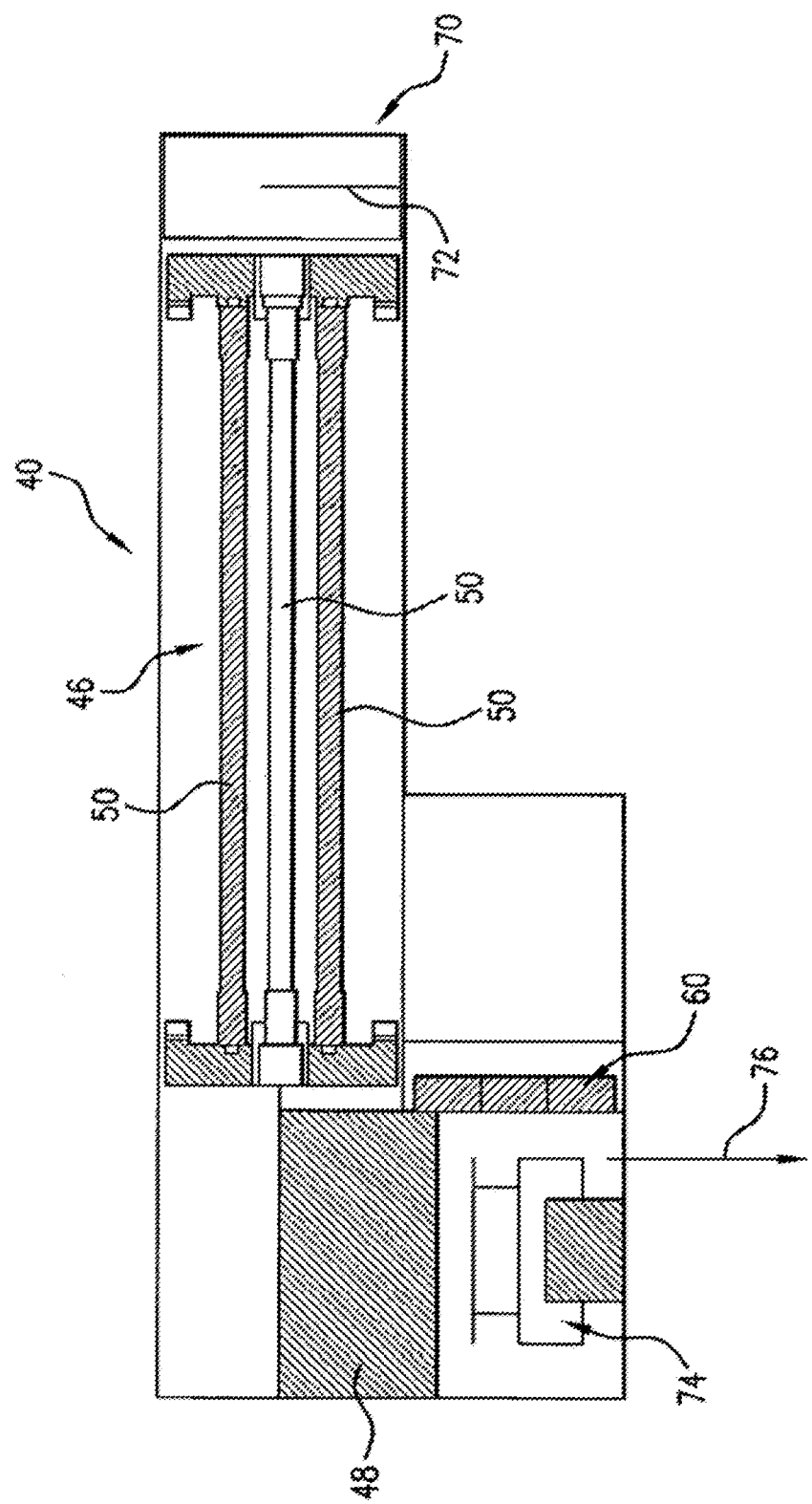
FIG. 17 is a simplified sectional side view of an atmosphere treatment assembly, according to another embodiment of the subject matter disclosed herein.
Figure 18:
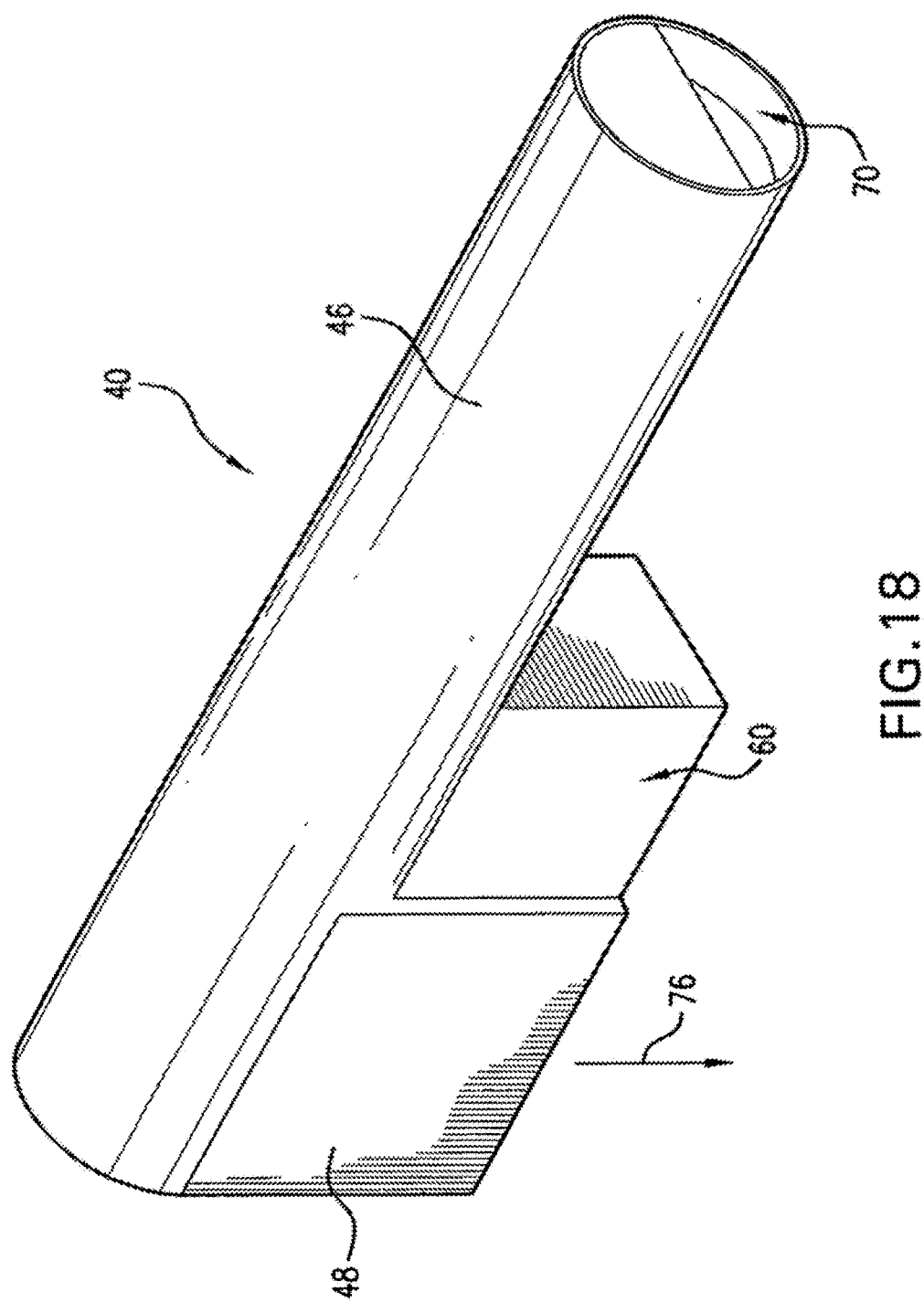
FIG. 18 is a simplified perspective view of the atmosphere treatment assembly shown in FIG. 17.

FIGS. 17 and 18 illustrate a more compact version of an atmosphere treating unit 40 in accordance with one embodiment. In this configuration, air or another suitable selected atmosphere enters via inlet 70 and passes around light baffles 72 and through unit 40. Four UV bulbs 50 (three of which are visible in FIG. 17) are located in zone 46 where ozone is generated and ethylene is rapidly destroyed in the presence of UV light. Ozone is removed through the catalytic decomposer in zone 48. A fan pulls the atmosphere through unit 40. Controls 60 are provided and can communicate or transmit signals through a wired and/or a wireless connection to control any operating parameter and/or function of unit 40. The overall volume of this atmosphere treating/air cleaning unit is less than 1 cubic foot.

As will be appreciated by those skilled in the art and guided by the teachings herein provided, light baffles or other suitable design features can desirably be incorporated into atmosphere treating units to minimize and/or avoid exposure to UV light external to the unit.

Figure 19:
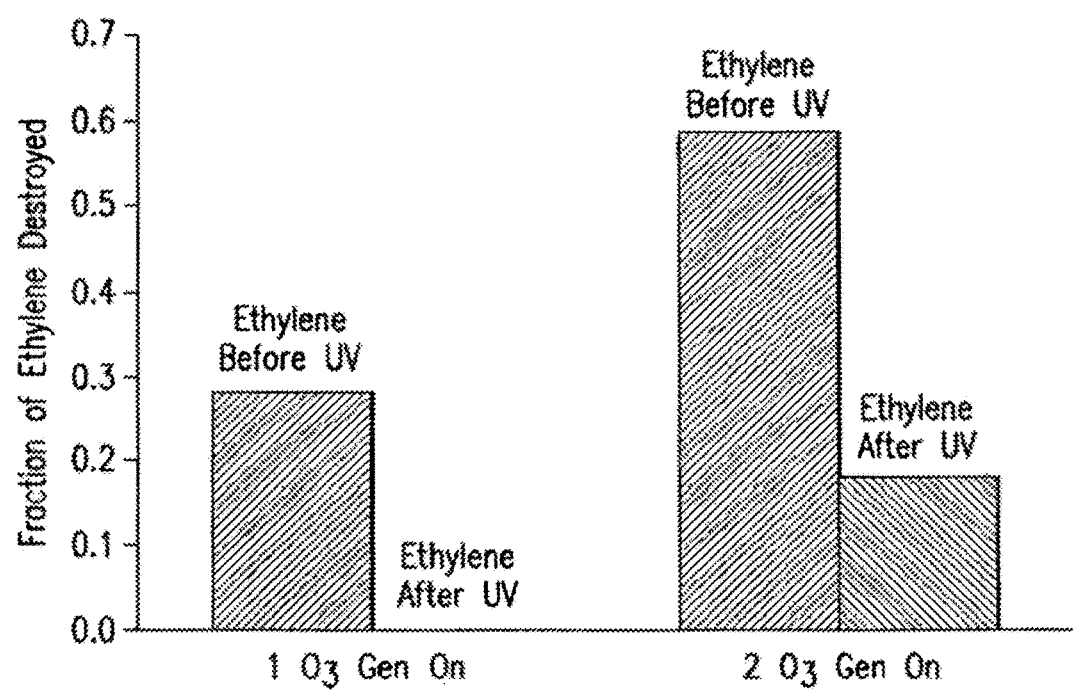
FIG. 19 is a chart showing that UV light exposure in the reaction zone significantly improves performance, e.g., enhances the reaction rate of ozone and ethylene, according to an embodiment of the subject matter disclosed herein.

The destruction of ethylene is greatly enhanced in a configuration in which the ozone is oxidizing the ethylene in the presence of UV light. An experiment was conducted in which UV bulbs were used to generate ozone. In one test, the ethylene was added to the system upstream of the UV lights so that the ethylene would mix with the ozone laden air in the presence of the UV bulbs. In a second test, the ethylene was added to the system downstream of the UV bulbs so that there was no view factor of the reacting gases and the UV light itself. This experiment was conducted twice: once with one UV bulb energized and again with two UV bulbs energized. FIG. 19 shows the difference in ethylene destruction rate between these two test conditions. With one UV bulb energized, the fraction of ethylene destroyed was over 25% in the presence of UV light and almost 0% without the light present. With two UV bulbs energized, the fraction of ethylene destroyed was about 60% in the presence of UV light and less than 20% without the UV light enhancing the reaction rate. This experiment demonstrates that the presence of UV light significantly enhances the reaction rate of ozone and ethylene.

As shown in FIGS. 2 and 3, for example, an outlet of structure 42 which forms air cleaning unit 40 is in communication with zone 48 and atmosphere 33 or the space of container 32. As shown in FIGS. 2 and 3, material 34 is mounted, positioned or otherwise housed within container 32 so that material 34 is exposed to atmosphere 33.

Also shown in FIGS. 2, 3 and 31, air mover 36 can be used to circulate atmosphere 33. Any suitable fan or other air moving device can be used to create flow of atmosphere 33 through air cleaning unit 40. As shown in FIG. 2, air conditioner 35, such as an evaporator or any other suitable air conditioning device, is mounted within atmosphere 33 of container 32.

Container 32 can comprise any suitable structure that defines a chamber or other suitable space for accommodating material 34. Container 32 can be formed by a transportation trailer, a storage trailer, a storage bin, a bag, a shipping container, an equipment bin and/or an expandable structure. In other embodiments of the subject matter disclosed herein, container 32 comprises or consists of a room of a building, a building structure and/or any other suitable structure that contains, houses, has and/or forms a space or other similar environment within a residential building, a commercial building, an industrial building and/or any other similar building structure or other structure that forms a space and/or an environment that is or is not sealed, ventilated, conditioned and/or otherwise environmentally controlled.

In certain embodiments according to the subject matter disclosed herein, the method for sanitizing, decontaminating, deodorizing, conditioning, drying or otherwise treating atmosphere 33 begins with generating ozone within atmosphere 33 passing through zone 44. Within zone 46, the generated ozone is mixed with the atmosphere 33 to enhance removal of undesirable contaminates or other elements of atmosphere 33. At least a portion and possibly the entire amount of generated ozone is removed from the mixed atmosphere 33 as it passes through zone 48.

It is possible to mix atmosphere 33 with the generated ozone within zone 44 and/or zone 46. It is possible to continue to mix atmosphere 33 with the generated ozone as it passes through zone 48.

The apparatus of the subject matter disclosed herein can comprise a control unit, for example located at the exit of the evaporator. The control unit can comprise three sections, including a UV-light (185 nm) ozone generation chamber for generating a relatively high ozone concentration, a mixing zone for removing ethylene with ozone, and a UV-light (254 nm) ozone dissociation chamber for destroying ozone to a level desired for the atmosphere in the container.

The apparatus and/or the method of the subject matter disclosed herein can comprise a controller or other suitable control system for managing or controlling ozone generation, mixing and/or ozone removal.

In some embodiments of the subject matter disclosed herein, a controller, such as control 60 as shown in FIGS. 17 and 18, can communicate or transmit signals through a wired and/or a wireless connection to control any operating parameter and/or function of air cleaning unit 40. In some embodiments of the subject matter disclosed herein, control parameters are based on timing functions of one or more UV sources 50. It is possible to control the apparatus and/or the method to achieve desired results without requiring, for example, a relatively expensive ethylene sensor and/or a feedback loop. Any control based on timing functions of UV source 50, according to the subject matter disclosed herein, can be relatively inexpensive and will require reduced maintenance and reduced replacement parts, particularly as compared to a sensor-based control system.

In certain embodiments of the subject matter disclosed herein, the controller can comprise a transport and storage mode and/or a cleaning mode. In the transport and storage mode, air cleaning unit 40 can cycle with an evaporator. When an evaporator air handler operates, two sets of UV sources 50 can be energized to remove any residual ethylene from atmosphere 33. An override mode can start air mover 36 or any other suitable air handler, for example to begin moving air through the evaporator and/or air cleaning unit 40, for a defined or chosen time period. The controller can then trigger the air handler to start and begin passing fluid through air cleaning unit 40, even if a thermostat or other sensor does not request or call for the evaporator to start.

In certain embodiments of the subject matter disclosed herein, during the cleaning mode, container 32 can be closed, with or without a lock and/or an alarm, during a cleaning cycle. During the cleaning cycle, UV source 50 or another suitable ozone generator can be energized while fluid passes through air cleaning unit 40, such as for any preset and/or calculated time period. After a defined or calculated time period for generating ozone is reached, UV source 50 can be stopped or not operated while air is circulated through air cleaning unit 40, for example for a time that is sufficient to expose atmosphere 33 and thus kill or remove molds, fungus, spores and/or any other undesired contaminate. Any necessary time period can be calculated from a program of the controller and/or from known data. After the defined and/or calculated time period, UV source 50 can be started within zone 48 to remove ozone from the fluid flowing through air cleaning unit 40. This same function can be achieved with the use of a catalytic decomposer as an alternative to the UV source 50 in zone 48. With the use of a catalytic decomposer to destroy the ozone in zone 48, the cleaning cycle would utilize a bypass of zone 48 during the cleaning mode that would allow ozone build-up in the storage container. After the defined and/or calculated cleaning period, the bypass would be closed and UV light 50 in zone 44 would be turned off. The circulation of atmosphere through the catalytic decomposer in zone 48 would clean the atmosphere in storage container of ozone.

After the cleaning cycle time period expires, the controller can signal and/or activate to open any lock and/or to deactivate any alarm. The controller can also be used to communicate with and learn information from any suitable sensor that detects a desired parameter or when the ozone concentration is at a certain level, such as when the ozone concentration falls below a level defined by any government agency and/or other guideline recommendation.

According to the subject matter disclosed herein, a test facility to conduct ozone generation, ethylene removal and ozone destruction testing can include the following components: instrumentation, including a Thermo Fisher 49i ozone analyzer, a storage control systems electro-chemical ethylene analyzer, voltage and/or current meters to monitor a power draw of lamps or UV source 50; an ozone generator, including a UV lamp G24T6VH/U ozone generator (180 nm wavelength, 25 Watts, 2.3 grams/hour output); an ozone remover, including a UV lamp G24T6/U germicidal lamp (254 nm wavelength, 25 Watts, 8.5 Watts UV output); and a stainless steel model container and flow system, including a container sized at ⅛ scale, flow rates scaled to achieve up to 1 air change per minute, an axial fan positioned in a duct to move air through zones 44, 46 and 48, and high vacuum stainless steel weld fittings to provide leak-free operation.

Figure 20:
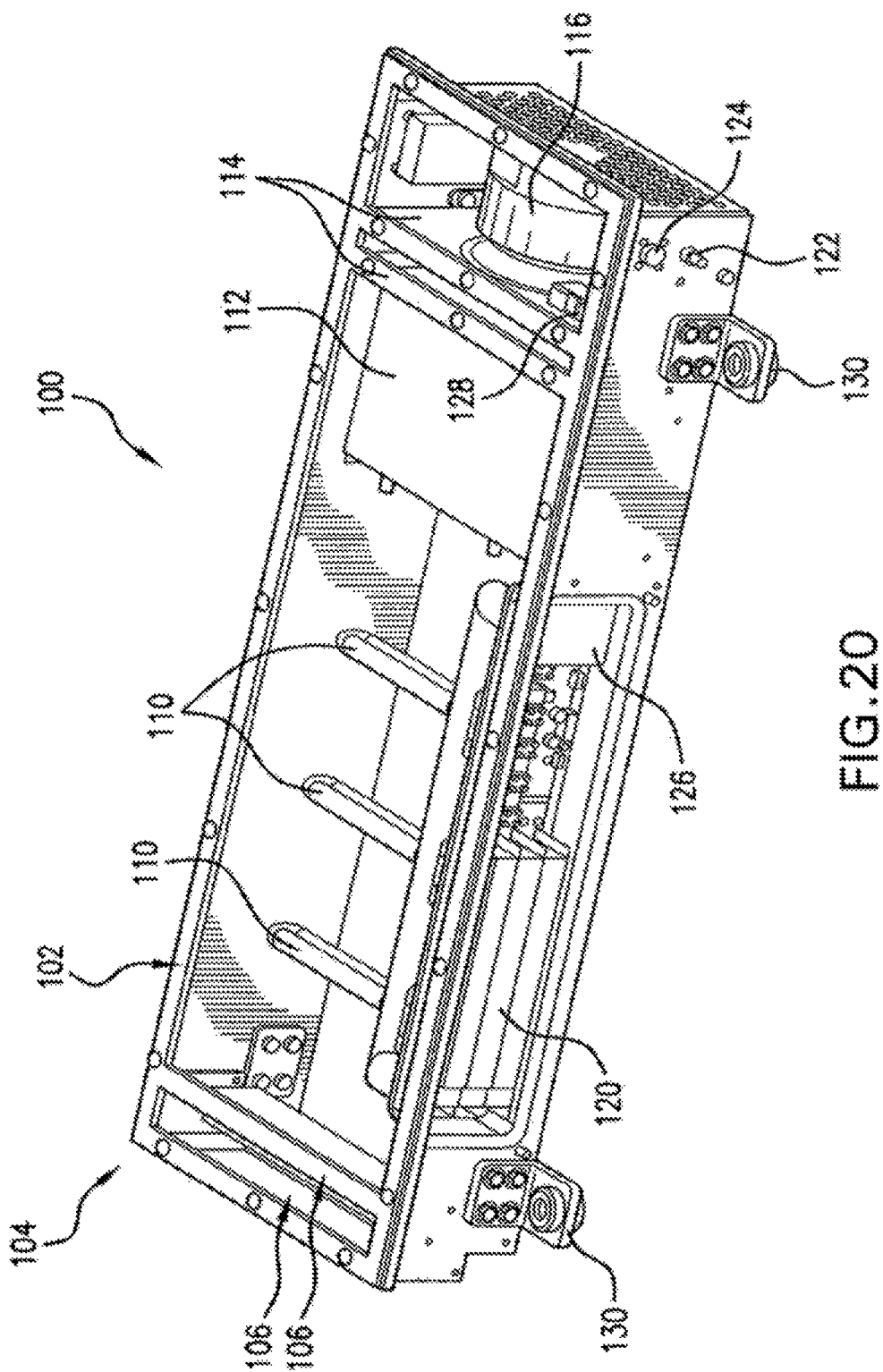
FIG. 20 is a simplified schematic view showing elements of an assembly in accordance with one aspect of the subject matter disclosed herein.
Figure 21:
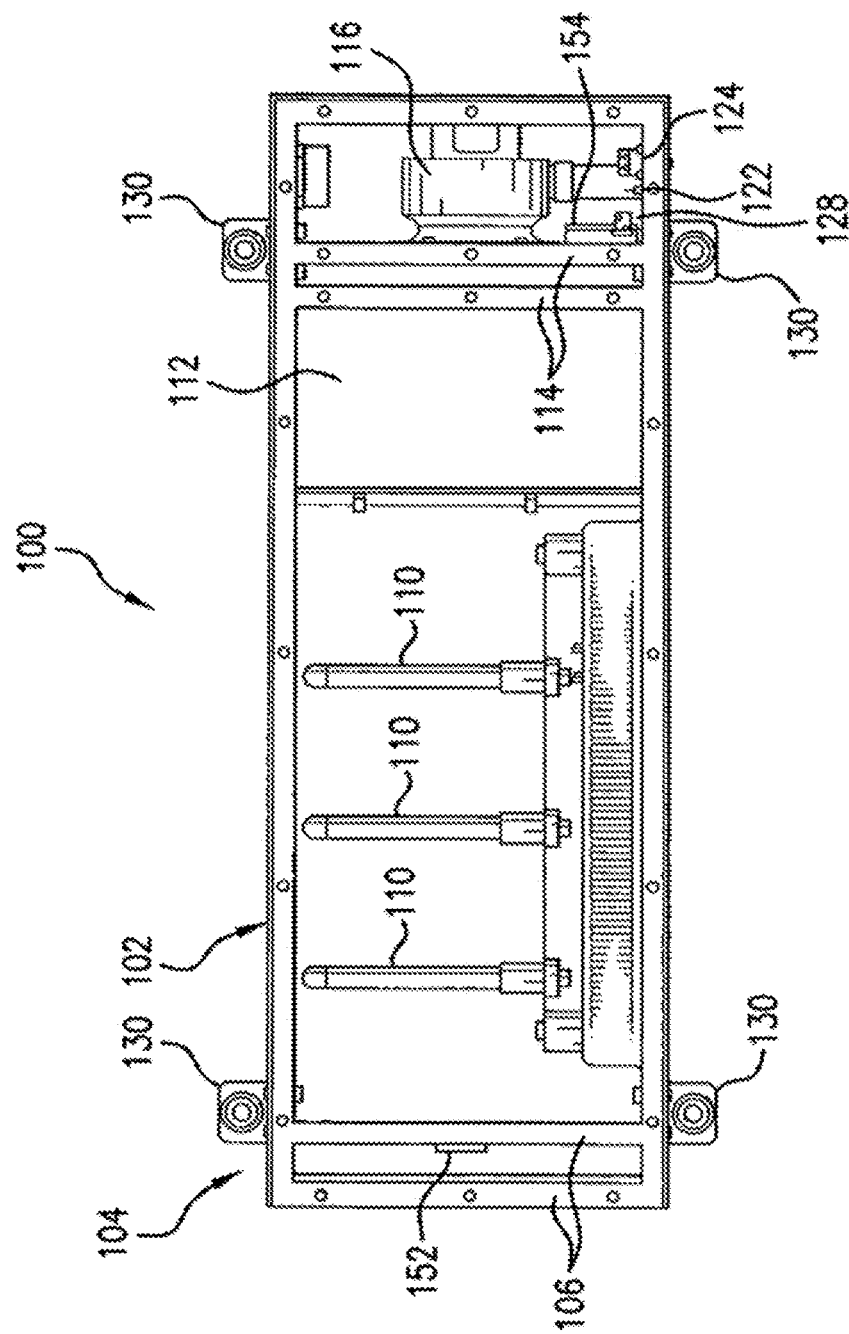
FIG. 21 is a top view of the assembly shown in FIG. 20, showing two possible locations of an ozone fuse in accordance with one aspect of the subject matter disclosed herein.
Figure 22:
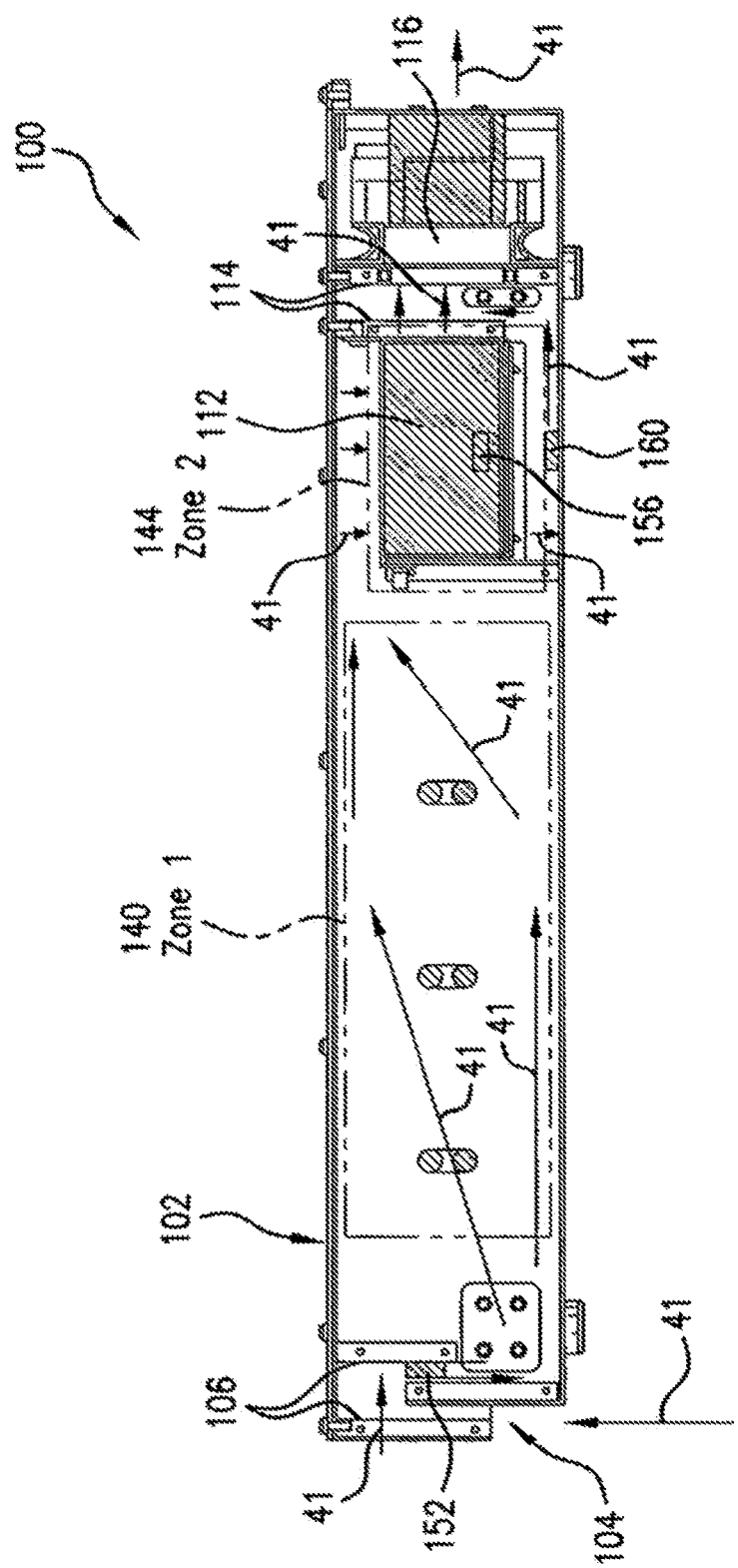
FIG. 22 is a side view with a cut-away of the assembly shown in FIG. 20, indicating three possible locations for an ozone fuse in accordance with one aspect of the subject matter disclosed herein.

Turning now to FIGS. 20-22 there is illustrated assembly 100 and, in particular, atmosphere treating unit structure 102 in accordance with one aspect of the subject matter disclosed herein. Atmosphere treating unit structure 102 includes: air inlet 104; light baffles 106 (to ensure that no viewing angle would result in external exposure to UV light); UV light bulbs 110 that generate ozone; catalytic ozone destruction bed 112; a set of flow baffles 114 and fan 116 to pull air through structure 102; and various control elements useful in the operation of assembly 100, including bulb ballasts 120, on-off switch 122, system operation indicator 124, microprocessor 126 and safety switch 128, for example. Assembly 100 also includes suitable mounting elements or features such as shock absorbing mounts 130.

Thus, atmosphere treating unit structure 102 includes first zone 140 in which ozone is generated within the atmosphere and exposed to UV light, and second zone 144 in which at least a portion of the generated ozone is removed from the mixed atmosphere to form an ozone-depleted mixture. First zone 140 and second zone 144 are generally represented by respective zone boxes, shown via phantom lines in FIG. 22. Those skilled in the art and guided by the teachings herein provided will understand and appreciate that such depiction of the zones is not intended to necessarily limit the size, shape or dimensions of the zones or the placement or positioning of the zones. Furthermore, as for example herein described, such zones relative to each other, may be separated, adjacent or overlap, in whole or in part, as may be appropriate or desired for a particular application.

In such structure, UV light bulbs 110, used to generate ozone and to irradiate ozone mixed with the atmosphere, are oriented perpendicularly to atmosphere flow through the structure.

In particular embodiments, it can be desirable to expose the mixture of atmosphere and ozone to UV light of either 185 or 254 nm wavelength at an input rate of 0.5 watt per cfm to 10 watts per cfm, where such input rates or ratios reflect power into the UV bulb(s) divided by the total flow rate through the system/unit.

Assembly 100 may include one or more shut-off devices 150 in operational communication with structure 102 to shut-off atmosphere treatment assembly 100 when a selected ozone level parameter exceeds a preselected amount. One or more shut-off devices 150 can be variously located within or about assembly 100. For example, FIG. 21 illustrates a first possible location, showing one shut-off device 150 as specifically designated by reference 152, in air inlet region 104 and a second possible location, showing another shut-off device 150 as specifically designated by reference 154 downstream of catalytic ozone destruction bed 112. FIG. 22, in addition to location 152 also shows possible a specific location 156 of shut-off devices 150 within catalytic ozone removal bed 112 and location 160, downstream of catalytic ozone removal bed 112. The arrows in FIG. 22 show flow direction 41 along which fluid passes through the unit assembly 100.

Suitable such shut-off devices may be in the form or nature of a fuse, e.g., an integral ozone fuse such as can automatically shut down assembly operation if and when the fuse is blown. For example, a chemical input such as a level or amount of ozone triggers an electrical switch or fuse such as to shut down operation of the assembly such as by turning off the UV light bulbs.

Figure 23:
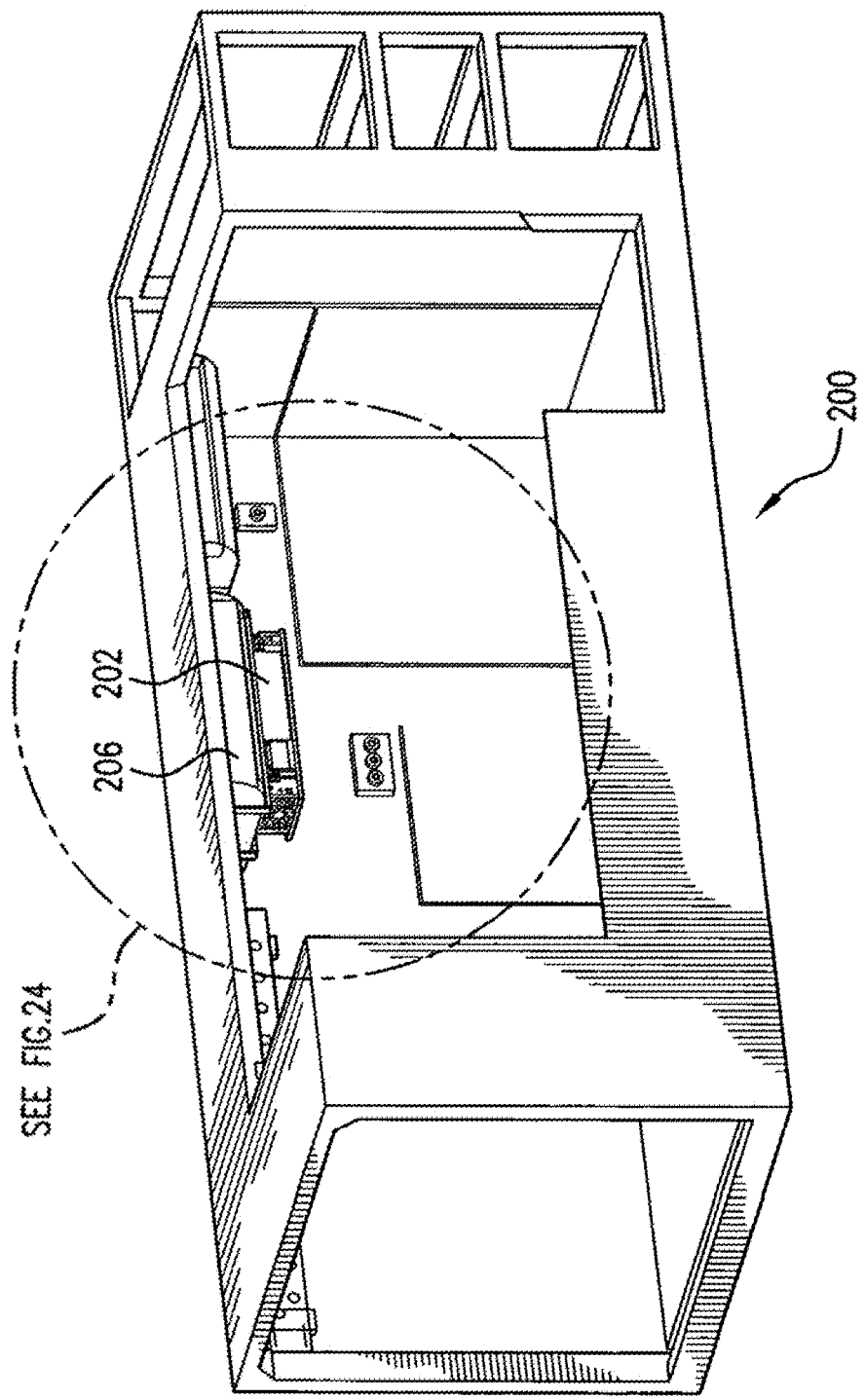
FIG. 23 is a partially cut-away view of an enclosed space, such as a refrigerated truck trailer, operationally associated with an atmosphere treatment assembly in accordance with one embodiment of the subject matter disclosed herein.
Figure 24:
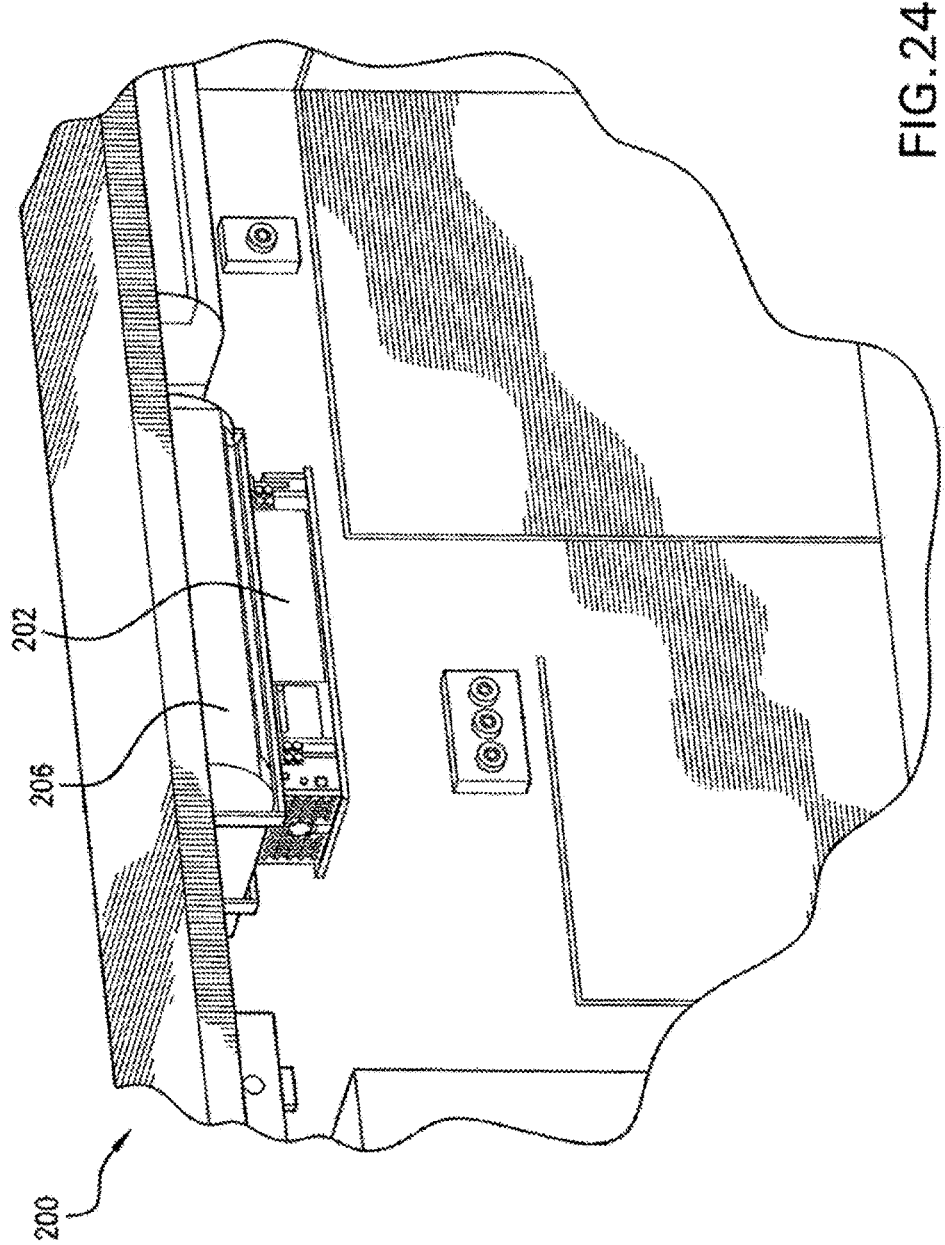
FIG. 24 is an enlarged perspective fragmentary view showing a partial cut-away of an enclosed space operationally associated with an atmosphere treatment assembly, according to the embodiment as shown in FIG. 23.

FIGS. 23 and 24 are partially cut-away views of enclosed space 200, such as a refrigerated truck trailer, operationally associated with atmosphere treatment assembly 202 in accordance with one embodiment of the subject matter disclosed herein. In other embodiments of the subject matter disclosed herein, enclosed space 200 comprises and/or is formed by a room of a building, a building structure and/or any other suitable structure that contains, houses, has and/or forms a space or other similar environment within a residential building, a commercial building, an industrial building and/or any other similar building structure or other structure that forms a space and/or an environment that is or is not sealed, ventilated, conditioned and/or otherwise environmentally controlled.

Enclosed space 200 can be normally used to carry or convey one or more products (not shown), with atmosphere treatment assembly 202 used to treat the atmosphere held or otherwise contained within the enclosed space.

In some embodiments of the subject matter disclosed herein, enclosed space 200 also houses or contains evaporator 206 such as may be utilized to control the humidity or moisture level within the enclosed space 200.

Those skilled in the art and guided by the teachings herein provided will appreciate that, in accordance with any one embodiment, the atmosphere in a storage container can desirably be cleaned via repeated circulation through a treatment or cleaning unit, such as herein described. For example, in the case of desired removal of ethylene from a selected atmosphere, at least a portion of the ethylene can be destroyed in each pass through the unit. As long as the rate of destruction of ethylene is higher than the rate of generation of ethylene in the storage container, the cleaning apparatus will reduce the ethylene levels to a desired steady-state level. By designing the cleaning apparatus to partially clean the atmosphere on a per pass basis, and relying on recirculation of the atmosphere to reduce the contaminants to desired levels, the balance between system performance, volume and cost can be better optimized. For example, by utilizing such recirculation, the amount of power or energy required for proper operation of the unit can be significantly reduced or minimized such as by reducing the number of UV lights required to be energized in any particular pass of atmosphere to be treated through the unit.

Figure 25:
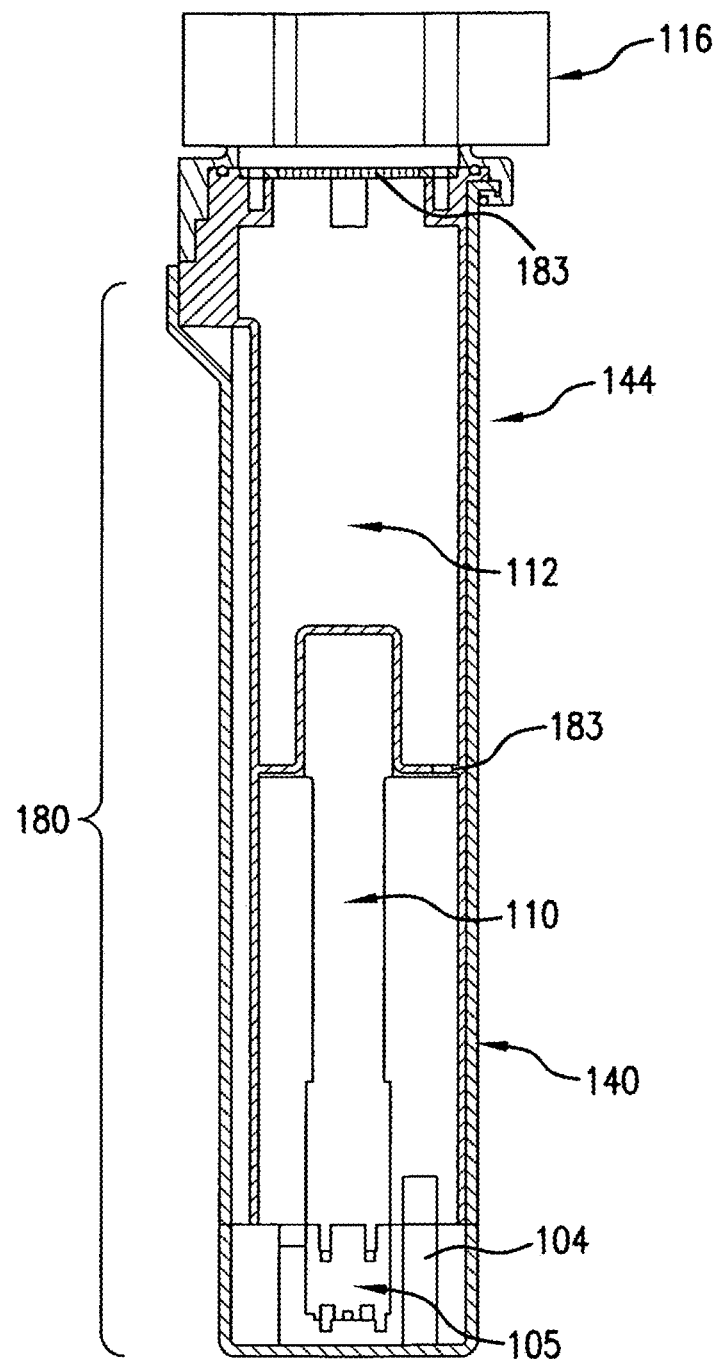
FIG. 25 is a cross section of an assembly in accordance with one aspect of the subject matter disclosed herein.
Figure 26:
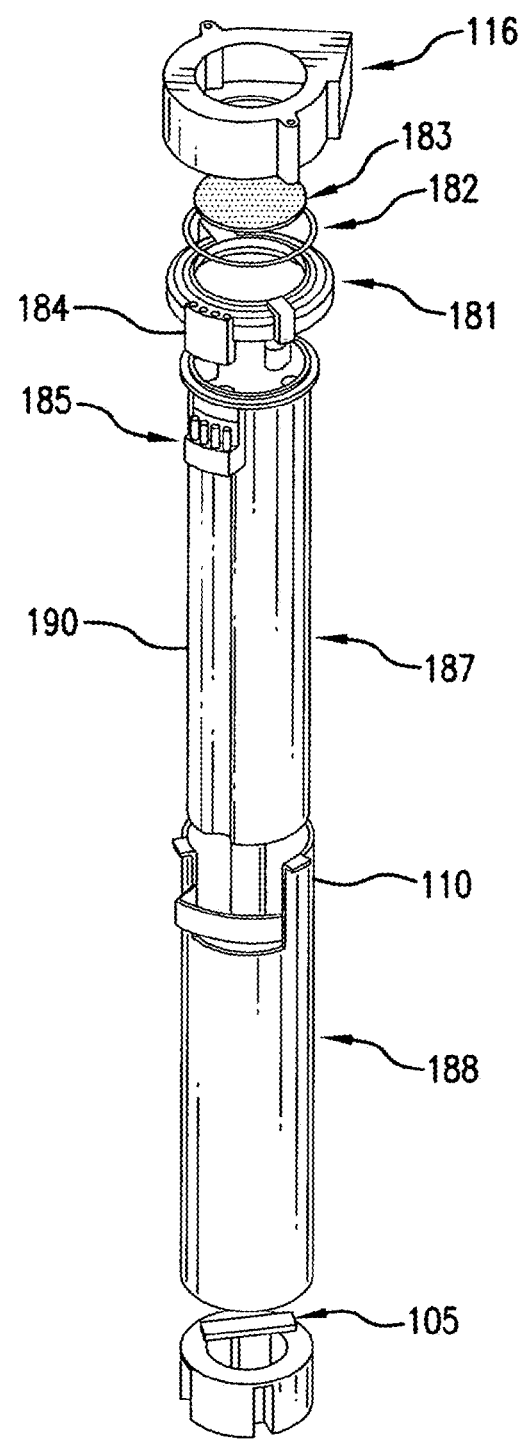
FIG. 26 is an exploded view of the assembly shown in FIG. 25.
Figure 27:
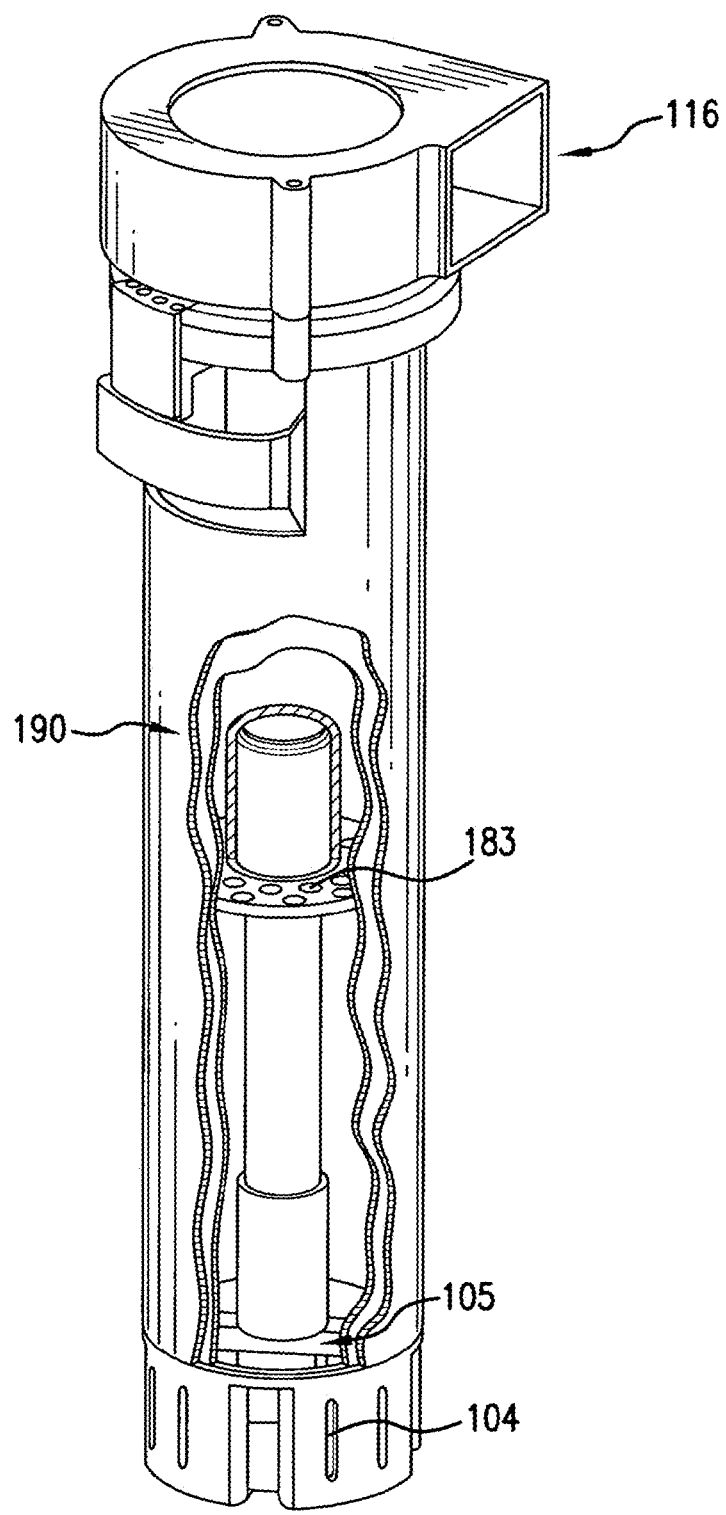
FIG. 27 is a three dimensional view of the assembly shown in FIG. 25.

FIGS. 25-27 illustrate an apparatus that is designed for efficient replacement of the UV bulb and catalyst assembly. The system is shown in cross section, 3-D wire drawing and exploded view in FIGS. 25-27. This apparatus minimizes the size of the unit and simplifies the replacement of the consumable "cartridge". The electrical connections are inserted together and a rotatable outer housing is used to lock the cartridge in place with the fan and motor.

As shown in FIG. 25, air is pulled through the assembly by fan 116. The air enters the unit through the air inlet 104. This air inlet 104 comprises an air inlet screen and a structure that supports the UV bulb connector 105. The air flows from the air inlet 104 into the initial air treatment zone 140 where the air is exposed to ozone generated by UV bulb 110. The air in this zone is both mixed with ozone and exposed to UV light from bulb 110. The air then passes from the first zone 140 to the second zone 144 where ozone is removed from the air in catalyst bed 112. The catalyst material is held in bed 112 with screens 183 at the inlet and exhaust from the second zone 144.

The exploded view in FIG. 26 illustrates the elements that make the unit easy to replace for periodic maintenance. The replacement cartridge 180 comprises an interior cartridge 187 and a rotating exterior interlock housing 188. Electrical connector 185 inserts into the electrical connector 184 that is an integral part of the permanent mounting ring 181. Mounting ring 181 is connected to the fan 116 through the O-ring 182. The replacement cartridge 180 is removed by rotating exterior interlock housing 188 and pulling down on the interior cartridge 187 thus disconnecting electrical connectors 184 and 185 without applying undue torque or force to this delicate connector. A new replacement cartridge is installed by reversing the steps of removing the replacement cartridge.

The 3-D drawing shown in FIG. 27 illustrates electrical wiring path 190 through which wires are passed to connect the UV bulb connector 105 to the power available from the fan 116 which can be permanently mounted to or within a chamber, such as a refrigerator or a storage bin or a space or room of a building. Electrical power is available to fan 116 from a permanent source or a power source.

Figure 28:
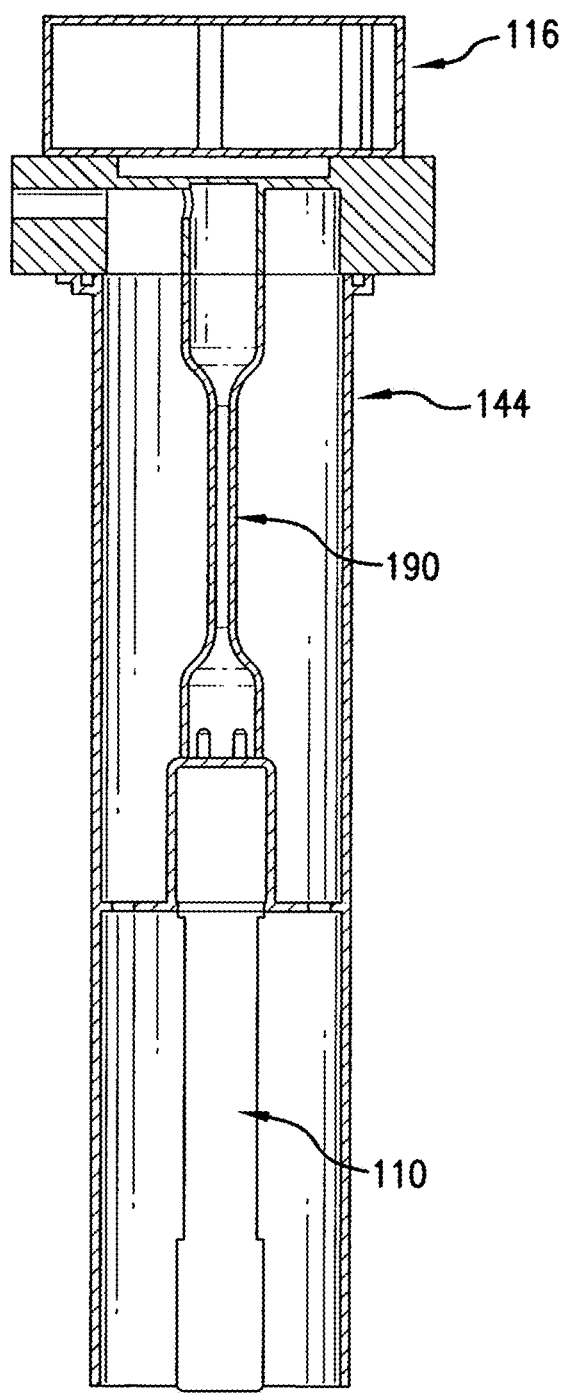
FIG. 28 is a partial sectional view of an assembly in accordance with another embodiment of the subject matter disclosed herein.
Figure 29:
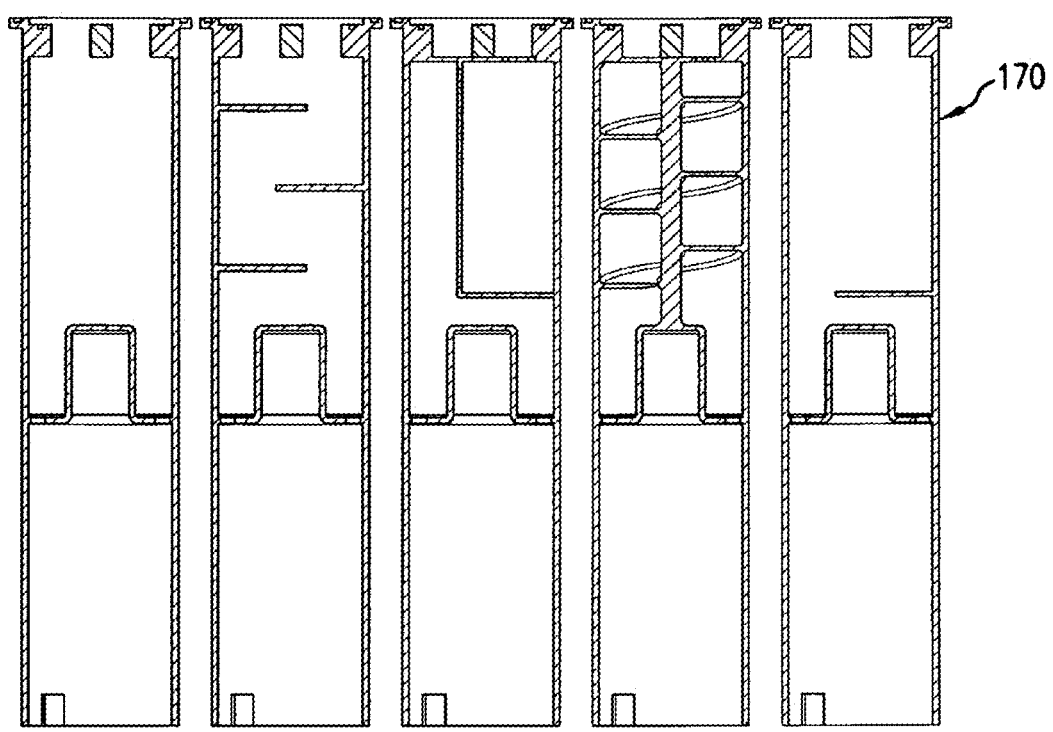
FIG. 29 shows five different embodiments of partial sectional views showing different baffle arrangements according to different configurations of assemblies according to the subject matter disclosed herein.
Figure 30:
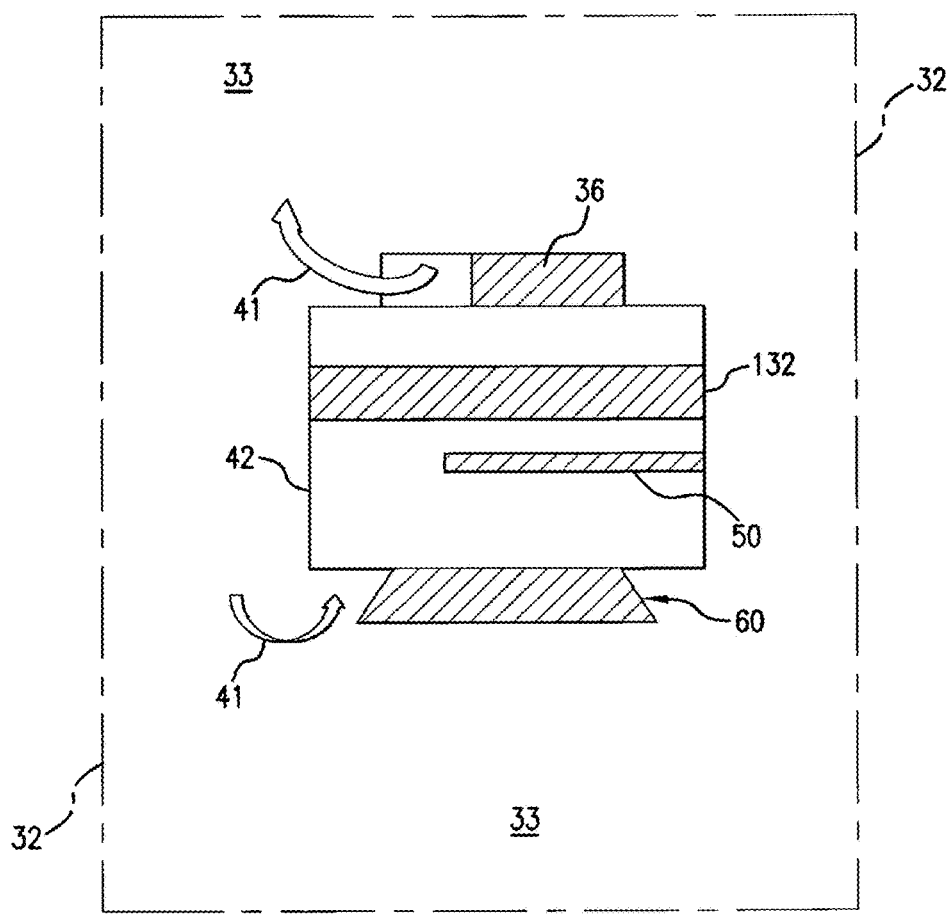
FIG. 30 is a diagrammatic showing an air cleaner cross section located inside of a container, such as a room, another similar space and/or environment within a residential building space, a commercial building space, an industrial building space and/or a space of any other similar building structure, structural element and/or other structure that forms a space, according to one embodiment of the subject matter disclosed herein.

FIG. 28 illustrates an alternative configuration for wiring path 190. In this configuration wiring path 190 is centered in the middle of second zone 144. The cross section drawing shown in FIG. 29 illustrates 5 different options for baffling 170 within catalyst bed 112. These baffling configurations provide options to ensure flow through the catalyst bed regardless of the orientation of the overall cartridge, vertical or horizontal.

In other embodiments according to the subject matter disclosed herein, a method and apparatus for air purification is used to modify, purify and/or otherwise clean atmosphere 33, such as the air in an indoor environment, for example, in or within a room or other similar space of a building. In some embodiments of the subject matter disclosed herein, the air purification method or process comprises the following steps. Contaminated air is drawn into air cleaning unit 40. In some embodiments of the subject matter disclosed herein, air mover 36 is operated to draw contaminated air into air cleaning unit 40. In some embodiments of the subject matter disclosed herein, air mover 36 comprises an induced draft fan or other similar air moving device or apparatus.

In some embodiments of the subject matter disclosed herein, the term "contaminated air" refers to air and/or another atmosphere and/or environment that contains gases, such as odors or other volatile compounds such as volatile organic compounds, microbes, such as bacteria, viruses, molds, fungi and/or spores, and/or allergens, including but not limited to pet dander, dust mite parts and/or pollen.

As shown in FIG. 31, for example, the contaminated air passes or is otherwise drawn by, around and/or past baffles, for example light baffles 72 as shown in FIG. 31, and/or any other similar structure that inhibits light, such as UV light, from escaping out of or discharging from air cleaning unit 40. In some embodiments of the subject matter disclosed herein, the contaminated air is exposed to UV light that irradiates the contaminated air, such as within or inside of the air cleaning unit 40, with light, such as UV light at a wavelength of about 254 nm and/or 185 nm.

In some embodiments of the subject matter disclosed herein, UV light at a wavelength of 185 nm produces ozone in the contaminated air, such as of atmosphere 33, for example, that mixes with the contaminated air drawn into air cleaning unit 40. Exposure of the contaminated air to UV light and ozone, in some embodiments of the subject matter disclosed herein, kills all or a portion of a microbial load in the air as the air passes through air cleaning unit 40. In some embodiments of the subject matter disclosed herein, exposure of the contaminated air to UV light and ozone alters the proteins in allergens, for example, so that an allergenicity is reduced, in some embodiments of the subject matter disclosed herein so that the modified allergens no longer trigger an allergic response in a sensitive person having contact with the treated particles.

In some embodiments of the subject matter disclosed herein, gases and the contaminated air react with ozone in the presence of UV light to produce, predominantly, $CO_2$ or $N_2$ and water. The cleaned and/or modified air, that now has reduced amounts of gases as well as inactivated microbes and allergens with reduced allergenicity, and ozone, pass through an oxidizing catalyst that reduces ozone levels to at or below ambient levels, and further oxidizes any remaining gases in the air and/or atmosphere 33.

In some embodiments of the subject matter disclosed herein, a catalyst bed, such as a granular catalyst bed acts or can be used as a coarse filter that traps relatively large microbes and/or particles, including but not limited to allergens. These trapped particles thus have an extended time of exposure to UV light and ozone and the extended time can be used to continue to oxidize and thus further inactivate the trapped particles over the extended time.

In some embodiments of the subject matter disclosed herein, the modified air and/or atmosphere 33, that has been reduced to a level of microbes and allergens and gases and ozone levels that are lower than in the incoming ambient air, is exhausted back into the room, such as the room of container 32. Over a defined time period, the air and/or atmosphere 33 can circulate or re-circulate through air cleaning unit 40 or another suitable air purifier to continue to lower contaminant levels in the ambient air, such as of the atmosphere 33 within container 32.

According to some embodiments of the subject matter disclosed herein, the catalyst of catalyst bed 132 is a manganese dioxide/copper oxide mixture, for example, in the form of granules having a 4×8 mesh, which means that the size of each granule is between about ⅛" and about ¼". In another embodiment of the subject matter disclosed herein the catalyst of catalyst bed 132 is a manganese dioxide/copper oxide mixture, for example in the form of pellets approximately 1-4 millimeters in diameter and approximately 2-10 millimeters long. Some catalysts work by reducing the activation energy needed for one or more reactions to take place. In some embodiments of the subject matter disclosed herein, the ozone, the oxygen in the contaminated air, and the gases to be oxidized all adsorb on the surface of the catalyst where the energy needed for them to react with each other is decreased. If the gases are oxidized than each product of that reaction is released back into the air or atmosphere 33 and then discharges from or exits the system, such as of container 32.

In some embodiments of the subject matter disclosed herein, relatively low levels of ozone get back into the air or atmosphere 33. Depending on the amount of catalyst used, and the power of any UV bulb or other UV light source, either there is less, the same or slightly higher ozone amounts than contained in the ambient air. If air cleaning unit 40 is run with the bulb off, then the ozone can be significantly lower than levels in the ambient air. In some embodiments of the subject matter disclosed herein, the exhaust or discharge will have less than, for example, the CARB standard of 50 ppb ozone. In some embodiments of the subject matter disclosed herein, a preferred level can be to exhaust at no more than 30 ppb ozone. In some embodiments of the subject matter disclosed herein, ozone will decompose rapidly to oxygen, so that room levels can be maintained healthy.

FIG. 31 shows a cross section of air cleaning unit 40, also referred to as an air purifier, according to one embodiment of the subject matter disclosed herein. As shown in FIGS. 31-35, in some embodiments of the subject matter disclosed herein, bed structure 191 applies or is designed to directly or indirectly apply a compressive force on the catalyst granules of catalyst bed 132 as bed structure 191 is constructed or assembled. In some environments of the subject matter disclosed herein, the compressive force applied to, at and/or on catalyst bed 132 holds or maintains the catalyst granules and/or the catalyst material in a particular position and/or orientation, particularly after that structure 191 is assembled and thus can be used to inhibit and/or limit movement, particularly undesired movement, of the catalyst particles, which can reduce friction between catalyst particles and thus reduce the associated attrition of the catalyst material, particularly as it results from catalyst particle to catalyst particle abrasion.

As shown in FIGS. 31-35, the upper and lower frames of bed structure 191 which holds catalyst bed 132 comprise, in some embodiments of the subject matter disclosed herein, a plastic and/or other durable material structure and an embedded screen material positioning, holding and/or securing the catalyst granules while allowing the contaminated air to flow through the upper and lower frames, which can be used to hold or otherwise positioned the packed catalyst particles and/or catalyst materials. The upper frame of bed structure 191, in some embodiments of the subject matter disclosed herein, is configured with or comprises tapered spacers 194, which in some embodiments can be or form a hollow structure. In some embodiments of the subject matter disclosed herein, spacers 194 are tapered and/or are aligned to fit over posts 195 which in some embodiments of the subject matter disclosed herein are located and/or positioned in the lower frame of bed structure 191.

In some embodiments of the subject matter disclosed herein, an assembly procedure begins with filling the lower frame with the catalyst particles and/or granules. After the lower frame is filled with the catalyst material, the upper frame is positioned and/or located so that tapered spacers 194 of and/or attach to the upper frame align over the posts 195 in the lower frame. In some embodiments, as tapered spacers 194 are pressed over posts 195, the catalyst material sandwiched between the upper and lower frames is forced and/or otherwise pushed away from tapered spacers 194 and are thus compressed together to hold the catalyst material relatively tightly in the upper and lower frames of bed structure 191. In some embodiments of the subject matter disclosed herein, as the upper and lower frames are pressed together or otherwise drawn together to reduce a distance between the upper and lower frames, the catalyst material is compressed and held in position or in place. In some embodiments of the subject matter disclosed herein, the assembly may be vibrated as the upper and the lower frames are pressed together in order to more uniformly compress the granules or pellets of catalyst. A screw and/or another suitable fastener can be tightened into and/or with respect to any one or more posts 195, such as in a direction from the corresponding tapered spacer 194, for example to securely position or otherwise hold the bed together, such as in an assembled condition. In some embodiments of the subject matter disclosed herein, bed structure 191 holds a screen or screen material that can be made of appropriately sized mesh to hold the catalyst granules in catalyst bed 132.

In some embodiments of the subject matter disclosed herein, a combination of relatively low cost switches are used or employed to properly operate air cleaning unit 40. The combination of switches can be used in place of or can substitute for the use of an ozone sensor in the outlet. An ozone sensor can be expensive and/or can have a relatively short operating life. In some embodiments of the subject matter disclosed herein, the combination of a pressure switch, a flow switch and a tilt switch can help ensure safety and performance of air cleaning unit 40 and/or atmosphere 33 within container 32. In some embodiments of the subject matter disclosed herein, the pressure switch can be activated, for example, by the pressure drop across catalyst bed 132. In some embodiments of the subject matter disclosed herein, the flow switch comprises two thermistors, for example, positioned or located near any UV bulb in the reaction zone of air cleaning unit 40. In some embodiments of the subject matter disclosed herein, the tilt switch, for example, can be used to ensure that catalyst bed 132 is properly oriented and/or positioned.

In some embodiments of the subject matter disclosed herein, the flow switch is a set of configured thermistors. According to certain embodiments of the subject matter disclosed herein, the start-up sequence of air cleaning unit 40 begins with the switch activating the controls. If the tilt switch is not engaged, in some embodiments, then air mover 36 and/or the induced draft fan is turned on. If the tilt switch is engaged, then the air mover and/or the induced draft fan is not turned on. Once air mover 36 and/or the induced draft fan is operating in the on mode, controls 60 and/or another suitable controller waits for the pressure switch to engage, to demonstrate that there is suction from air mover 36 and/or the induced draft fan. In some embodiments of the subject matter disclosed herein, the controller also waits for the flow switch to engage, to demonstrate that there is flow into air cleaning unit 40 and/or the air purifier.

In some embodiments of the subject matter disclosed herein, after the pressure switch and the flow switch are engaged, the UV bulb is energized and ozone is safely produced. After the controls of the subject matter disclosed herein are powered, the controls will continuously monitor a mode selector switch. In some embodiments of the subject matter disclosed herein, the controls will continuously check for errors when in either of the run modes. In some embodiments of the subject matter disclosed herein, the errors include a low flow rate, an excessive inclination, and no UV light. If any of these errors occur, for example, the controls will power off the ballast for the UV light, turn air mover 36 and/or the induced draft fan off after 8 seconds and set an appropriate fault indicator and/or alarm.

In some embodiments of the subject matter disclosed herein, a first touch of a capacitive touch switch of air cleaning unit 40 and/or another unit will place the system and a quick clean mode. For example, air mover 36 and/or the induced draft fan can be turned on high and can set a high flow indicator. Any particular UV bulb can be turn on once the pressure switch verifies a proper flow or flow rate. If the flow rate is not verified it can set a call customer service indicator, and power the ballast off and turn off air mover 36 and/or the induced draft fan. In some embodiments of the subject matter disclosed herein, a thermistor flow sensor can continuously check and verify that the air purifier and/or air cleaning unit 40 is maintaining proper flow rate. If the flow rate is not verified the controller can set a call customer service indicator and/or can turn off the power to the ballast and/or air mover 36 and/or the induced draft fan.

In some embodiments of the subject matter disclosed herein, the electronic ballast monitors the power to the UV light source, such as the UV bulb and verifies that the UV bulb is functioning properly. If the UV bulb being on is not verified the controller can set a UV bulb error indicator and/or can turn off the power to the ballast and/or turn off air mover 36 and/or the induced draft fan, for example after 4 seconds or at any other desired time period. In some embodiments of the subject matter disclosed herein, the controller can check for a proper tilt condition, and if the proper tilt condition exists, the controller can set a tilt indictor and/or alarm, can turn off the ballast and/or can turn air mover 36 and/or the induced draft fan, for example after 4 seconds or at any other suitable time period.

In some embodiments of the subject matter disclosed herein, a second touch of a capacitive touch switch can put air cleaning unit 40 and/or the air purifier into a whisper quiet mode, for example, which can turn on air mover 36 and/or the induced draft fan, for example to a low setting, and/or can set a low flow rate indicator. In some embodiments of the subject matter disclosed herein, the UV bulb is turned on after the pressure switch verifies a proper flow rate. If the flow rate is not verified the controller can set a call customer service indicator, can leave power to the ballast off and/or can turn off air mover 36 and/or the induced draft fan.

In some embodiments of the subject matter disclosed herein, the thermistor flow sensor continuously checks and verifies that air cleaning unit 40 is maintaining a proper flow rate. If the flow rate is not verified, the controller can set a call customer service indicator, can turn off power to the ballast and/or to air mover 36 and/or the induced draft fan. The electronic ballast can monitor the power to the UV bulb and verify that the UV bulb is functioning properly. If the UV bulb on mode is not verified the controller can set a bulb error indicator, can turn off power to the ballast and/or can turn off air mover 36 and/or the induced draft fan, for example after 4 seconds or at any other suitable time period.

In some embodiments of the subject matter disclosed herein, a tilt condition can be checked. If the tilt condition exists, the controller can set a tilted indictor, can turn off power to the ballast and/or can turn air mover 36 and/or the induced draft fan off, for example after 4 seconds or at any other suitable time period.

In some embodiments of the subject matter disclosed herein, a third touch of the capacitive touch switch can place air cleaning unit 40 and/or the unit into a shutdown mode which can turn off the UV bulb, flash a flow indicator and/or turn off air mover 36 and/or the induced draft fan, for example after 4 seconds or at any other suitable time period.

Figure 42:
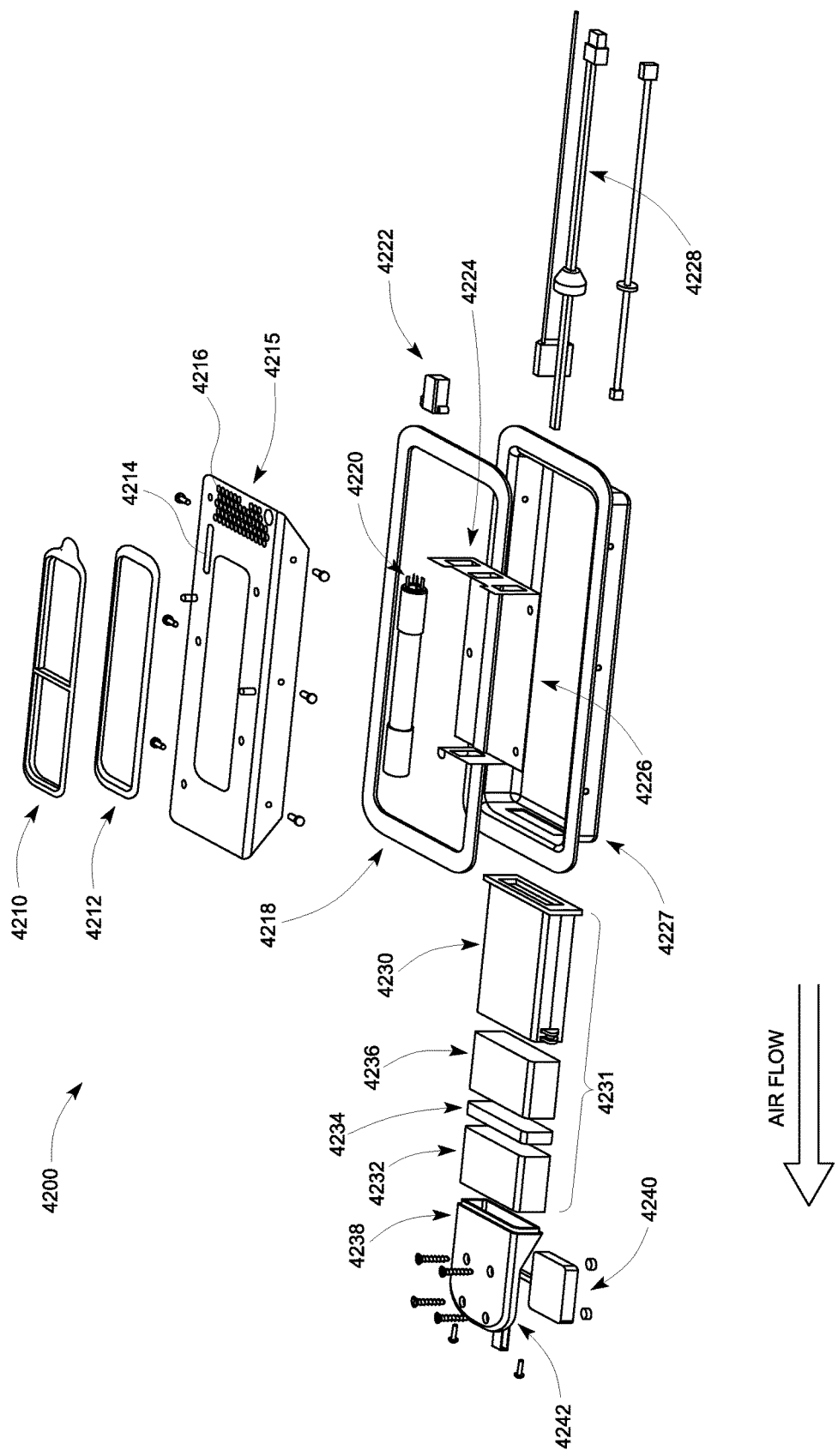
FIG. 42 illustrates an exploded view of an apparatus for treating air 4200 according to some embodiments of the subject matter disclosed herein.

FIG. 42 illustrates an exploded view of an apparatus for treating air 4200 according to some embodiments of the subject matter disclosed herein. The apparatus for treating air 4200 can include a light cover 4210, a cover gasket 4212, a proximity sensor (e.g. magnetic proximity sensor) 4214, an unit cover 4215, an air inlet 4216, a gasket enclosure to evaporator cover 4218, a UV light bulb 4220, a UV light bulb socket 4222, a UV light bulb holding bracket 4224, an air treatment zone 4226, an enclosure of the air treatment zone 4227, power and sensor wires 4228, an ozone removal zone 4231, a catalyst housing 4230, a first catalyst section 4236, a catalyst spacer 4234, a second catalyst section 4232, an air mover (e.g., a fan) 4240, a housing for the air mover 4238, and an air outlet 4242.

The apparatus for treating air 4200 can include a housing with an air inlet (e.g., 4216) and an air outlet (e.g., 4242). In some embodiments, the enclosure for the air treatment zone 4227, the catalyst housing 4230, and the housing for the air mover 4238 can form a multi-section or unibody housing for the apparatus for treating air 4200. The apparatus for treating air 4200 can include an air treatment zone (e.g., 4226) and an ozone removal zone (e.g., 4231). As illustrated in FIG. 42, the ozone removal zone 4231 is positioned downstream of the air treatment zone 4226 with respect to a flow direction of the air being treated.

The apparatus for treating air 4200 can include an UV light source (e.g., 4220) in the air treatment zone 4226 configured to generate ozone from the air. The UV light from the UV light source and the ozone generated by the UV light source can treat (e.g., clean, sanitize, or deodorize) the air in the air treatment zone 4226.

The apparatus for treating air 4200 can include catalyst in the ozone removal zone 4231 that removes at least a portion of the ozone generated by the UV light source (e.g. 4220). As illustrated in FIG. 42, the ozone removal zone 4231 can include the first catalyst section 4236 and the second catalyst section 4232, separated by the spacer 4234. The configuration of two separate catalyst sections with a spacer in between can improve the flow of air through the ozone removal zone 4231. For example, the spacer 4234 can allow the air coming out of the first catalyst section 4236 to redistribute before entering into the second catalyst section 4232. The redistribution of air flow can improve the performance of the ozone removal zone 4231.

The apparatus for treating air 4200 can include an air mover (e.g., 4230) positioned near the air outlet (e.g., 4242) that can draw the air through the air inlet (e.g., 4216) into the air treatment zone (e.g., 4226) from outside the housing, moving the air through the air treatment zone (e.g., 4226) and the ozone removal zone (e.g., 4231), and then emitting the air through the air outlet (e.g., 4242) out of the apparatus 4200.

The apparatus for treating air 4200 can include a proximity sensor (e.g., 4214). The proximity sensor can be attached to the housing. The proximity sensor can detect the presence of a cover outside the housing of the apparatus 4200. The cover can be protective (e.g., to provide additional shield of the UV light) or decorative. The apparatus 4200 can turn off the UV light source if a cover is not detected. In some examples, the proximity sensor can be magnetic.

The apparatus for treating air 4200 can include a power connector (e.g., 4228). The power connector can be connected to a power source inside a container (e.g., a refrigerator) to provide power to the apparatus 4200. In some embodiments, the apparatus for treating air 4200 can also include one or more sensors to detect the condition of the ambient environment (e.g., temperature, air quality, contaminant content and/or level, etc.)

In some embodiments, the interior surface of the housing of the apparatus 4200 (e.g., in the air treatment zone 4226) can be at least partially coated with a reflector layer (e.g., metal layer such as aluminum). The components of the apparatus can be made in various materials, such as metal or plastics. Certain structural materials (e.g., plastics) can reduce the weight and/or cost of the apparatus 4200, but can deteriorate over time, especially in the presence of UV light. Coating the interior surface of the housing with a reflector layer can shield the structural materials from UV light and extend its usage life; it can also reduce the absorption of UV by the interior surface of the apparatus and enhance the UV light intensity inside the air treatment zone, thus improving the performance of the air treatment zone.

Figure 43:
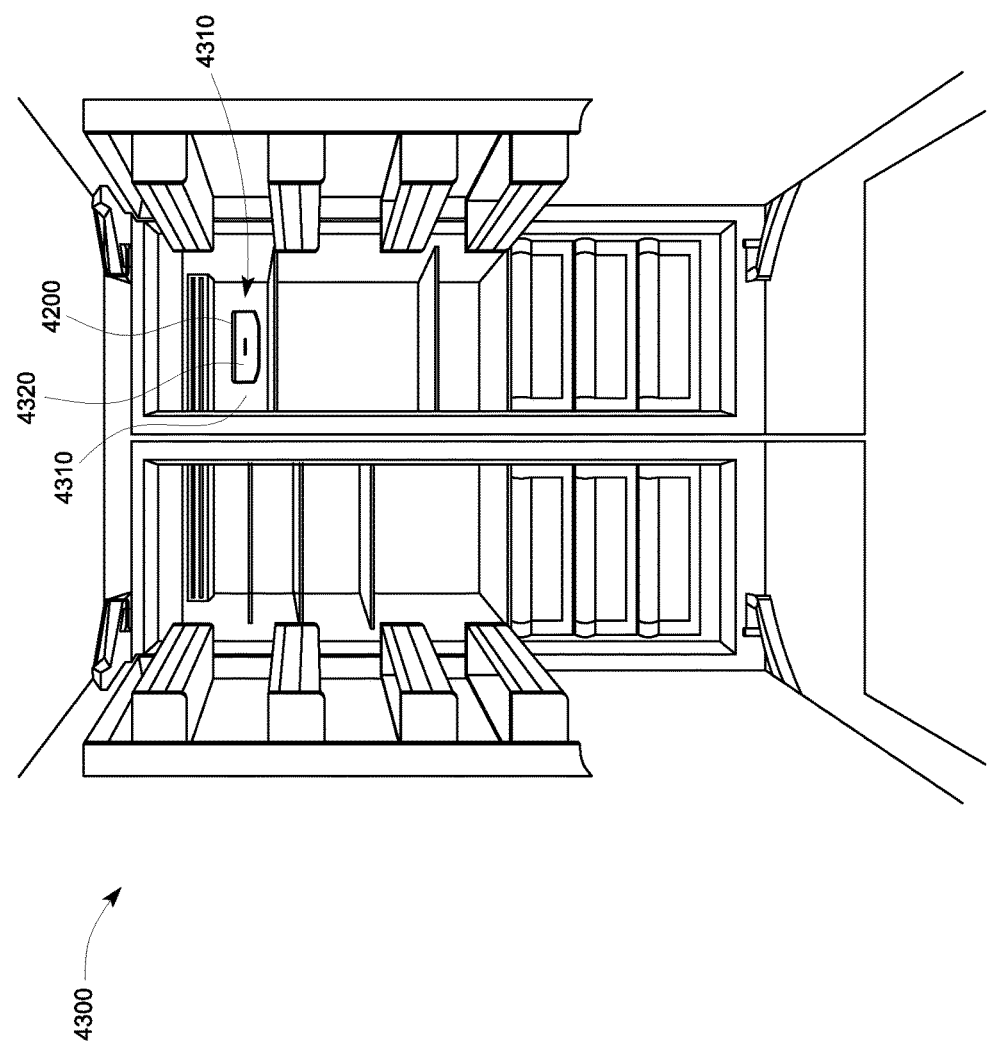
FIG. 43 illustrates a refrigerator 4300 containing an apparatus for treating air as illustrated in FIG. 42, according to some embodiments of the subject matter disclosed herein.

FIG. 43 illustrates a refrigerator 4300 containing an apparatus for treating air 4200 as illustrated in FIG. 42, according to some embodiments of the subject matter disclosed herein. The apparatus for treating air 4200 can be mounted on the back wall 4310 inside the refrigerator 4300. The power connector 4228 of the apparatus 4200 can be connected to a power source inside the refrigerator 4300. In some embodiments, the apparatus for treating air 4200 can also contain a ballast, which can regulate voltage, current, and/or frequency of the power. The power connector 4228 can be connected to the ballast, which can be connected to a power source inside the refrigerator 4300. In some embodiments, the ballast can be part of the refrigerator itself. The apparatus 4200 can be covered by a decorative and/or protective cover 4320. In some embodiments, the apparatus for treating air 4200 can be mounted next or close to the evaporator cover of the refrigerator 4300. In operation, the air is drawn from the storage space of the refrigerator 4300 into the apparatus for treating air 4200. After treatment, the air is emitted from the apparatus 4200 into the space behind the evaporator cover of the refrigerator 4300. The air can flow back into the storage space of the refrigerator through the existing refrigerator evaporator fan of the refrigerator 4300. In some embodiments, the apparatus 4200 itself can include no active air mover component. Instead, the apparatus 4200, when mounted near or next to the evaporator cover of a refrigerator, can leverage the evaporator fan of the refrigerator to function as an air mover.

Figure 44:
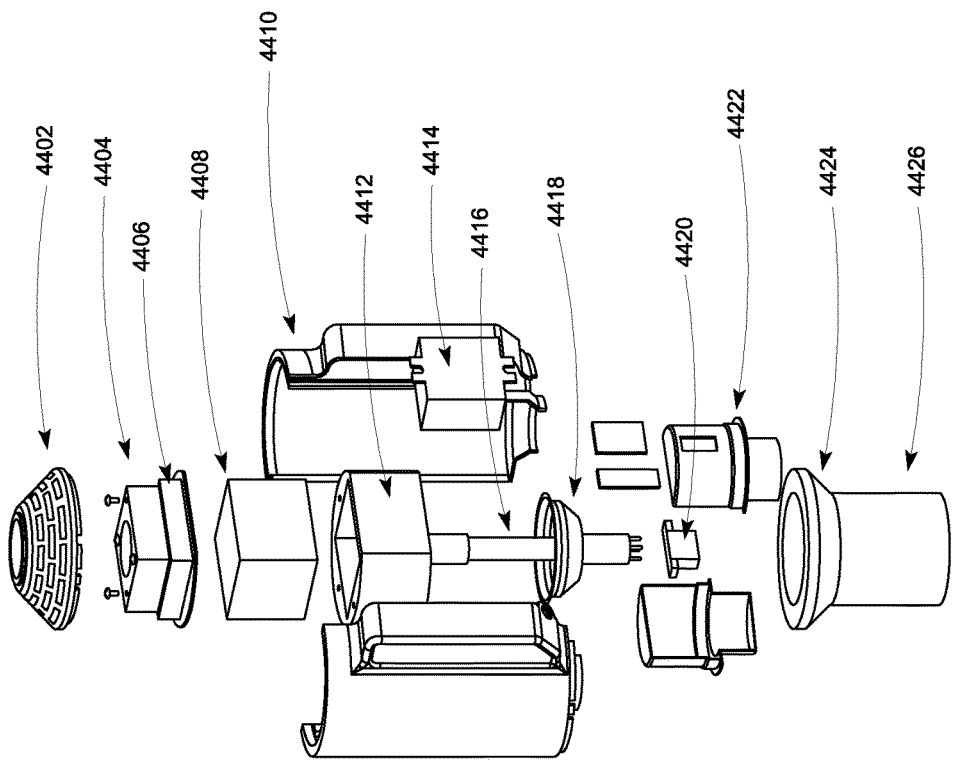
FIG. 44 illustrates an exploded view of another apparatus for treating air 4400 according to some embodiments of the subject matter disclosed herein.

FIG. 44 illustrates an exploded view of another apparatus for treating air 4400 according to some embodiments of the subject matter disclosed herein. The apparatus for treating air 4400 can include an outlet grill 4402, a fan 4404, a fan housing 4406, catalyst 4408, exterior walls 4410, a catalyst holder 4412, a ballast 4414, an UV light bulb 4416, an UV light baffle 4418, a light bulb socket 4420, a keyed light bulb holder 4422, an air inlet 4424, and an unit positioner 4426.

The apparatus for treating air 4400 can include a housing with an air inlet (e.g., 4424) and an air outlet (e.g., 4402). In some embodiments, the exterior walls 4410, the outlet grill 4402, the keyed light bulb holder 4422 can form a multi-section or unibody housing for the apparatus for treating air 4400. The apparatus for treating air 4400 can include an air treatment zone and an ozone removal zone. The ozone removal zone is positioned downstream of the air treatment zone with respect to a flow direction of the air being treated.

The apparatus for treating air 4400 can include an UV light source (e.g., 4416) in the air treatment zone configured to generate ozone from the air. The UV light from the UV light source and the ozone generated by the UV light source can treat (e.g., clean, sanitize, or deodorize) the air in the air treatment zone.

The apparatus for treating air 4400 can include catalyst in the ozone removal zone that removes at least a portion of the ozone generated by the UV light source (e.g. 4416). As in the apparatus 4200 illustrated in FIG. 42, the ozone removal zone in the apparatus 4400 can also include two or more catalyst sections, separated by one or more spacers.

The apparatus for treating air 4400 can include an air mover (e.g., 4404) positioned near the air outlet (e.g., 4402) that can draw the air through the air inlet (e.g., 4424) into the air treatment zone from outside the housing, moving the air through the air treatment zone and the ozone removal zone, and then emitting the air through the air outlet (e.g., 4402) out of the apparatus 4400.

The apparatus for treating air 4400 can include a positioner (e.g., 4426). The positioner can help the apparatus 4400 to be positioned and secured/fit to certain spaces or locations, e.g., behind a front seat or inside a cup holder inside a vehicle cabin.

The apparatus for treating air 4400 can include a power connector. The power connector can be connected to a power source inside a vehicle (e.g., a cigarette lighter or USB port) to provide power to the apparatus 4400. In some embodiments, the apparatus for treating air 4400 can also include one or more sensors to detect the condition of the ambient environment (e.g., temperature, air quality, contaminant content and/or level, etc.)

The apparatus for treating air 4400 can include a ballast (e.g., 4414). The ballast can help provide desired power to the apparatus 4400. In some embodiments, the ballast can regulate the current to the UV light source (e.g., UV lamps) and provide sufficient voltage to start the UV light source (e.g., UV lamps). In addition, the ballast can convert the voltage of the available power source to the voltage needed to operate the UV light source (e.g., UV lamps). For example the ballast 4414 can convert the power originated from a cigarette lighter or USB port of a vehicle to a higher frequency and higher voltage power, suitable for the apparatus 4400.

In some embodiments, the interior surface of the housing of the apparatus 4400 (e.g., in the air treatment zone) can be at least partially coated with a reflector layer (e.g., metal layer such as aluminum).

Figure 45A:
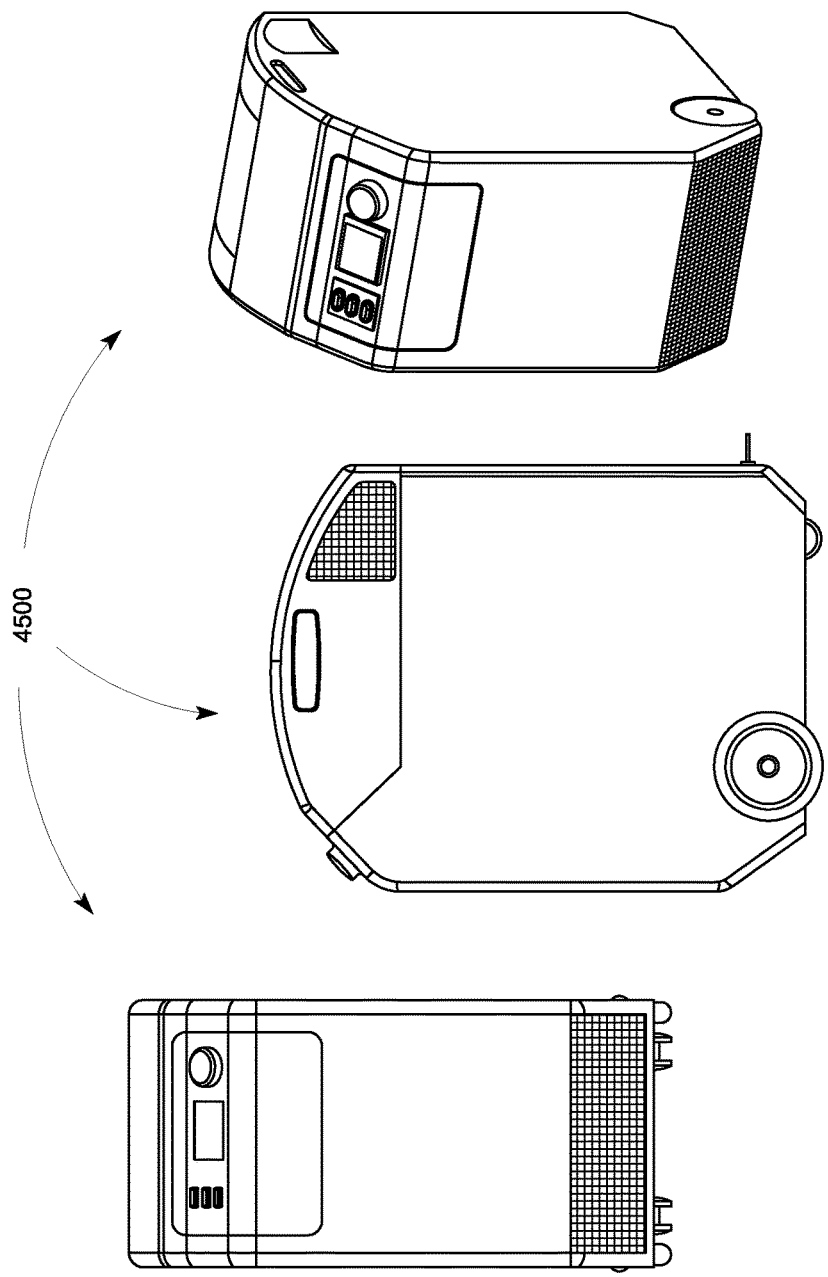
FIG. 45A illustrates a front view, a side view, and a perspective view of another apparatus for treating air 4500 according to some embodiments of the subject matter disclosed herein.
Figure 45B:
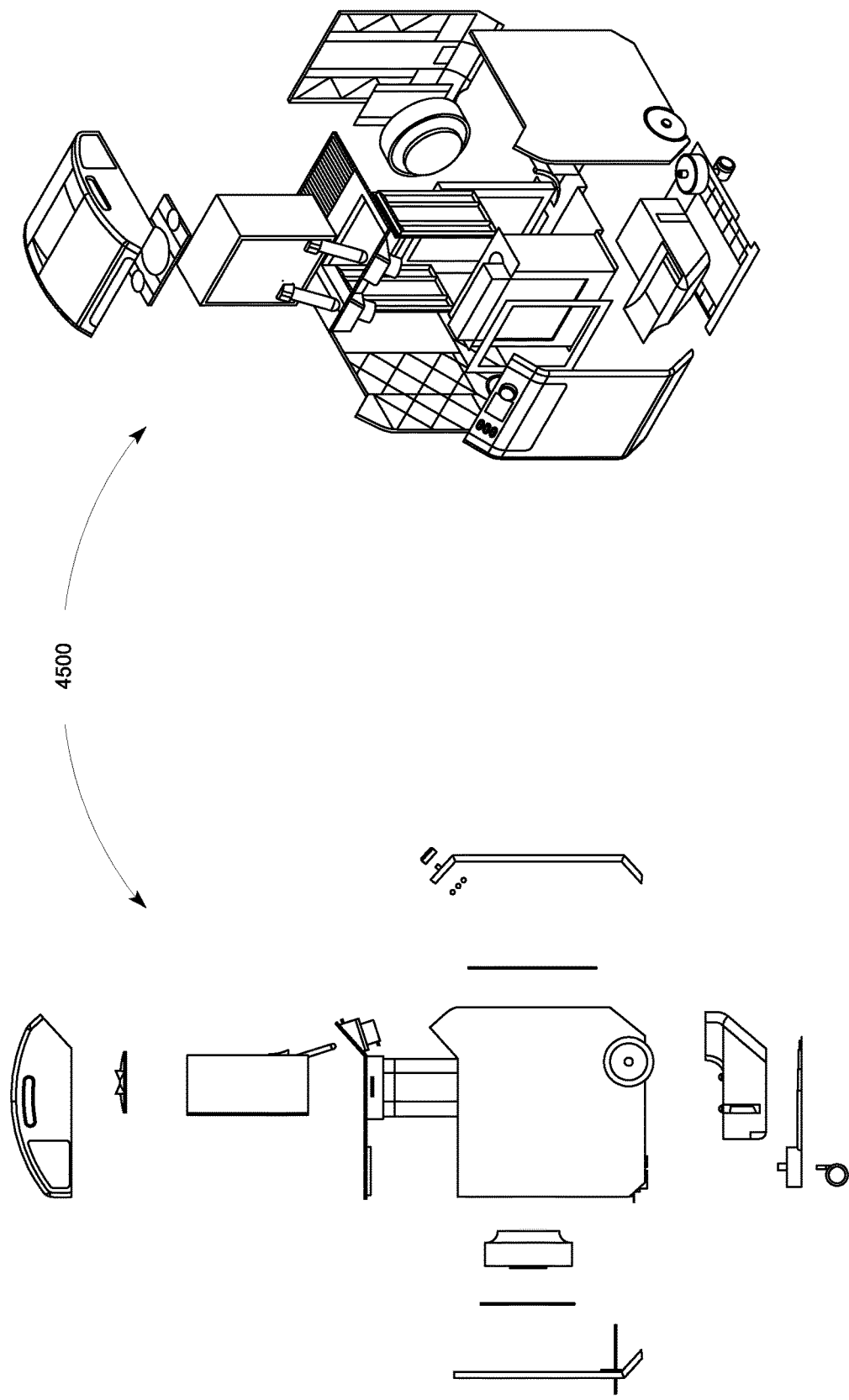
FIG. 45B illustrates two exploded views of the apparatus for treating air 4500.

FIG. 45A illustrates a front view, a side view, and a perspective view of another apparatus for treating air 4500 according to some embodiments of the subject matter disclosed herein. FIG. 45B illustrates two exploded views of the apparatus for treating air 4500. FIG. 45C illustrates a partial sectional view of the apparatus for treating air 4500.

The apparatus for treating air 4500 can include a housing 4502, an air inlet 4504, and an air outlet 4506. The housing 4502 can enclose an air treatment zone 4508 and an ozone removal zone 4510. As illustrated in FIG. 45C, the ozone removal zone 4510 can be positioned downstream of the air treatment zone 4508 with respect to a flow direction of the air being treated.

The apparatus for treating air 4500 can also include an UV light source 4512 in the air treatment zone 4508. The UV light source can generate ozone form the air. The UV light from the UV light source and the ozone generated by the UV light source can treat the air (e.g., clean, sanitize, or deodorize) in the air treatment zone 4508. The UV light source can include a UV lamp generating UV light in the wavelength of about 185 nm. The 185 nm UV lamp can generate ozone from the air and can also help treating the air (e.g., kill germs). The UV light source can also include another UV lamp generating UV light in the wavelength of about 254 nm. The 254 nm UV lamp can remove/decompose ozone and can also help treating the air (e.g., kill germs). The ozone removal rate of the 254 nm UV lamp can be configured to be same as or different from the ozone generation rate of the 185 nm UV lamp. The combination of UV lamps with different UV wavelengths that both generate and destroy ozone can create highly reactive species (e.g., free radicals) that increase the reaction rate of contaminants with ozone. In addition, ozone can be generated by other means, such as a corona discharge unit to increase the amount of ozone in the air treatment zone. For example, a corona discharge unit can be added in place of or in addition to an ozone-generating UV lamp (e.g., a 185 nm UV lamp). In some embodiments, a separate UV lamp (e.g., a 254 nm UV lamp) can be used in combination with an ozone generator such as a corona discharge unit. For example, the 254 nm UV lamp can provide additional energy to accelerate the reaction in the air treatment zone (e.g., killing germs, cleaning, deodorizing, etc.), thus improving the performance of the apparatus for treating air 4500.

The apparatus for treating air 4500 can also include catalyst 4514 in the ozone removal zone 4510. The catalyst 4514 can remove at least a portion of the ozone generated by the UV light source 4512. In some embodiments, the ozone removal zone 4510 can include one section of catalyst 4514. In some embodiments, the ozone removal zone 4510 can include two or more sections of catalyst, separated by one or more spacers. The two or more catalysts can be made with different materials in order to achieve multiple objectives. For example, once catalyst layer can be used to remove ozone only, while a second catalyst layer can be used to assist the oxidation of contaminants in the air stream or to complete the oxidation of contaminants that are partially oxidized by the ozone.

The apparatus for treating air 4500 can also include a particle matter (PM) filter 4516. In some embodiments, the PM filter 4516 can include a High Efficiency Particulate Arresting (HEPA) filter. The PM filter 4516 can be positioned between the air treatment zone 4508 and the ozone removal zone 4510. The UV light from the UV light source 4512 and the ozone generated by the UV light source can treat the PM filter. Treating the PM filter can include cleaning, sanitizing, and deodorizing the PM filter, thus extending its usage life. The PM filter may need to be replaced periodically. Extending the usage life of the PM filter can help lowering the operating cost the apparatus for treating air 4500. In some embodiments, the PM filter 4516 can allow the ozone generated by the UV light source 4512 to penetrate the PM filter 4516 to treat both upstream and downstream sides of the PM filter 4516. In some embodiments, the PM filter 4516 can allow the ozone generated by the UV light source 4512 to penetrate the PM filter 4516 to treat an inlet of the ozone removal zone 4510. In some embodiments, the apparatus for treating air 4500 can also include a 254 nm UV lamp positioned between the PM filter 4516 and the ozone removal zone 4510. In some embodiments, the structure of the filter 4516 can be made of a material (e.g., metal or fiberglass) that can sustain UV radiation in an extended period of time. In some embodiments, the structure of the filter 4516 can be made of other materials (e.g., plastics), which can be covered or coated with a UV protective layer (e.g., metal shield or layer).

The PM filter 4516 can be uni-directional (i.e., designed in a way that the air flows in one direction) or bi-directional (i.e., designed in a way that the air can flow in both directions). When the PM filter 4516 is bi-directional, it can be flipped after certain period of use to, e.g., achieve better performance or extend usage life. In some embodiments, the PM filter 4516 can include a single filter. In some embodiments, the PM filter 4516 can include multiple filters. In one example, each of the multiple filters can have the same type and/or dimension. In another example, the multiple filters can be of different types and/or dimensions. The multiple filters can be stacked next to each other and can optionally have space between the multiple filters.

In some embodiments, the apparatus for treating air 4500 can also include a pre-filter (not shown in FIG. 45C). The pre-filter can include a loose weave filter. In some embodiments, the pre-filter can be positioned upstream of the PM filter 4516 and downstream of the air treatment zone 4508. The pre-filter can allow the UV light from the UV light source 4510 to penetrate the pre-filter to treat the PM filter 4516. In some embodiments, the pre-filter can be positioned upstream of the air treatment zone 4508.

The apparatus for treating air 4500 can also include an air mover 4518. The air mover 4518 can be positioned near the air outlet 4506. The air mover 4518 can draw the air through the air inlet 4504 into the air treatment zone 4508 from outside the housing 4502, moving the air through the air treatment zone 4508, the PM filter 4516, and the ozone removal zone 4510, and then emitting the air through the air outlet 4506 out of the apparatus 4500. In some embodiments, the air mover 4518 can include a fan and a volute 4520. The volute can accelerate the air flow, alleviate pressure drop, and/or reduce noise.

In some embodiments, the interior surface of the air treatment zone 4508 can be at least partially coated with a reflector layer (e.g., metal layer such as aluminum).

Figure 45D:
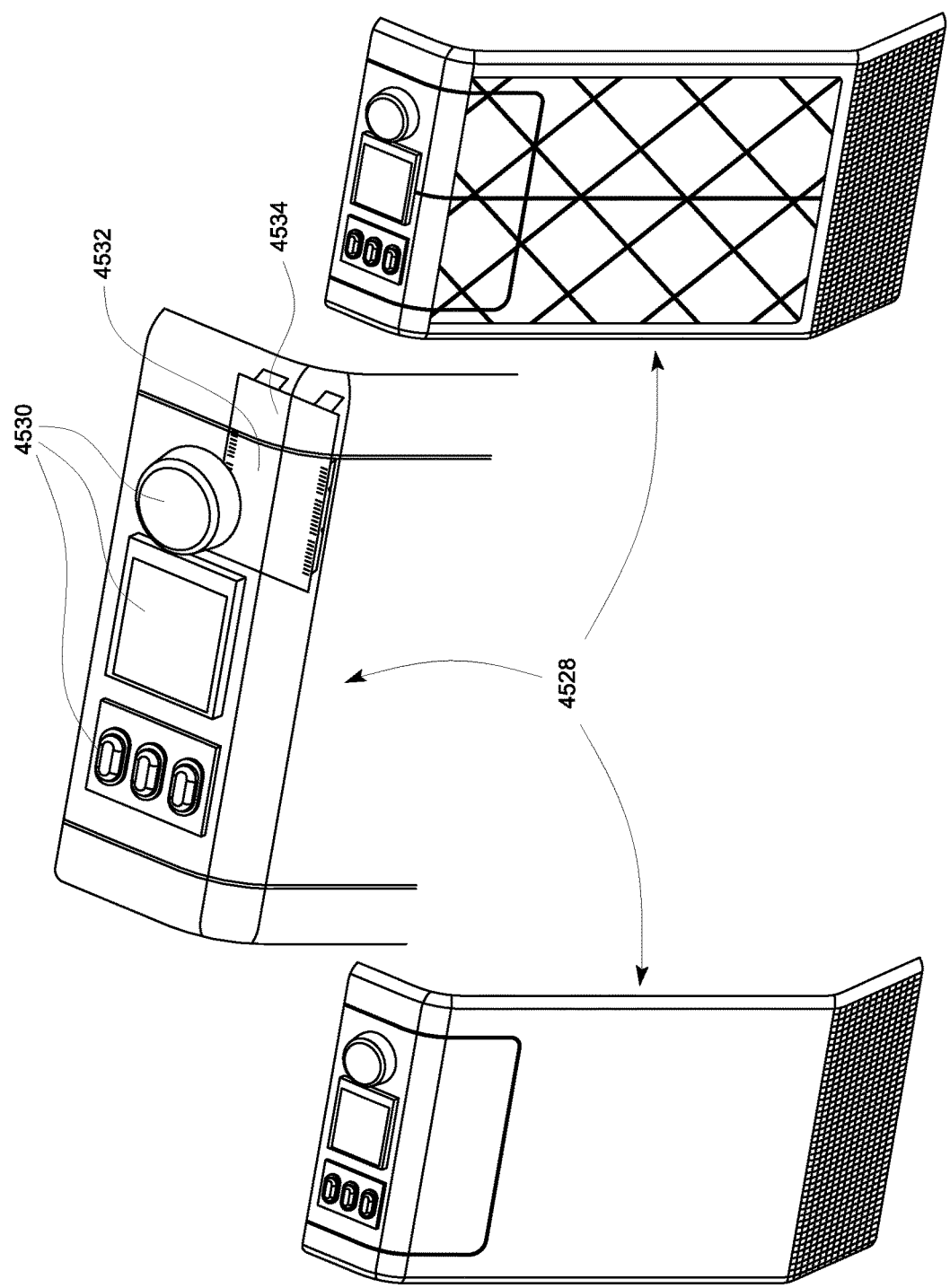
FIG. 45D illustrates a front panel of the apparatus for treating air 4500.

FIG. 45D illustrates a front panel 4528 of the apparatus for treating air 4500. The front panel 4528 can include a user interface module 4530 that can receive user input (e.g., selection of an operation mode) and present information to the user (e.g., operating condition of the apparatus 4500). The front panel 4528 can also include an electronic control module 4532. The electronic control module 4532 can be mounted inside the front panel 4528 or be positioned anywhere inside the housing 4502. The electronic control module 4532 can set the apparatus 4500 to operate in one of multiple operation modes. For example, in a regular operation mode, where the UV light source 4512 is on and the air mover 4518 operates at a certain set speed. The electronic control module 4532 can set the apparatus 4500 to operate in one operation mode based on a user selection. The electronic control module 4532 can also monitor and record time information, such as operating time (duration) of serviceable components, operating time between cleaning intervals, and time of day.

The electronic control module 4532 can also set the apparatus 4500 to operate in one operation mode automatically based on time and/or output of one or more sensors 4522. The one or more sensors 4522 can be placed near the air inlet 4504, near the air outlet 4506, or both. The one or more sensors 4522 can also be placed anywhere inside (e.g., in the air treatment zone 4508) or outside the housing 4502. The one or more sensors 4522 can detect information about an ambient environment where the apparatus 4500 is situated. In one example, a sensor, such as a motion sensor or infrared sensor, can detect the occupancy of a room, e.g., whether there are people in the room. In another example, a sensor can detect the temperature, humidity, air quality, and/or contaminant content and level (e.g., particulate, formaldehyde, ozone, volatile organic compounds (VOCs), carbon monoxide (CO), or other toxic gases) in the air in the environment.

In some embodiments, the apparatus for treating air 4500 can include a self-cleaning mode. Interior components of the apparatus for treating air, such as the PM filter(s), can accumulate odors as well as particulate matters. The odors can come from cigarette smoke, cooking odors, mildew, bacteria that grow on the interior components (e.g., filter), collected material, or the particulate material itself. The odors embedded in the interior components (e.g., filter) or emanated from the collected material on the filter can be redistributed into the environment when the apparatus for treating air 4500 is turned on. In addition, the presence of odors can shorten the effective life of the filter because it will need to be replaced due to odor before it is "full" of particulate matter (i.e., when the air flow rate has significantly dropped due to the accumulation of particulate on the filter). The self-cleaning mode can help clean the interior components (e.g., filter), including removing odors that can otherwise accumulate on the interior components (e.g., filter).

In the self-cleaning mode, the UV light source 4516 is on, the UV light from the UV light source and the ozone generated by the UV light source can treat and clean interior components (e.g., interior surfaces and filters) of the apparatus 4500, and the air mover 4518 can operate in a speed lower than the speed during a regular operation mode.

The apparatus of treating air 4500 can also include an ozone removal mode. In the ozone removal mode, the 185 nm UV lamp is off and the 254 nm UV lamp is on.

The apparatus of treating air 4500 can also include a particle removal only mode. In the particle removal only mode, any and all UV lamps are turned off. The apparatus of treating air 4500 can also include an eco-mode. In the eco-mode mode, the speed of the air mover (e.g., fan) can be limited to conserve power consumption and/or reduce operation noise.

The front panel 4528 can also include a wireless communication module 4534. The wireless communication module 4534 can be mounted inside the front panel 4528 or be positioned anywhere inside the housing 4502. The apparatus for treating air 4500 can communicate with a computer system (e.g., a central management system) wirelessly (e.g., Wi-Fi or Bluetooth) via the wireless communication module 4534. In some embodiments, the electronic control module 4532 can set the apparatus for treating air 4500 to operate in a particular operation mode based on an instruction received from a central management system via the wireless communication module 4534. The instruction can at least partially based on information received from another apparatus for treating air 4500.

Figure 46:
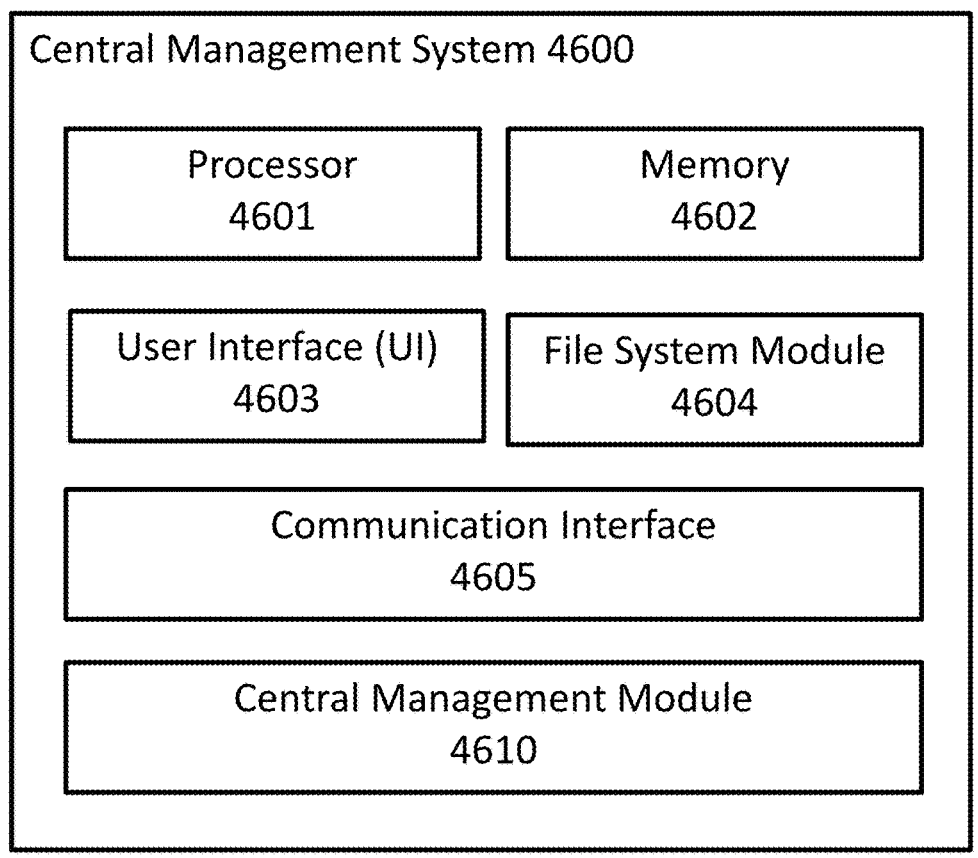
FIG. 46 is a block diagram of a central management system 4600 according to some embodiments of the subject matter disclosed herein.

FIG. 46 is a block diagram of a central management system 4600 according to some embodiments of the subject matter disclosed herein. The central management system 4600 can manage multiple apparatuses for treating air 4500 in multiple environments. The central management system 4600 can include at least one processor 4601 and at least one memory 4602. The processor 4601 can be hardware that is configured to execute computer readable instructions such as software. The processor 4601 can be a general processor or be an application specific hardware (e.g., an application specific integrated circuit (ASIC), programmable logic array (PLA), field programmable gate array (FPGA), or any other integrated circuit). The processor 4601 can execute computer instructions or computer code to perform desired tasks. The memory 4602 can be a transitory or non-transitory computer readable medium, such as flash memory, a magnetic disk drive, an optical drive, a programmable read-only memory (PROM), a read-only memory (ROM), a random access memory (RAM), or any other memory or combination of memories. Both hardware and software can be located either in proprietary facilities, or hosted by a third party with or without direct access to the physical hardware location, e.g., in a cloud computing environment.

The central management system 4600 can also include a user interface (UI) 4603, a file system module 4604, and a communication interface 4605. The UI 4603 can provide an interface for users to interact with the central management system 4600 in order to manage multiple apparatuses for treating air 4500. The file system module 4604 can be configured to maintain a list of all data files, including both local data files and remote data files, in folders in a file system. The file system module 4604 can be further configured to coordinate with the memory 4602 to store and cache files/data. The communication interface 4605 can allow the central management system 4600 to communicate with external resources (e.g., a network or a remote client/server) or users. In some embodiments, the communication interface 4605 can include a web server, which can provide a web interface to the users of the central management system 4600. The central management system 4600 can also include a central management module 4610. The central management system 4600 can include additional modules, fewer modules, or any other suitable combination of modules that perform any suitable operation or combination of operations.

One or more components in the central management system 4600 illustrated in FIG. 46 can be omitted; additional component(s) can be added. FIG. 46 is a conceptual illustration of the central management system 4600. Various components of the central management system 4600 can positioned locally to each other or distributed among multiple locations (e.g., across a network).

In some embodiments, the central management system 4600 can be a computer or a smart device (e.g., a smart phone or tablet).

Figure 47:
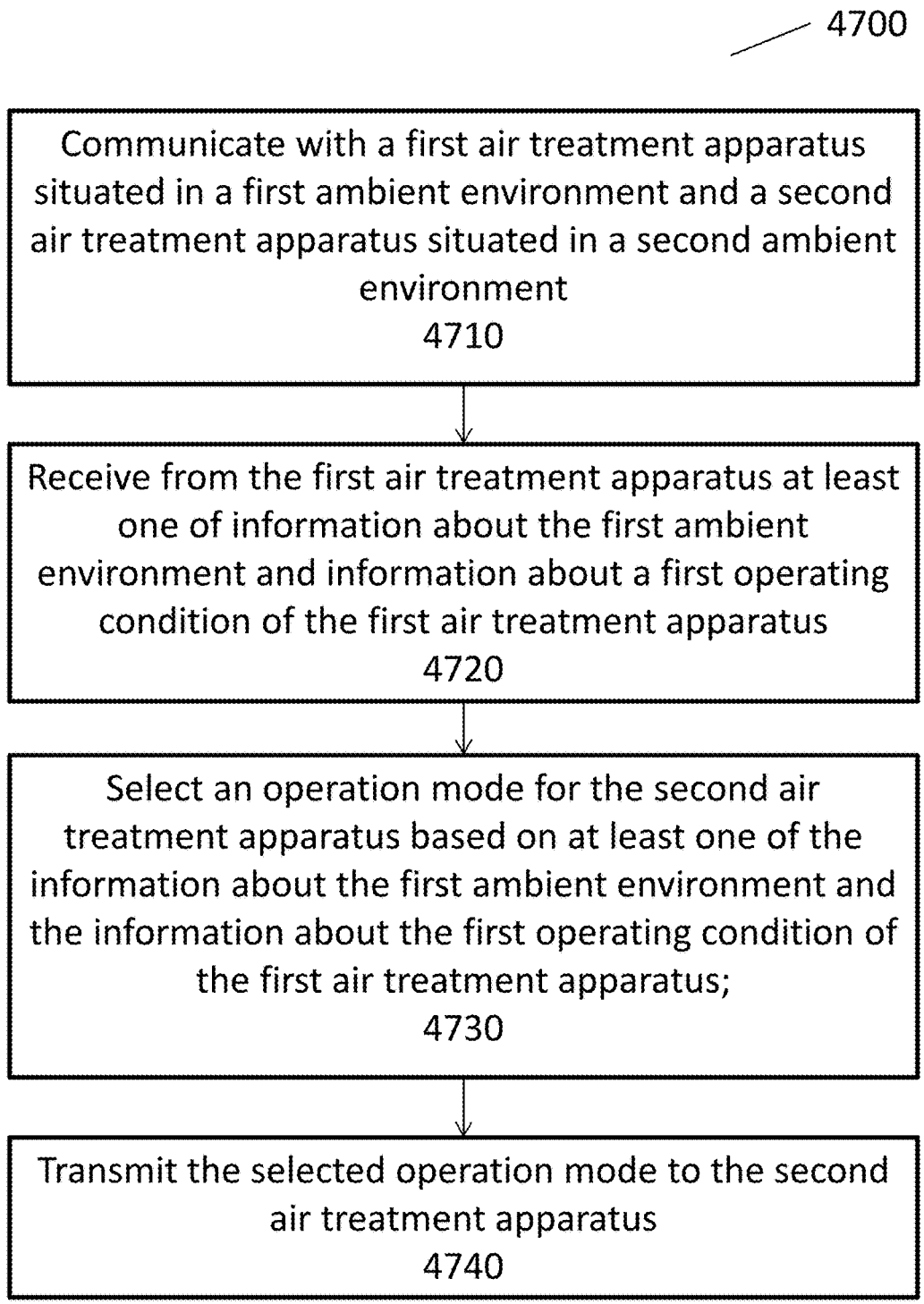
FIG. 47 illustrates a process of managing multiple apparatuses for treating air 4700 according to some embodiments of the subject matter disclosed herein.

The central management module 4610 can manage multiple apparatuses for treating air in multiple environments. FIG. 47 illustrates a process of managing multiple apparatuses for treating air 4700 according to some embodiments of the subject matter disclosed herein. At 4710, the central management module 4610 can communicate with a first air treatment apparatus situated in a first ambient environment and a second air treatment apparatus situated in a second ambient environment. At 4720, the central management module 4610 can receive from the first air treatment apparatus at least one of information about the first ambient environment and information about a first operating condition of the first air treatment apparatus. At 4730, the central management module 4610 can select an operation mode for the second air treatment apparatus based on at least one of the information about the first ambient environment and the information about the first operating condition of the first air treatment apparatus. At 4740, the central management module 4610 can transmit the selected operation mode to the second air treatment apparatus. One or more steps in the process of managing multiple apparatuses for treating air 4700 illustrated in FIG. 47 can be omitted; additional step(s) can be added.

In some embodiments, the central management system 4600 can also communicate with other local/remote sources of information, such as a third-party web service that can provide additional information. For example, the central management system 4600 can receive current/forecasted weather information and/or air quality information from a weather information server. The central management system 4600 can use the information (e.g., air quality) as additional inputs when it manages or coordinates one or more apparatuses for treating air. For example, if the weather forecast calls for poor air quality (e.g., heavy smog), the central management system 4600 can configure certain apparatuses for treating air to run at a certain time based on the forecast.

Figure 48:
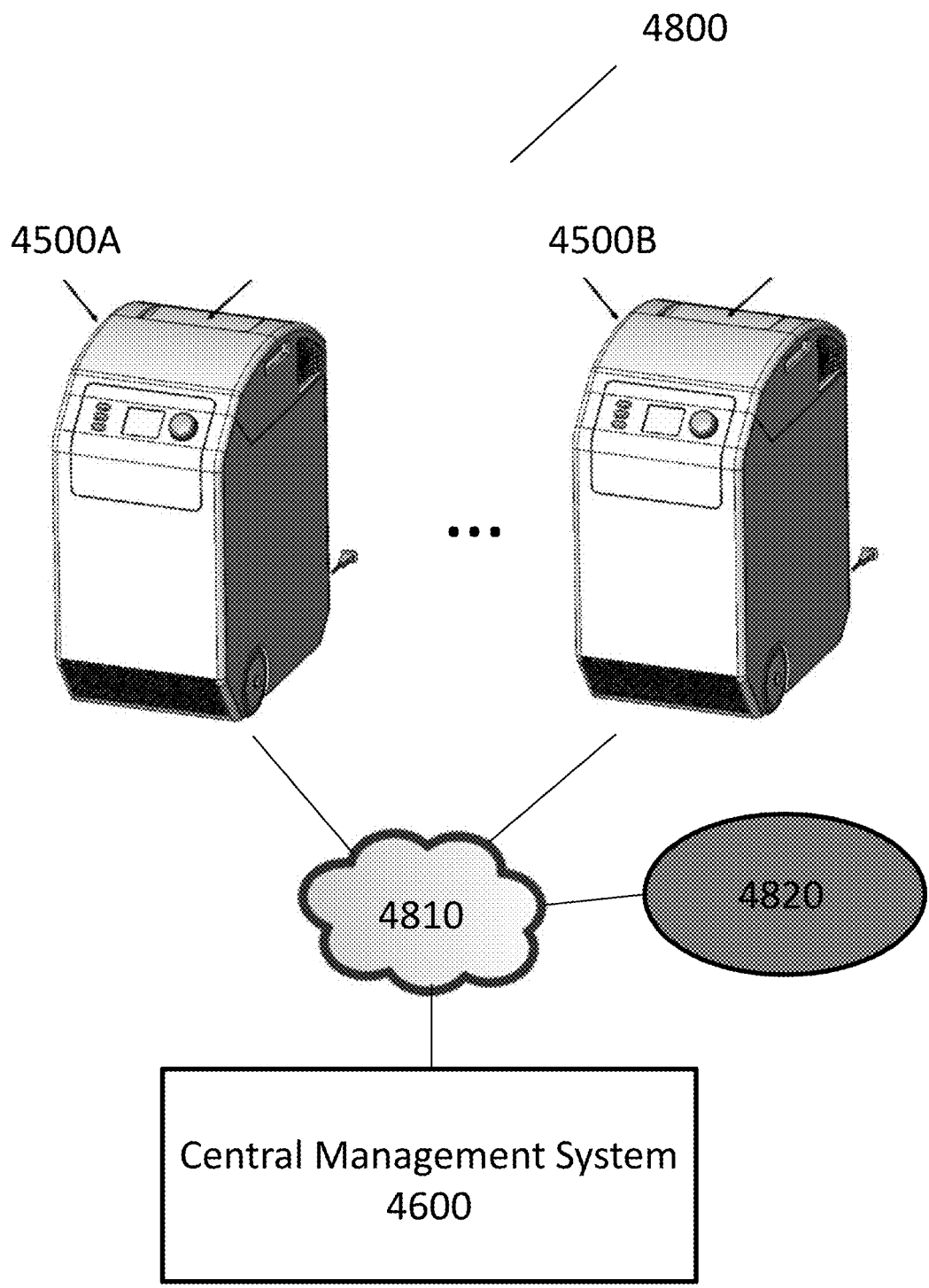
FIG. 48 illustrates an arrangement of managing multiple apparatuses for treating air 4800 according to some embodiments of the subject matter disclosed herein.

FIG. 48 illustrates an arrangement of managing multiple apparatuses for treating air 4800 according to some embodiments of the subject matter disclosed herein. The arrangement 4800 can include one or more apparatuses for treating air (e.g., 4500A and 4500B), a network 4810, additional data source(s) 4820, and a central management system 4600. The one or more apparatuses for treating air (e.g., 4500A and 4500B) can communicate with the central management system 4600 via the network 4810. Alternatively, the one or more apparatuses for treating air (e.g., 4500A and 4500B) can communicate with the central management system 4600 directly. In some embodiments, the one or more apparatuses for treating air (e.g., 4500A and 4500B) can communicate with each other directly. The additional data source(s) 4820 can be local or remote. The additional source(s) can communicate with the central management system 4600 directly or via the network 4810. In one example, the additional data source(s) can be a third-party web service that can provide additional information (e.g., current or forecasted weather information, air quality information from a weather information server).

In some embodiments, the arrangement 4800 can allow for controlling the operation of multiple devices in a home that work together to improve air quality and environmental health and comfort. For example, the arrangement 4800 can provide coordinated control of multiple apparatuses for treating air 4500 in a multi-room building with the objective of maximizing pollutant removal while minimizing energy use, filter service, and noise. Additionally, devices such as separate air quality sensor modules (e.g., providing information inputs to the central management system 4600) or lighting switches, humidifiers, dehumidifiers, heating or cooling devices (e.g., controlled by output of the central management system 4600) can be added in the arrangement 4800.

Selection of operation modes on any apparatus for treating air 4500 involves a trade-off of choices among, e.g., cleaning performance, noise, energy consumption, and service impact. For example: lower fan speed is quieter and uses less power, but removes less particulate. UV bulb use increases the amount of VOC, odor, and cigarette smoke removed but increases energy use and shortens the interval between bulb replacements. UV bulb use decreases odor of the PM filter and extend its productive life, but increases energy use and requires more frequent replacement of the UV bulb.

There are trade-offs among the usage of the various operation modes to achieve the best possible performance at the lowest cost of ownership. This optimization can be performed over one or more apparatuses for treating air 4500 operating in a home. Depending on occupancy, contaminant level, time of day, room usage, and manual choices, the central management system 4600 can control the operation modes and/or fan speeds of any or all the apparatuses for treating air 4500 in the home.

In addition, the arrangement 4800 can signal a user (e.g., a homeowner) if there is any excessively high level of contaminant in a particular environment (e.g., the home). In one example: the central management system 4600 can infer from the sensor readings of one or more the apparatuses for treating air 4500 and from occupancy and time of day that food is being cooked in the kitchen. To remove those odors and prevent them from spreading throughout the home, the central management system 4600 turns on the apparatus for treating air in the kitchen to maximize odor removal capability. An apparatus for treating air in an adjacent room is turned on to odor removal as well, to catch odors before they build up and spread through the home or apartment. But other apparatuses for treating air can be placed on other modes appropriate for their usage.

In another example, the central management system 4600 can set an apparatus for treating air 4500 to the "self-clean" mode when the ambient air of a room is clean (and no air cleaning is needed) and when no one is in the room. Alternatively, the "self-clean" mode can be run at night or when electricity rates are low.

In another example, when an apparatus for treating air 4500 in a bed room detects a high level of PM2.5, indicating that a window or other ventilation duct may be open, the apparatus for treating air 4500 can run in a high speed to remove the PM 2.5 and keep up with the infiltration rate. An apparatus for treating air 4500 in a room adjacent to the affected room can be turned on to inhibit the flow of PM2.5 to other rooms. If the adjacent room is occupied, the fan speed can be set to medium to offer quiet operation but to protect against the migration of PM 2.5 throughout the home. Other apparatuses for treating air 4500 can operate based on local sensor input and algorithm choices.

In another example, the central management system 4600 can monitor filter and bulb usage in one or more apparatuses for treating air 4500. The central management system 4600 can provide information to a user on likely dates for replacement of bulbs and filters, and suggest the number of components to purchase at one time (to save time and shipping costs) and define the date range to service the one or more apparatuses for treating air 4500.

Figure 49A:
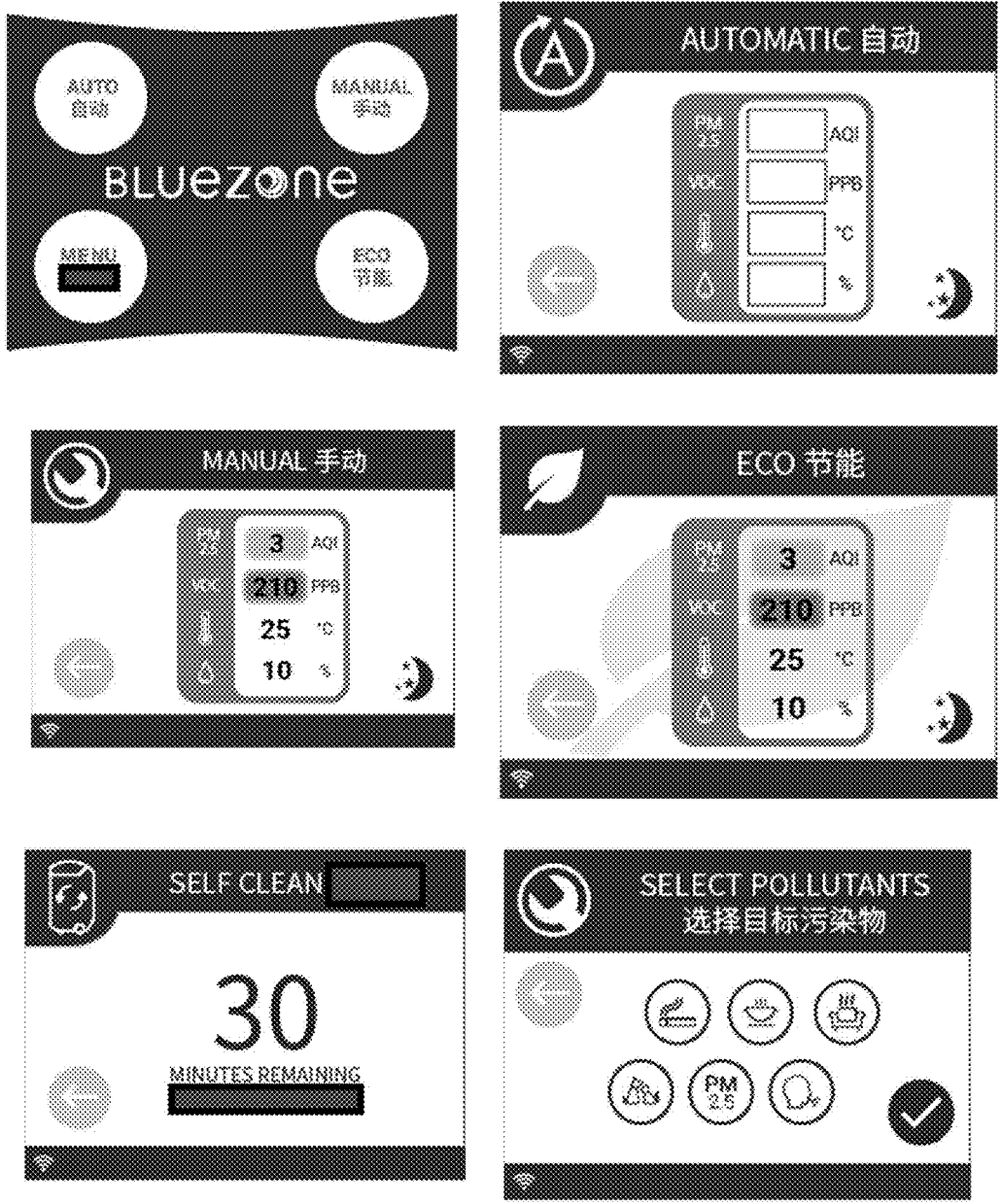
FIGS. 49A-49C contain certain sample screenshots illustrating functions, operations, and user interface of the apparatus for treating air 4500 according to some embodiments of the subject matter disclosed herein.
Figure 49B:
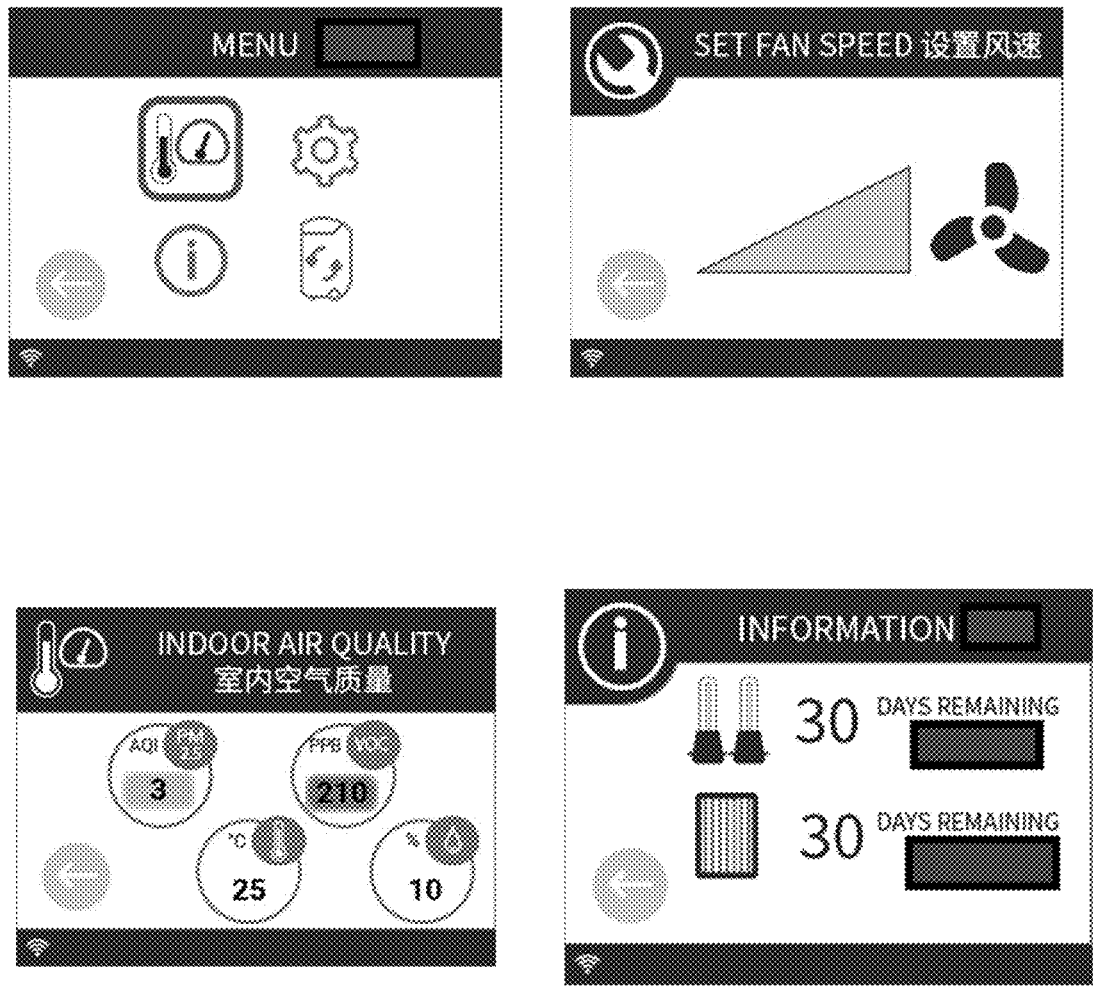
Figure 49C:
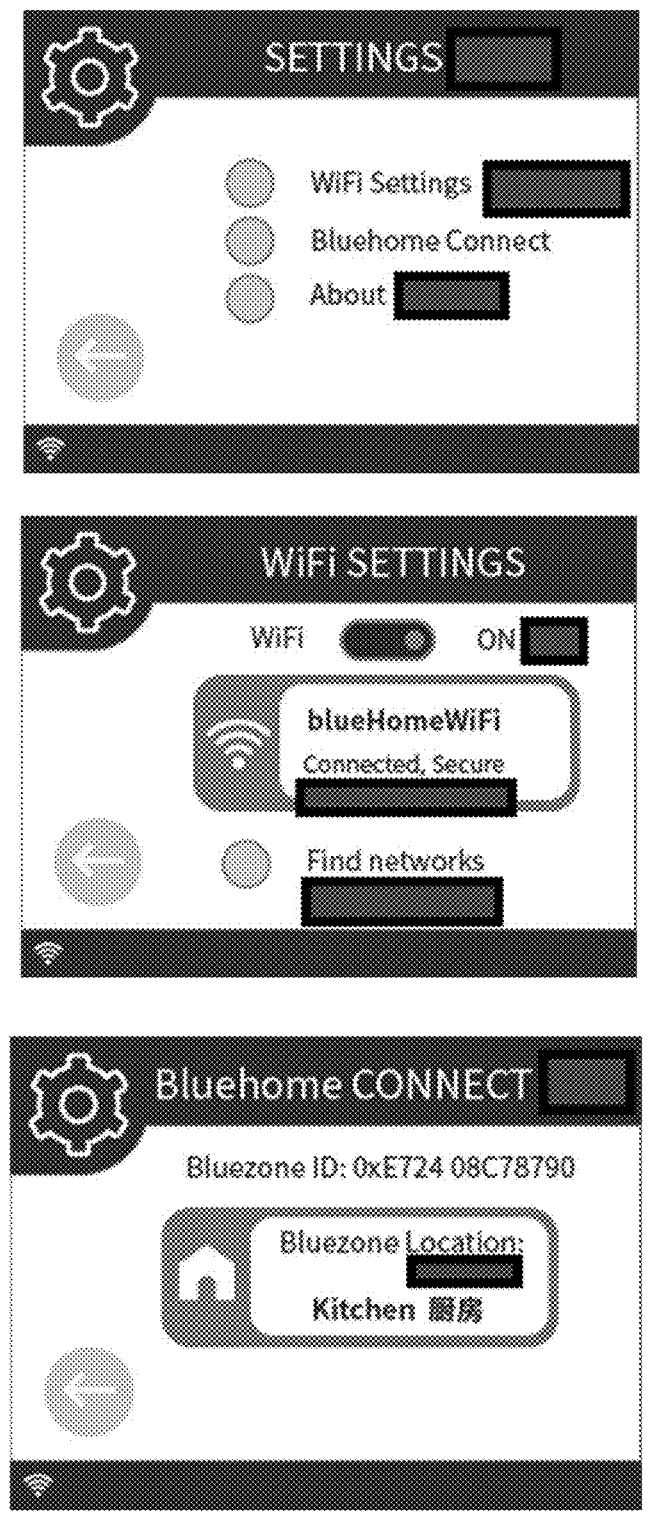
Figure 50A:
FIGS. 50A-50B contain certain sample screenshots illustrating functions, operations, and user interface of the central management system 4600 according to some embodiments of the subject matter disclosed herein.
Figure 50B:

FIGS. 49A-49C contain certain sample screenshots illustrating functions, operations, and user interface of the apparatus for treating air 4500 according to some embodiments of the subject matter disclosed herein. FIGS. 50A-50B contain certain sample screenshots illustrating functions, operations, and user interface of the central management system 4600 according to some embodiments of the subject matter disclosed herein.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or functional programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a LCD or LED) for displaying information to the user and in some instances a keyboard and a pointing device (e.g., a mouse or a trackball) by which the user may provide input to the computer. In other instances, the subject matter described herein may be implemented on mobile devices such as tablets, phablets, or/and smartphones. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

While in the foregoing detailed description the subject matter disclosed herein has been described in relation to certain embodiments thereof, and many details have been set forth for purposes of illustration, it will be apparent to those skilled in the art that the subject matter disclosed herein is susceptible to additional embodiments and that certain of the details described herein can be varied considerably without departing from the basic principles of the subject matter disclosed herein.

Although a few variations have been described in detail above, other modifications are possible. For one example, the systems or devices depicted in the accompanying figures and described herein do not require the particular arrangements to achieve desirable results. In addition, one or more additional components can be added to the systems or devices; one or more existing components can be omitted. For another example, the logic flows or processes depicted in the accompanying figures and described herein do not require the particular order shown to achieve desirable results. In addition, one or more additional steps can be added to the logic flows or processes; one or more existing steps can also be omitted. Other embodiments may be within the scope of the following claims.

It is to be understood that the disclosed subject matter is not limited in its application to the details of construction and to the arrangements of the components set forth in the description or illustrated in the drawings. The disclosed subject matter is capable of other embodiments and of being practiced and carried out in various ways. Also, it is to be understood that the phraseology and terminology employed herein are for the purpose of illustration and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

For example, the term "air" is used in general in this document—it can be interpreted to include both natural air and any gaseous or vaporous matters.

We claim:

1. An apparatus for treating air, comprising:
   an enclosure enclosing an air treatment zone, the enclosure including an air inlet and a removable cover on a cover side and an enclosure outlet on an end wall;
   an ultraviolet (UV) light source enclosed within the air treatment zone and configured to generate ozone from the air, wherein the UV light source is disposed between the air inlet and the enclosure outlet, and UV light from the UV light source and the ozone generated by the UV light source treat the air in the air treatment zone;
   a catalyst housing connected to the enclosure at the enclosure outlet, the catalyst housing enclosing an ozone removal zone, wherein the ozone removal zone is positioned downstream of the air treatment zone with respect to a flow direction of the air being treated;
   the ozone removal zone comprising a first catalyst section with a first catalyst, a second catalyst section with the first catalyst or a second catalyst, and an air distribution spacer positioned between and separating the first and second catalyst sections; and
   an air outlet and an air mover positioned downstream of the second catalyst section and configured to draw the air through the air inlet into the air treatment zone from outside the enclosure, moving the air through the air treatment zone and the ozone removal zone, and then emitting the air through the air outlet out of the apparatus.

2. The apparatus for treating air in claim 1, wherein the second catalyst is different than the first catalyst.

3. The apparatus for treating air in claim 1, wherein the air distribution spacer comprises a hollow structure to separate the first and second catalyst sections.

4. The apparatus for treating air in claim 3, wherein the hollow structure redistributes air from the first catalyst section before entry into the second catalyst section to improve a performance of the ozone removal zone.

5. The apparatus for treating air in claim 1, wherein the cover comprises a removable light cover to access the UV light source.

6. The apparatus for treating air in claim 5, further comprising a bulb bracket configured to hold the UV light source beneath the light cover.

7. The apparatus for treating air in claim 6, wherein the air inlet is disposed on a side of the light cover and bulb bracket that is opposite the enclosure outlet.

8. The apparatus for treating air in claim 1, further comprising a proximity sensor attached to the enclosure, wherein the proximity sensor detects the presence of the cover over the apparatus.

9. The apparatus for treating air in claim 8, wherein the proximity sensor is a magnetic proximity sensor.

10. The apparatus for treating air in claim 9, wherein the UV light source is turned on only if the proximity sensor detects the presence of the cover.

11. The apparatus for treating air in claim 8, wherein the apparatus for treating air is mounted inside a refrigerator and the cover is part of an inner surface of the refrigerator.

12. The apparatus for treating air in claim 11, further comprising a power connector that connects to a power source inside the refrigerator.

13. The apparatus for treating air in claim 1, wherein an interior surface of the enclosure of the air treatment zone is at least partially coated with a reflector layer.

14. The apparatus for treating air in claim 13, wherein the interior surface of the enclosure in the air treatment zone is at least partially coated with aluminum.

15. The apparatus for treating air in claim 1, further comprising a positioner configured to secure the apparatus inside a cabin of a vehicle.

16. The apparatus for treating air in claim 15, wherein the positioner is configured to secure the apparatus into a cup holder inside the cabin of the vehicle.

17. The apparatus for treating air in claim 15, wherein the positioner is configured to secure the apparatus into a seat of the vehicle.

18. The apparatus for treating air in claim 16, wherein an interior surface of the enclosure of the air treatment zone is at least partially coated with a reflector layer.

19. The apparatus for treating air in claim 15, further comprising a ballast configured to convert power received from the vehicle to higher frequency and higher voltage suitable for the apparatus.

* * * * *